US010188733B2

(12) United States Patent
von Andrian et al.

(10) Patent No.: US 10,188,733 B2
(45) Date of Patent: Jan. 29, 2019

(54) VACCINES COMPRISING BISPHOSPHONATE AND METHODS OF USE THEREOF

(75) Inventors: Ulrich H. von Andrian, Chestnut Hill, MA (US); Matteo Iannacone, Milan (IT); Elena Tonti, Riccione (IT); Elliott Ashley Moseman, Rockville, MD (US)

(73) Assignee: President and Fellows of Harvard College, Cambridge, MA (US)

( * ) Notice: Subject to any disclaimer, the term of this patent is extended or adjusted under 35 U.S.C. 154(b) by 631 days.

(21) Appl. No.: 13/880,795

(22) PCT Filed: Oct. 21, 2011

(86) PCT No.: PCT/US2011/057224
§ 371 (c)(1),
(2), (4) Date: Jul. 1, 2013

(87) PCT Pub. No.: WO2012/054807
PCT Pub. Date: Apr. 26, 2012

(65) Prior Publication Data
US 2013/0309270 A1 Nov. 21, 2013

Related U.S. Application Data

(60) Provisional application No. 61/405,777, filed on Oct. 22, 2010.

(51) Int. Cl.
*A61K 39/395* (2006.01)
*A61K 47/24* (2006.01)
*A61K 39/00* (2006.01)
*A61K 47/02* (2006.01)
(52) U.S. Cl.
CPC .............. *A61K 47/24* (2013.01); *A61K 39/00* (2013.01); *A61K 47/02* (2013.01); *A61K 2039/55511* (2013.01); *Y02A 50/464* (2018.01); *Y02A 50/476* (2018.01); *Y02A 50/487* (2018.01); *Y02A 50/489* (2018.01)
(58) Field of Classification Search
None
See application file for complete search history.

(56) References Cited

U.S. PATENT DOCUMENTS

| 6,677,320 | B2 | 1/2004 | Diederich et al. | |
|---|---|---|---|---|
| 2002/0098203 | A1* | 7/2002 | Gustavsson et al. | ........................ A61K 9/1623 424/234.1 |
| 2006/0165744 | A1 | 7/2006 | Jamil et al. | |
| 2007/0025960 | A1 | 2/2007 | Pauza et al. | |
| 2007/0190169 | A1 | 8/2007 | Nieda et al. | |
| 2007/0218116 | A1 | 9/2007 | Schwendener | |
| 2009/0196887 | A1* | 8/2009 | Morita et al. | |
| 2009/0202596 | A1 | 8/2009 | Pedrani et al. | |
| 2009/0311237 | A1 | 12/2009 | Frost | |
| 2012/0156280 | A1 | 6/2012 | Dow et al. | |
| 2013/0034579 | A1 | 2/2013 | Harper et al. | |

FOREIGN PATENT DOCUMENTS

| EP | 1930414 B1 | 7/2012 |
|---|---|---|
| WO | WO-2009/051837 A2 | 4/2009 |
| WO | WO-2010/042876 A1 | 4/2010 |

OTHER PUBLICATIONS

Conte et al. The Oncologist, 2004, vol. 9 (supp 4), p. 28-37.*
Delemarre, Frans G.A. et al., "Elimination of Spleen and of Lymph Node Macrophages and Its Difference in the Effect on the Immune Response to Particulate Antigens." *Immunobiol.* vol. 182 (1990). 70-78.
Frith, Julie C. et al., "Clodronate and Liposome-Encapsulated Clodronate Are Metabolized to a Toxic ATP Analog, Adensoine 5'-(β,γ-Dichloromethylene) Triphosphate, by Mammalian Cells in Vitro." *Journal of Bone and Mineral Research* vol. 12, No. 9 (1997). 1358-1367.
Gonzalez, Santiago F. et al., "Capture of influenza by medullary dendritic cells via SIGN-R1 is essential for humoral immunity in draining lymph nodes." *Nature Immunology* (2010). 1-9.
Granstein, Richard D. et al., "Augmentation of Cutaneous Immune Responses by ATP{gamma} S: Purinergic Agonists Define a Novel Class of Immunologic Adjuvants." *J. Immunol.* vol. 174 (2005). 7725-7731.
Iannacone, Matteo et al. "Subcapsular sinus macrophages prevent CNS invasion on peripheral infection with a neurotropic virus." *Nature* vol. 455 (2010). 1079-1085.
International Search Report and Written Opinion for Application No. PCT/US2011/057224, dated Apr. 21, 2012, 17 pages.
Junt, Tobias et al., "Subcapsular sinus macrophages in lymph nodes clear lymph-borne viruses and present them to antiviral B cells." *Nature* vol. 450 (2007). 110-116.
Kornbluth, Richard S. et al., "Immunostimulatory combinations: designing the next generation of vaccine adjuvants." *Journal of Leukocyte Biology* vol. 80 (2006). 1084-1102.
Leenaars, P.P.A.M. et al., "Increased adjuvant efficacy in stimulation of antibody responses after macrophage elimination in vivo." *Immunology* vol. 90 (1997). 337-343.
Lehenkari, Petri P. et al., "Further Insight into Mechanism of Action of Clodronate: Inhibition of Mitochondrial ADP/ATP Translocase by a Nonhydrolyzable, Adenine-Containing Metabolite." *Molecular Pharmacology* vol. 62 (2002). 1255-1262.

(Continued)

*Primary Examiner* — Yunsoo Kim
(74) *Attorney, Agent, or Firm* — McCarter & English, LLP; Maria Laccotripe Zacharakis; Deborah L. Nagle

(57) ABSTRACT

The present invention demonstrates that bisphosphonates have an intrinsic adjuvant activity and directly stimulate B cell antibody secretion. Accordingly, the present invention provides vaccines comprising a bisphosphonate, methods for stimulating an immune response, enhancing the immunogenicicty of an immunogen, and methods of treating an infection, an autoimmune disease, an allergy, and/or a cancer using the same.

20 Claims, 16 Drawing Sheets

(56) References Cited

OTHER PUBLICATIONS

Licata, Angelo A. "Discovery, Clinical Development, and Therapeutic Uses of Bisphosphonates." *The Annuals of Pharmacotherapy* vol. 39 (2005). 668-677.
Poli, Gianluigi et al., "A tolerability and pharmacokinetic study of a new injectable formulation of disodium clodronate in healthy female volunteers." *European Journal of Drug Metabolism and Pharmacokinetics* vol. 29, No. 2 (2004). 145-152.
Purtha, Whitney E. et al., "Early B-Cell Activation after West Nile Virus Infection Requires Alpha/Beta Interferon but Not Antigen Receptor Signaling." *Journal of Virology* vol. 82, No. 22 (2008). 10964-10974.
Tucci et al., "Effect of three years of oral alendronate treatment in postmenopausal women with osteoporosis.", Am J Med 1996, 101:488-501.
Poccia et al., "Zoledronic acid and interleukin-2 treatment improves immunocompetence in HIV-infected persons by activating Vgamma9Vdelta2 T cells.", AIDS 2009, 23(5):555-65.
Sauty et al., "Interleukin-6 and tumor necrosis factor α levels after bisphosphonates treatment in vitro and in patients with malignancy", Bone. 1996, 18(2):133-9.
Van Rooijen and van Nieuwmegen, "Elimination of phagocytic cells in the spleen after intravenous injection of liposome-encapsulated dichloromethylene diphosphonate", Cell Tissue (1984) vol. 238 (2) pp. 355-8.
Kunzmann et al. "Stimulation of gammadelta T cells by aminobisphosphonates and induction of antiplasma cell activity in multiple myeloma", Blood (2000) vol. 96 (2) pp. 384-392.
Thompson et al., "Statins prevent bisphosphonate-induced gamma,delta-T-cell proliferation and activation in vitro.", J. Bone Miner. Res. 19 (2004) pp. 278-288.
Miyagawa et al., "Essential Requirement of Antigen Presentation by Monocyte Lineage Cells for the Activation of Primary Human ?d T Cells by Aminobisphosphonate Antigen", J Immunol (2001) vol. 166 (9) pp. 5508-1.
Zhao et al., "Evasion by Stealth: Inefficient Immune Activation Underlies Poor T Cell Response and Severe Disease in SARS-CoV-Infected Mice", PLoS Pathog (2009) 5(10): e1000636.

\* cited by examiner

VACCINES COMPRISING BISPHOSPHONATE AND METHODS OF USE THEREOF

RELATED APPLICATIONS

This application is a 35 U.S.C. § 371 national stage filing of International Application No. PCT/US2011/057224, filed Oct. 21, 2011, completed, which claims priority to U.S. Provisional Application No. 61/405,777, filed on Oct. 22, 2010, the entire contents of each of which are incorporated herein by this reference.

STATEMENT REGARDING FEDERALLY SPONSORED RESEARCH OR DEVELOPMENT

This invention was made with Government support under grant number 5PO1AI078897-02, awarded by the National Institutes of Health. The government, therefore, has certain rights in the invention.

BACKGROUND OF THE INVENTION

Vaccine adjuvants are one of many components included in vaccines to enhance immune response to the presented antigen in order to, for example, decrease the time before acquisition of immunity following vaccination, increase the potency/time-span of acquired immunity, and/or decrease the amount of antigen required for protection. Adjuvants have been used since the early 20th Century to enhance an immune response to an antigen. The need for adjuvants as components of vaccines is acute, as newer antigens are weak immunogens or have limited availability. There is currently only one adjuvant approved for use in human vaccines in the U.S. That adjuvant, alum salts, poses little safety risk, but provides only a modest increase in adaptive immune response in many contexts.

Accordingly, there is a need in the art for adjuvants capable of increasing adaptive immune responses, as well as for highly immunogenic, effective vaccines which contain these adjuvants.

SUMMARY OF THE INVENTION

The present invention is based, at least in part, on the discovery that bisphosphonates have an intrinsic adjuvant activity. In particular, it has been found that although administration of bisphosphonate-encapsulated liposomes to non-human animals results in depletion of macrophages, subsequent administration to such animals of an immunogen unexpectedly led to the development of an increased antigen-specific antibody response. This effect was not the result of depletion of macrophages as other compounds that result in local depletion of lymph node macrophages failed to induce an increase in adaptive immune responses following immunization. In addition, this effect was observed when free bisphosphonate (i.e., not encapsulated in liposomes) was administered to non-human animals. It has also been discovered that liposome-encapsulated bisphosphonate treatment of non-human animals increases dendritic cell migration from the site of injection to the local draining lymph nodes, thereby increasing the antigen availability for presentation to T and B cells. Additionally, it has been discovered that bisphosphonates directly stimulate B cell antibody secretion. It has further been surprisingly discovered that administration to a subject of a commercially available hepatitis B adult vaccine (e.g., Engerix B®) and free bisphosphonate increases antibody responses to the antigen present in the vaccine as compared to administration of the vaccine alone.

Accordingly, the present invention provides vaccines containing bisphosphonates, as well as methods for stimulating an immune response, enhancing immunogenicity of an immunogen, and methods of treating an infection, an autoimmune disease, an allergy, and/or a cancer using the same.

In one aspect, the invention provides vaccines which include a bisphosphonate and a pharmaceutically acceptable carrier.

The vaccines of the invention may be administered intramuscularly, subcutaneously, intradermally, intranasally, orally, transcutaneously, or mucosally. In another embodiment, a vaccine of the invention is not administered orally.

In one embodiment, the vaccines further comprise at least one immunogen.

In one embodiment, the at least one immunogen is present in a commercially available vaccine. In one embodiment, the commercially available vaccine comprises at least one additional adjuvant. In one embodiment, the at least one additional adjuvant is alum.

In another aspect, the invention provides a vaccine comprising a bisphosphonate and a commercially available vaccine, e.g., comprising at least one immunogen and an adjuvant.

In one embodiment, the commercially available vaccine for use in the vaccines and methods of the invention has been approved by a regulatory agency, such as, for example, the United States Food and Drug Administration (FDA), the United States Department of Agriculture (USDA), the European Medicines Agency (EMA), the Japanese Ministry of Health and Welfare (MHW), the Therapeutic Goods Administration of Australia, the State Food and Drug Administration (SFDA) (China), the Health Protection Branch of Canada, and the Veterinary Drugs Directorate (VDD) in Canada.

The vaccines suitable for use in the vaccines and methods of the invention include, for example, vaccines suitable for human and veterinary administration, such as anti-viral vaccines, anti-bacterial vaccines, anti-parasite vaccines, and non-infectious disease vaccines.

In another aspect, the present invention provides methods for stimulating an immune response in a subject. The methods include administering to the subject a bisphosphonate in an amount effective to stimulate an immune response in the subject, thereby stimulating the immune response in the subject. In one embodiment, the methods further include administering to the subject at least one immunogen. In one embodiment, the at least one immunogen may be a component of a commercially available vaccine. In one embodiment, the commercially available vaccine comprises at least one additional adjuvant. In one embodiment, the at least one additional adjuvant is alum. In one embodiment, the methods further include administering a commercially available vaccine to the subject.

In yet another aspect, the present invention provides methods for stimulating an immune response to at least one immunogen in a subject. The methods include administering to the subject a bisphosphonate in an amount effective to stimulate an immune response to the at least one immunogen in the subject, thereby stimulating the an immune response to the at least one immunogen in the subject. In one embodiment, the at least one immunogen is a component of a commercially available vaccine. In one embodiment, the commercially available vaccine comprises at least one additional adjuvant. In one embodiment, the at least one additional adjuvant is alum. In one embodiment, the methods further include administering a commercially available vaccine to the subject.

In another aspect of the invention, methods for enhancing the immunogenicity of at least one immunogen in a subject are provided. The methods include administering to the subject the at least one immunogen and a bisphosphonate in an amount effective to induce an immune response to the at least one immunogen in the subject, thereby enhancing the immunogenicity of the at least one immunogen in the subject. In one embodiment, the at least one immunogen is a component of a commercially available vaccine. In one embodiment, the commercially available vaccine comprises at least one additional adjuvant. In one embodiment, the at least one additional adjuvant is alum. In one embodiment, the methods further include administering a commercially available vaccine to the subject.

In yet another aspect of the invention, methods for directly stimulating B cells to produce an antibody to at least one immunogen are provided. The methods include contacting a population of naïve B cells with an immunogen and a bisphosphonate, thereby directly stimulating the B cells to produce the antibody to at least one immunogen. In one embodiment, the at least one immunogen is a component of a commercially available vaccine. In one embodiment, the commercially available vaccine comprises at least one additional adjuvant. In one embodiment, the at least one additional adjuvant is alum. In one embodiment, the methods further include contacting the population of naïve B cells with a commercially available vaccine. The step of contacting may be performed in vivo or in vitro.

Administration of the bisphosphonate to the subject may be intramuscularly, subcutaneously, intradermally, intranasally, orally, transcutaneously, or mucosally. In another embodiment, administration of the bisphosphonate to the subject is not orally.

In one embodiment of the methods of the invention, the bisphosphonate is provided in a pharmaceutically acceptable carrier.

In one embodiment of the methods of the invention, the at least one immunogen and the bisphosphonate are combined with a pharmaceutically effective carrier.

In one embodiment, the at least one immunogen and the bisphosphonate combined with a pharmaceutically acceptable carrier are further combined with at least one additional adjuvant, such as an inorganic adjuvant, an organic adjuvant, an oil-based adjuvant (e.g., Freund's Complete Adjuvant, MF59 (Novartis)), a bacterially-derived adjuvant, a TLR-dependent adjuvant, a virisome, a virus-like particle, QS21, an agent that activates an inflammasome, an attenuated or killed intact microbe and microbial lysates, or fragments thereof, a nanoparticle, an agent that induces or mimics CD40L, topical exposure of skin to low-frequency ultrasound with SDS, an injected ex vivo modified APC, a liposome, and an ISCOM. In one embodiment, the adjuvant is alum.

In one embodiment, the methods of the invention comprise repeating the administration to the subject of the at least one immunogen and the bisphosphonate.

In one embodiment, the bisphosphonate and the immunogen are administered simultaneously.

In one embodiment, the bisphosphonate is administered prior to administration of the immunogen.

In another embodiment, the bisphosphonate is administered after administration of the immunogen.

In one embodiment, the methods of the invention comprise repeating the administration to the subject of the commercially available vaccine and the bisphosphonate.

In one embodiment, the commercially available vaccine and the bisphosphonate are administered simultaneously.

In one embodiment, the commercially available vaccine is administered prior to the bisphosphonate.

In another embodiment, the commercially available vaccine is administered after the bisphosphonate.

In one embodiment, the at least one immunogen and the bisphosphonate are administered in a single formulation.

In one embodiment, the commercially available vaccine, e.g., comprising at least one immunogen and/or at least one additional adjuvant, and the bisphosphonate are administered in a single formulation. In another embodiment, the commercially available vaccine, e.g., comprising at least one immunogen and/or at least one additional adjuvant, and the bisphosphonate are administered in separate formulations.

In one embodiment, the bisphosphonate is free bisphosphonate and is not provided as a component of a particle delivery system.

In one embodiment of the methods of the invention, migration of dendritic cells (DCs), such as plasmacytoid DCs, myeloid DCs, Langerhans cells, dermal DCs, monocyte-derived DCs, to a local lymph node is increased.

In another embodiment of the methods of the invention, T cell activation, such as CD4+, CD8+, and gamma delta T cell activation, in the subject is increased.

In yet another embodiment of the methods of the invention, NKT and NK cell activation in said subject is increased.

In one embodiment of the methods of the invention, the subject exhibits a higher titer of immunogen-specific antibodies, such as IgG, IgM, IgA, IgD and IgE antibodies, and/or larger numbers of immunogen-specific effector/memory T cells relative to a subject not administered the bisphosphonate and the at least one immunogen.

In one embodiment, the methods of the invention are independent of Toll-like receptor signaling.

In one embodiment, the methods of the invention are independent of macrophage depletion.

In one aspect, the present invention provides methods for treating a subject having an infection. The methods include administering to a subject having an infection a bisphosphonate, thereby treating the infection. The methods may further comprise administering to the subject at least one immunogen associated with the infection. In one embodiment, the at least one immunogen is a component of a commercially available vaccine. In one embodiment, the commercially available vaccine comprises at least one additional adjuvant. In one embodiment, the at least one additional adjuvant is alum. In one embodiment, the methods further include administering a commercially available vaccine to the subject.

In one embodiment of the methods of the invention, the bisphosphonate is provided in a pharmaceutically acceptable carrier.

In one embodiment, the at least one immunogen and the bisphosphonate are combined with a pharmaceutically effective carrier.

In certain embodiments, the immunogen is administered to the subject in an immunogenically effective amount. In other embodiments, the bisphosphonate is administered to the subject in an immunogenically effective amount. In one embodiment, the infection is selected from the group consisting of viral infection, bacterial infection, parasitic infection, and fungal infection.

In another aspect, the present invention provides methods for treating a subject having cancer. The methods include administering to a subject having a cancer a bisphosphonate, thereby treating the cancer. The methods may further comprise administering to the subject at least one immunogen associated with the cancer. In one embodiment, the at least one immunogen is a component of a commercially available vaccine. In one embodiment, the commercially available vaccine comprises at least one additional adjuvant. In one embodiment, the at least one additional adjuvant is alum. In one embodiment, the methods further include administering a commercially available vaccine to the subject.

In one embodiment of the methods of the invention, the bisphosphonate is provided in a pharmaceutically acceptable carrier. In one embodiment, the at least one immunogen and the bisphosphonate are combined with a pharmaceutically effective carrier.

In certain embodiments, the immunogen is administered to the subject in an immunogenically effective amount. In other embodiments, the bisphosphonate is administered to the subject in an immunogenically effective amount. In one embodiment, the cancer is selected from the group consisting of prostrate, breast, colorectal, lung, pancreatic, renal, and melanoma cancer.

In one embodiment, the bisphosphonate for use in the vaccines and methods of the invention is selected from compounds of formula (I-A):

(IA)

and pharmaceutically acceptable salts thereof;

wherein R1 is selected from hydrogen, halogen, hydroxy, amine and thio; and

R2 is selected from hydrogen, halogen, hydroxy, thio, amino, SR3, NR4R5 and C1-6 alkyl substituted with 0 or 1 NR6R7, thio, aryl or heteroaryl;

R3 is selected from hydrogen, C1-6 alkyl, C5-7 aryl and C5-7 haloaryl; and each R4, R5, R6 and R7 are each individually selected from hydrogen, C1-6 alkyl and C5-7 aryl.

In one embodiment, R1 is selected from hydrogen, halogen and hydroxy.

In one embodiment, R2 is selected from halogen, SR3, NR4R5 and C1-6 alkyl substituted with 0 or 1 substituents selected from NR6R7, aryl and heteroaryl.

In one embodiment, R3 is selected from C5-7 aryl and C5-7 haloaryl.

In one embodiment, each R4, R5, R6 and R7 are each individually selected from hydrogen and C1-6 alkyl.

In one embodiment, the bisphosphonate for use in the methods and vaccines of the present invention is selected from the group consisting of Etidronate, Clodronate, Pamidronate, Alendronate, Neridronate, Incadronate, Olpadronate, Ibandronate, Risedronate, and Zoledronate. In one embodiment, the bisphosphonate is provided as a component of a particle delivery system. In another embodiment, the bisphosphonate is free bisphosphonate and is not provided as a component of a particle delivery system.

In one embodiment, the bisphosphonate is provided as a component of the particle delivery system is encapsulated, embedded, or adsorbed within a particle, dispersed in a particle matrix, adsorbed on or linked to a particle surface, or a combination of any of these forms.

In one embodiment, the particle delivery system is selected from the group consisting of a surfactant-based emulsion, a lipid-based particle, a small unilamellar vesicle, a microparticle, a microsphere, a microcapsule, a nanocapsule, a nanoparticle, a metallic nanoparticle, a picoparticle, a dendrimer, a buckyball, a nanowire, and a virus-like particle.

In one embodiment, the bisphosphonate provided as a component of the particle delivery system is suitable for administration to a human subject.

In another embodiment, the bisphosphonate is free bisphosphonate and is not provided as a component of a particle delivery system is suitable for administration to a non-human subject.

In certain embodiments of the vaccines and methods of the invention, the immunogen is an infectious agent, such as an inactivated infectious agent, or an infectious agent product.

An immunogen for use in the vaccines and methods of the invention may be selected from the group consisting of virus, bacteria, parasite, protozoan, and fungus, products derived from the virus, bacteria, parasite, protozoan, and fungus, a cancer antigen, a degenerative disease antigen, an atopic disease antigen, an autoimmune disease antigen, an alloantigen, a xenoantigen, a metabolic disease enzyme or enzymatic product, a recombinantly produced protein or peptide, a chimeric fusion protein, and a small molecule. In one embodiment, the at least one immunogen is a component of a commercially available vaccine. In one embodiment, the commercially available vaccine comprises at least one additional adjuvant. In one embodiment, the at least one additional adjuvant is alum.

In one embodiment, the virus is selected from the group consisting of a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

In one embodiment, the bacteria is selected from the group consisting of *Borrelia* species, *Bacillus anthracis*, *Borrelia burgdorferi*, *Bordetella pertussis*, *Camphylobacter jejuni*, *Chlamydia* species, *Chlamydial psittaci*, *Chlamydial trachomatis*, *Clostridium* species, *Clostridium tetani*, *Clostridium botulinum*, *Clostridium perfringens*, *Corynebacterium diphtheriae*, *Coxiella* species, an *Enterococcus* species, *Erlichia* species, *Escherichia coli*, *Francisella tularensis*, *Haemophilus* species, *Haemophilus influenzae*, *Haemophilus parainfluenzae*, *Lactobacillus* species, a *Legionella* species, *Legionella pneumophila*, *Leptospirosis interrogans*, *Listeria* species, *Listeria monocytogenes*, *Mycobacterium* species, *Mycobacterium tuberculosis*, *Mycobacterium leprae*, *Mycoplasma* species, *Mycoplasma pneumoniae*, *Neisseria* species, *Neisseria meningitidis*, *Neisseria gonorrhoeae*, *Pneumococcus* species, *Pseudomonas* species, *Pseudomonas aeruginosa*, *Salmonella* species, *Salmonella typhi*, *Salmonella enterica*, *Rickettsia* species, *Rickettsia ricketsii*, *Rickettsia typhi*, *Shigella* species, Staphylococcus species, Staphylococcus aureus, Streptococcus species, Streptocccus pnuemoniae, Streptococcus pyrogenes, Streptococcus mutans, Treponema species, Treponema pallidum, a Vibrio species, Vibrio cholerae, Yersinia pestis.

In one embodiment, the fungus is selected from the group consisting of Aspergillus species, Candida species, Candida albicans, Candida tropicalis, Cryptococcus species, Cryptococcus neoformans, Entamoeba histolytica, Histoplasma capsulatum, Leishmania species, Nocardia asteroides, Plasmodium falciparum, Toxoplasma gondii, Trichomonas vaginalis, Toxoplasma species, Trypanosoma brucei, Schistosoma mansoni, Fusarium species, and Trichophyton species.

In one embodiment, the parasite is selected from the group consisting of Plasmodium species, Toxoplasma species, Entamoeba species, Babesia species, Trypanosoma species, Leshmania species, Pneumocystis species, Trichomonas species, Giardia species, and Schisostoma species.

In one embodiment, the protozoan is selected from the group consisting of Cryptosporidium species, Plasmodium species, Entamoeba species, Naegleria species, Acanthamoeba species, Balamuthia species, Toxoplasma species, Giardia species, Trichomonas species, Leishmania species, and Trypanosoma species.

In one embodiment, the cancer antigen is selected from the group consisting of Melan-A/MART-1, Dipeptidyl peptidase IV (DPPIV), adenosine deaminase-binding protein (AD Abp), cyclophilin b, Colorectal associated antigen (CRC)-C017-1A/GA733, Carcinoembryonic Antigen (CEA), Prostate Specific Antigen (PSA), prostate-specific membrane antigen (PSMA), T-cell receptor/CD3-zeta chain, MAGE-family of tumor antigens, GAGE-family of tumor antigens, BAGE, RAGE, LAGE-I, NAG, GnT-V, MUM-I, CDK4, tyrosinase, p53, MUC family, HER2/neu, p21ras, RCAS1, α-fetoprotein, E-cadherin, α-catenin, β-catenin and γ-catenin, p120ctn, gp100Pmel117, PRAME, NY-ESO-I, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, HA, Connexin 37, Ig-idiotype, p15, gp75, GM2 and GD2 gangliosides, viral products, Smad family of tumor antigens, lmp-1, EBV-encoded nuclear antigen (EBNA)-I, UL16-binding protein-like transcript 1 (Mult1), RAE-1 proteins, H60, MICA, MICB, and c-erbB-2.

Other features and advantages of the invention will be apparent from the following detailed description and claims.

DETAILED DESCRIPTION OF THE INVENTION

Figure 1:
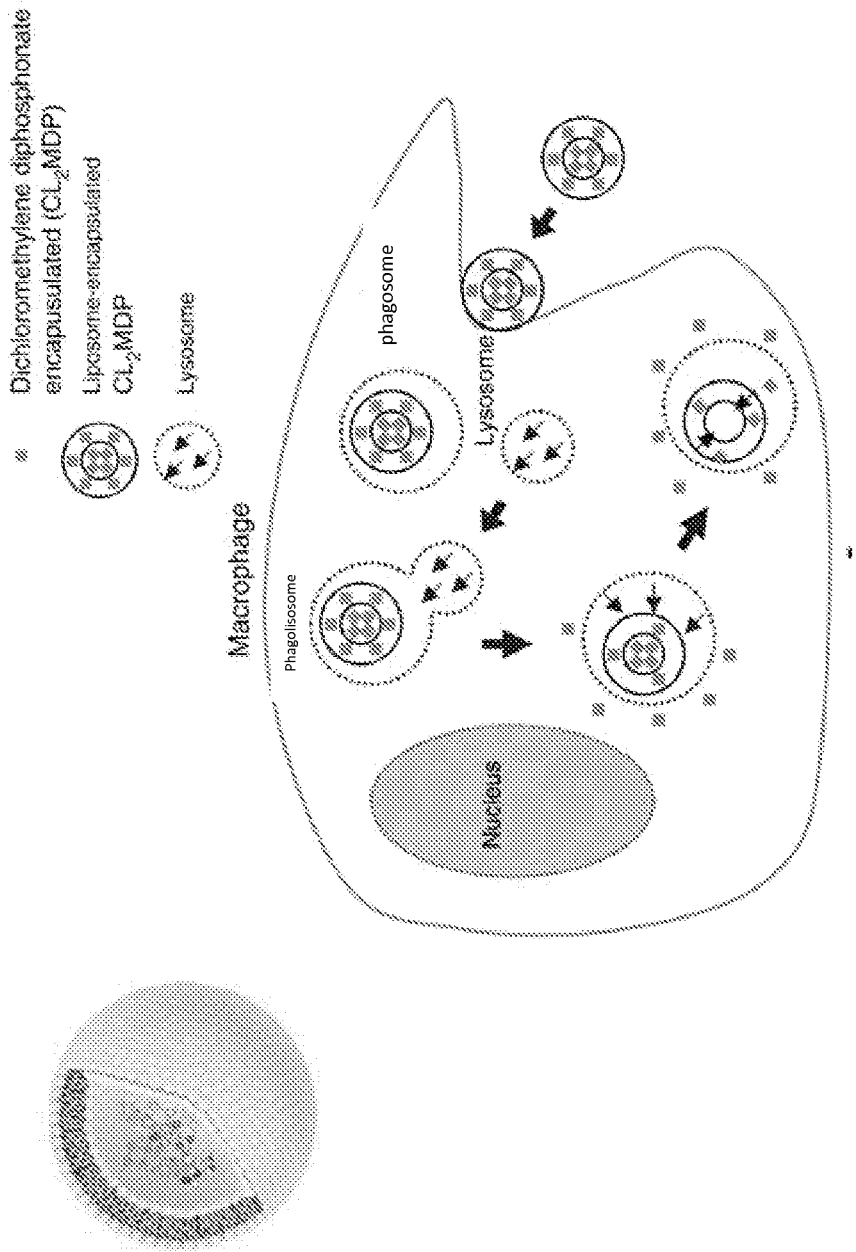
FIG. 1 depicts the mechanism of macrophage depletion by clodronate liposomes (CLL), i.e., liposome-encapsulated dichloromethylene diphosphonate ($Cl_2MDP$).

The present invention is based, at least in part, on the discovery that bisphosphonates have an intrinsic adjuvant activity. In particular, it has been found that although administration of bisphosphonate-encapsulated liposomes to non-human animals depletes macrophages, subsequent administration to such animals of an immunogen unexpectedly led to the development of an increased antigen-specific antibody response. This effect was not the result of depletion of macrophages (e.g., attenuation of inflammatory cytokine expression and/or activity) as other compounds that result in local depletion of lymph node macrophages failed to induce an increase in adaptive immune responses following immunization. In addition, this effect was observed when free bisphosphonate (i.e., not encapsulated in liposomes) was administered to non-human animals. It has also been discovered that liposome-encapsulated bisphosphonate treatment of non-human animals increases dendritic cell migration from the site of injection to the local draining lymph nodes, thereby increasing the antigen availability for presentation to T and B cells. Additionally, it has been discovered that bisphosphonates directly stimulate B cell antibody secretion. It has further been surprisingly discovered that administration to a subject of a commercially available hepatitis B adult vaccine (i.e., Engerix B®) and free bisphosphonate increases antibody responses to the antigen present in the vaccine as compared to administration of the vaccine alone.

Accordingly, the present invention provides vaccines containing bisphosphonates, as well as methods for stimulating an immune response, enhancing immunogenicity of an immunogen, and methods of treating an infection, an autoimmune disease, an allergy, and/or a cancer using the same.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element.

As used herein, the term "adjuvant" refers to an agent (e.g., a bisphosphonate) that stimulates and/or enhances an immune response in a subject. An adjuvant can stimulate and/or enhance an immune response in the absence of an immunogen and/or can stimulate and/or enhance an immune response in the presence of an immunogen. In the present invention, a preferred adjuvant is a bisphosphonate.

As used herein, the term "bisphosphonate" includes analogs of pyrophosphates that contain two phosphonate groups attached to (typically one) central carbon that replaces the oxygen in pyrophosphate. Bisphosphonates are described extensively in Section III, below.

As used herein, the term "immunogen" refers to an antigen that is recognized as unwanted, undesired, and/or foreign in a subject.

A used herein, the term "immune response" includes a response by a subject's immune system to a vaccine of the invention. Immune responses include both cell-mediated immune responses (responses mediated by antigen-specific T cells and non-specific cells of the immune system) and humoral immune responses (responses mediated by antibodies present in the plasma lymph, and tissue fluids). The term "immune response" encompasses both the initial responses to an immunogen as well as memory responses that are a result of "acquired immunity."

As used herein, the phrase "stimulating an immune response" refers to an increase in an immune response in the subject following administration of a vaccine of the present invention relative to the level of immune response in the subject when a vaccine of the present invention has not been administered. As used herein, the term "vaccine" refers to a composition that elicits an endogenous immune response in a subject (e.g., a human or animal). The endogenous immune response may result in, for example, the switching of a Th1 biased immune response to a Th2 biased immune response, the activation or enhancement of T effector cell responses and/or the reduction of T regulatory cell response, the activation of antigen-specific naive lymphocytes that may then give rise to antibody-secreting B cells or antigen-specific effector and memory T cells or both, and/or the direct activation of antibody-secreting B cells.

As used herein, the phrase "directly stimulating B cells" refers to the ability of a vaccine of the invention to stimulate antibody production by naïve B cells in the absence of T cell help, e.g., in the absence of CD4+ T cells.

As used herein, the term "enhanced immunogenicity" refers to an increase in the level of immune response to a given immunogen following administration of a vaccine of the present invention relative to the level of immune response to the immunogen when a vaccine of the present invention has not been administered. The enhanced immunogenicity of an immunogen may direct an enhanced cellular response, and enhanced humoral response, and/or both enhanced cellular an humoral responses.

The term "administering" includes any method of delivery of a pharmaceutical composition or agent into a subject's system or to a particular region in or on a subject. In certain embodiments of the invention, a vaccine is administered intramuscularly, subcutaneously, intradermally, intranasally, orally, transcutaneously, or mucosally. In other embodiments, a vaccine of the invention is not administered orally.

As used herein the term "infectious agent" refers to an organism (e.g., bacterial, fungal, protozoan, parasitic, or viral) that causes disease in another organism (e.g., a subject) by directly infecting the other organism, or by producing agents that cause disease in another organism (e.g., bacteria that produce pathogenic toxins).

As used herein, the term "infectious agent product" refers to any component or product derived from an infectious agent including, but not limited to, polypeptides, peptides, proteins, nucleic acids, membrane fractions, and polysaccharides.

As used herein the term "microorganism" refers to microscopic organisms and taxonomically related macroscopic organisms within the categories of algae, bacteria, fungi (including lichens), protozoa, parasites, viruses, and subviral agents. The term microorganism encompasses both those organisms that are in and of themselves infectious and/or pathogenic to another organism (e.g., a subject) and those organisms that produce agents that are pathogenic to another organism, while the organism itself is not directly pathogenic or infective to the other organism.

As used herein the term "disease" refers to a deviation from the condition regarded as normal or average for a subject, and which is detrimental to a subject under conditions that are not inimical to the majority of subjects of the same species or group (e.g., diarrhea, nausea, fever, pain, infection, cancer, autoimmune disease, allergy, metabolic disease, and inflammation). A disease may be caused by or result from contact with an external agent, e.g., an infectious agent and/or infectious agent product, or an internal agent, e.g., cancer and autoimmune disease.

The term "subject" as used herein, refers to organisms to be administered the vaccines and/or treated by the methods of the present invention. A subject includes an organism that is exposed to, suspected of being exposed to, and/or at risk of being exposed to one or more infectious agents. A subject also includes organisms to be treated so as to prevent undesired exposure to infectious agents. Furthermore, a subject includes organisms having an ineffective or inappropriate endogenous immune response resulting in disease, for example allergy, asthma, autoimmune disease, metabolic disease, and/or cancer. Organisms include but are not limited to animals (e.g., humans, domesticated animals, e.g., livestock and pets, e.g., cat, dog, goat, cow, pig, chicken, and wild animals). In one embodiment of the invention, a subject is human, such as a human in need of vaccination, e.g., a child or adult human subject in a pandemic/epidemic setting. In one embodiment, the subject is a non-human animal. In one embodiment of the invention, the subject, i.e., the non-human animal, is not a rodent, e.g., not a mouse nor a rat.

An "immunogenically effective amount" is that amount sufficient to treat a disease and/or affect an endogenous immune response in a subject. An immunogenically effective amount can be administered in one or more administrations.

As used herein, the terms "treating" or "treatment" refer to a beneficial or desired clinical result including, but not limited to, alleviation or amelioration of one or more symptoms, diminishing the extent of infection, stabilized (i.e., not worsening) state of infection, amelioration or palliation of the infectious state, and remission (whether partial or total), whether detectable or undetectable. "Treatment" can also mean prolonging survival as compared to expected survival in the absence of treatment.

As used herein, the term "Toll" is the *Drosophila* gene essential for ontogenesis and anti-microbial resistance. Vertebrate orthologues of Toll have been identified and cloned in vertebrates and are referred to as "Toll-like receptors" ("TLRs"). "TLRs" are transmembrane proteins characterized structurally by a cytoplasmic Toll/interleukin-1 receptor (TIR) domain and by extracellular leucine-rich repeats. TLRs detect and are activated by invading pathogens and binding conserved, microbially derived molecules and that induce signaling cascades for proinflammatory gene expression.

As used herein, the terms "Toll-like receptor signaling" and "TLR-signaling" refer to the propagation of an intracellular signal by activated TLRs. When activated, TLRs recruit adapter molecules within the cytoplasm of cells in order to propagate the signal. Four adapter molecules are known to be involved in signaling. These proteins are known as MyD88, Tirap (also called Mal), Trif, and Tram. The adapters activate other molecules within the cell, including certain protein kinases (IRAK1, IRAK4, TBK1, and IKKi) that amplify the signal, and ultimately lead to the induction or suppression of genes that orchestrate the inflammatory response. Signaling through a TLR leads not only to the induction of inflammatory responses but also to the development of antigen-specific adaptive immunity. The TLR-induced inflammatory response is dependent on a common signaling pathway that is mediated by the adaptor molecule MyD88. (For a review, see, e.g., West, A. P., et al. (2006) *Ann Rev Cell and Develop Biol* 22: 409-437). One of ordinary skill in the art can readily determine if TLR signaling has been activated by determining the expression and/or activity of MyD88, Tirap, Trif, Tram, IRAK1, IRAK4, TBK1, and IKKi using methods known in the art, such as RT-PCR. As described in the appended examples, TLR signaling is not involved in the intrinsic adjuvant activity of a bisphosphonate. Accordingly, in one embodiment of the invention, the vaccines and methods of the invention are independent of Toll-like receptor signaling.

II. Vaccines of the Invention

In one aspect of the invention, vaccines comprising a bisphosphonate are provided. As described in the appended examples, it has been discovered that bisphosphonates have an intrinsic adjuvant activity which is not the result of macrophage depletion and/or encapsulation in a liposome, and is independent of Toll-like receptor (TLR) signaling. In one embodiment, the vaccines of the invention further comprise at least one immunogen. The at least one immunogen can be a component of a commercially available vaccine, such as a commercially available vaccine comprising at least one additional adjuvant, e.g., alum. A commercially available vaccine and a bisphosphonate can be administered either separately (e.g., the commercially available vaccine can be administered before or after the bisphosphonate is administered to the subject) or as a single formulation (e.g., the commercially available vaccine can be administered simultaneously with the bisphosphonate).

As described in the examples section below, it has been discovered that administration of a commercially available vaccine and a bisphosphonate increases the rate at which neutralizing antibodies are produced, increases the neutralizing antibody titers and increases the number of antibody producing B cells as compared to the administration of the commercially available vaccine alone. Therefore, a vaccine comprising a commercially available vaccine and a bisphosphonate stimulates greater protection against the antigen in the commercially available vaccine in a shorter period of time as compared to the vaccine alone thereby allowing use of smaller doses of the commercially available vaccine to achieve protective antibody titers. This effect is particularly useful during an epidemic and/or pandemic in which there is a shortage of vaccines. In addition, both a bisphosphonate and a commercially available vaccine have previously been approved by a regulatory agency and are well-tolerated. Furthermore, the use of a commercially available vaccine and a bisphosphonate in the vaccines and methods of the invention do not require re-formulation of the commercially available vaccine.

The immunogens used to prepare the vaccines of the invention may be derived from a wide variety of sources. For example, suitable immunogens may include an infectious agent (e.g., bacterial, fungal, protozoan, parasitic, or viral), an infectious agent-derived product, e.g., protein, peptide, nucleic acid, polysaccharide, glycoprotein, glycolipid, antigen or antigenic preparations, a cancer antigen (e.g., a tumor associated antigen (TAA)), a degenerative disease antigen, an atopic disease antigen, an autoimmune disease antigen, an alloantigen, a xenoantigen, a metabolic disease enzyme or enzymatic product, a recombinantly produced protein or peptide, a chimeric fusion protein, and/or a small molecule.

Suitable immunogens may be in the form of whole cells or purified or partially purified antigens or antigenic preparations. Suitable immunogens may be used without modification, in galenic form, or in combination with vehicles or carriers such as e.g. microspheres, liposomes, nanospheres, and other antigen delivery systems familiar to one of ordinary skill in the art.

In one embodiment, a suitable immunogen is an infectious agent, or a product of an infectious agent. In one embodiment, the immunogen comprises an inactivated infectious agent, e.g., that has been killed or otherwise attenuated. In another embodiment, the immunogen comprises a live infectious agent.

In one embodiment, the infectious agent (or infectious agent product) is a virus, for example and without limitation, a pox virus (e.g., vaccinia virus), smallpox virus, marburg virus, flaviviruses (e.g. Yellow Fever Virus, Dengue Virus, Tick-borne encephalitis virus, Japanese Encephalitis Virus), influenza virus (or antigens, such as F and G proteins or derivatives thereof), e.g., influenza A; or purified or recombinant proteins thereof, such as HA, NP, NA, or M proteins, or combinations thereof), parainfluenza virus (e.g., sendai virus), respiratory syncytial virus, rubeola virus, human immunodeficiency virus (or antigens, e.g., such as tat, nef, gp120 or gp160), human papillomavirus (or antigens, such as HPV6, 11, 16, 18), varicella-zoster virus (or antigens such as gpI, II and 1E63), herpes simplex virus (e.g., herpes simplex virus I, herpes simplex virus II; or antigens, e.g., such as gD or derivatives thereof or Immediate Early protein such as ICP27 from HSV1 or HSV2), cytomegalovirus (or antigens such as gB or derivatives thereof), Epstein-Barr virus (or antigens, such as gp350 or derivatives thereof), JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, hantavirus, junin virion, filovirus (e.g., ebola virus), coxsackievirus, equine encephalitis virus, Rift Valley fever virus, alphavirus (e.g., Chikungunyavirus, sindbis virus), hepatitis A virus, hepatitis B virus (or antigens thereof, for example Hepatitis B Surface antigen or a derivative thereof), hepatitis C virus, hepatitis D virus, or hepatitis E virus.

In one embodiment, the infectious agent is a bacterium which may be in vegetative or spore form, or a bacterially derived product. Non-limiting examples of suitable bacteria (or bacterially derived products) for use in the vaccines and/or methods of the invention include *Neisseria* species, including *N. gonorrhea* and *N. meningitidis* (or antigens, such as, for example, capsular polysaccharides and conjugates thereof, transferrin-binding proteins, lactoferrin binding proteins, PilC, adhesins); *Haemophilus* species, e.g., *H. influenzae*; *S. pyogenes* (or antigens, such as, for example, M proteins or fragments thereof, C5A protease, lipoteichoic acids), *S. agalactiae, S. mutans; H. ducreyi; Moraxella* spp, including *M. catarrhalis*, also known as *Branhamella catarrhalis* (or antigens, such as, for example, high and low molecular weight adhesins and invasins); *Bordetella* spp, including *B. pertussis* (or antigens, such as, for example, pertactin, pertussis toxin or derivatives thereof, filamenteous hemagglutinin, adenylate cyclase, fimbriae), *B. parapertussis* and *B. bronchiseptica; Mycobacterium* species, including *M. tuberculosis* (or antigens, such as, for example, ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (or antigens, such as, for example, colonization factors, heat-labile toxin or derivatives thereof, heat-stable toxin or derivatives thereof), enterohemorragic *E. coli*, enteropathogenic *E. coli* (or antigens, such as, for example, shiga toxin-like toxin or derivatives thereof); *Vibrio* spp, including *V. cholera* (or antigens, such as, for example, cholera toxin or derivatives thereof); *Shigella* spp, including *S. sonnei, S. dysenteriae*, S. flexnerii; *Yersinia* spp, including *Y. enterocolitica* (or antigens, such as, for example, a Yop protein), *Y. pestis, Y. pseudotuberculosis; Campylobacter* spp, including *C. jejuni* (or antigens, such as, for example, toxins, adhesins and invasins) and *C. coli; Salmonella* spp, including *S. typhi, S. paratyphi, S. choleraesuis, S. enteritidis, S. typhimurium*, and *S. dysenteriae; Listeria* species, including *L. monocytogenes; Helicobacter* spp, including *H. pylori* (for example urease, catalase, vacuolating toxin); *Pseudomonas* spp, including *P. aeruginosa; Staphylococcus* species, including *S. aureus, S. epidermidis; Proteus* species, e.g., *P. mirabilis; Enterococcus* species, including *E. faecalis, E. faecium; Clostridium* species, including *C. tetani* (or antigens, such as, for example, tetanus toxin and derivative thereof), *C. botulinum* (or antigens, such as, for example, botulinum toxin and derivative thereof), *C. difficile* (or antigens, such as, for example, *clostridium* toxins A or B and derivatives thereof), and *C. perfringens; Bacillus* species, including *B. anthracis* (or antigens, such as, for example, botulinum toxin and derivatives thereof), *B. cereus, B. circulans* and *B. megaterium; Corynebacterium* species, including *C. diphtheriae* (or antigens, such as, for example, diphtheria toxin and derivatives thereof); *Borrelia* species, including *B. burgdorferi* (for example OspA, OspC, DbpA, DbpB), *B. garinii* (or antigens, such as, for example, OspA, OspC, DbpA, DbpB), *B. afzelii* (for example OspA, OspC, DbpA, DbpB), *B. andersonii* (or antigens, such as, for example, OspA, OspC, DbpA, DbpB), *B. hermsii; Ehrlichia* species, including *E. equi* and the agent of the Human Granulocytic Ehrlichiosis; *Rickettsia* spp, including *R. rickettsii; Chlamydia* species, including *C. trachomatis* (or antigens, such as, for example, MOMP, heparin-binding proteins), *C. pneumoniae* (for example MOMP, heparin-binding proteins), *C. psittaci; Leptospira* species, including L. interrogans; *Streptococcus* species, such as *S. pyogenes, S. aglactiae, S. pneumonia; Treponema* species, including *T. pallidum* (or antigens, such as, for example, the rare outer membrane proteins), *T. denticola*, and *T. hyodysenteriae*.

In one embodiment, the infectious agent is a parasite, or a parasite derived product. Non-limiting examples of suitable parasite (or parasite derived products) for use in the vaccines and/or methods of the invention include *Plasmodium* species, including *P. falciparum; Toxoplasma* species, including *T. gondii* (or antigens, such as, for example SAG2, SAG3, Tg34); *Entamoeba* species, including *E. histolytica; Babesia* species, including *B. microti; Trypanosoma* species, including *T. cruzi; Giardia* species, including *G. lamblia; Leshmania* species, including *L. major; Pneumocystis* species, including *P. carinii; Trichomonas* species, including *T. vaginalis*; and *Schisostoma* species, including *S. mansoni*.

In another embodiment, the infectious agent is a fungus, or a fungal derived product. Suitable fungi (or fungal derived products) for use in the vaccines and/or methods of the invention include, without limitation, *Candida* species, including *C. albicans* and *parapsilosis; Cryptococcus* species, including *C. neoformans; Aspergillus fumigates* and *niger, Fusarium* spp, *Trychophyton* spp, *Absidia* species, e.g., *Absidia corymbifera, Ajellomyces* spp, e.g., *Ajellomyces capsulatus, Arthroderma* species, e.g., *Arthroderma benhamiae, Blastomyces* species, e.g., *Blastomyces dermatitidis, Cladophialophora* species, e.g., *Cladophialophora carrionii, Coccidioides* spp, e.g., *Coccidioides immitis, Cryptococcus* spp, e.g., *Cryptococcus neoformans, Cunninghamella* species, *Epidermophyton* species, e.g., *Epidermophyton floccosum, Exophiala* spp, e.g., *Exophiala dermatitidis, Filobasidiella* spp, e.g., *Filobasidiella neoformans, Fonsecaea* spp, e.g., *Fonsecaea pedrosoi, Fusarium* spp, e.g., *Fusarium solani, Geotrichum* spp, e.g., *Geotrichum candidum, Histoplasma* spp, e.g., *Histoplasma capsulatum, Hortaea* spp, e.g., *Hortaea werneckii, Issatschenkia* spp, e.g., *Issatschenkia orientalis, Madurella* spp, e.g., *Madurella grisae, Malassezia* spp, e.g., *Malassezia furfur, Microsporum* spp, e.g., *Microsporum canis, Mucor* spp, e.g., *Mucor circinelloides, Nectria* spp, e.g., *Nectria haematococca, Paecilomyces* spp, e.g., *Paecilomyces variotii, Paracoccidioides* spp, e.g., *Paracoccidioides brasiliensis, Penicillium* spp, e.g., *Penicillium marneffei, Pichia* spp, e.g., *Pichia guilliermondii, Pneumocystis* spp, e.g., *Pneumocystis carinii, Pseudallescheria* spp, e.g., *Pseudallescheria boydii, Rhizopus* spp, e.g., *Rhizopus oryzae, Rhodotorula* spp, e.g., *Rhodotorula rubra, Scedosporium* spp, e.g., *Scedosporium apiospermum, Schizophyllum* spp, e.g., *Schizophyllum commune, Sporothrix* spp, e.g., *Sporothrix schenckii, Trichophyton* spp, e.g., *Trichophyton violaceum*, and *Trichosporon* spp, e.g., *Trichosporon mucoides*.

In another embodiment, the infectious agent is a protozoan, or a protozoan derived product. Suitable protozoans (or protozoan derived products) for use in the vaccines and/or methods of the invention include, without limitation, protests (unicellular or multicellular), e.g., *Plasmodium falciparum*, and helminths, e.g., cestodes, nematodes, and trematodes.

In one embodiment, a suitable immunogen for use in the vaccines and methods of the invention is a cancer antigen. Non-limiting examples of cancer antigens include, Melan-A/MART-1, Dipeptidyl peptidase IV (DPPIV), adenosine deaminase-binding protein (AD Abp), cyclophilin b, Colorectal associated antigen (CRC)-C017-1A/GA733, Carcinoembryonic Antigen (CEA) and its immunogenic epitopes CAP-I and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-I, GAGE-2, GAGE-3, GAGE-4, GAGE-5, GAGE-6, GAGE-7, GAGE-8, GAGE-9), BAGE, RAGE, LAGE-I, NAG, GnT-V, MUM-I, CDK4, tyrosinase, p53, MUC family, HER2/neu, p21ras, RCAS1, α-fetoprotein, E-cadherin, α-catenin, β-catenin and γ-catenin, p120ctn, gp100Pmel117, PRAME, NY-ESO-I, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, HA, Connexin 37, Ig-idiotype, p15, gp75, GM2 and GD2 gangliosides, viral products such as human papilloma virus proteins, Smad family of tumor antigens, imp-1, EBV-encoded nuclear antigen (EBNA)-I, UL16-binding protein-like transcript 1 (Mult1), RAE-1 proteins, H60, MICA, MICB, and c-erbB-2.

In one embodiment, a suitable immunogen for use in the vaccines and methods of the invention is a small molecule, such as an abused substance, an addictive substance, or a toxin, e.g., a chemical weapon and a hazardous environmental agent. Suitable addictive substances for use in the vaccines and methods of the invention include, for example, a narcotic (e.g., an opiod), a hallucinogen, a stimulant, a cough suppressant, a tranquilizer, and a sedative, e.g., a benzodiazepine.

In one embodiment, a suitable immunogen for use in the vaccines and methods of the invention is an alloantigen (a self-antigen), such as a protein or peptide, lipoprotein, lipid, carbohydrate, a nucleic acid, an enzyme, a structural protein, a secreted protein, a cell surface receptor, and a cytokine, e.g., TNF, IFN-γ, IL-1, or IL-6. In one embodiment, the self-antigen is cholesteryl ester transfer protein (CETP), the Aβ protein associated with Alzheimer's, a proteolytic enzyme that processes the pathological form of the Aβ protein, e.g., beta-secretase, LDL associated with atherosclerosis, or a coreceptor for HIV-I, e.g., CCR5. In one embodiment, the LDL associated with atherosclerosis is oxidized or minimally modified.

In one embodiment, the self-antigen is an autoimmune disease antigen. Exemplary autoimmune disease antigens include, but are not limited to, the muscle acetylcholine receptor (the antibodies are associated with the disease myasthenia gravis); cardiolipin (associated with the disease lupus); platelet associated proteins (associated with the disease idiopathic thrombocytopenic purpura); the multiple antigens associated with Sjogren's Syndrome; the antigens implicated in the case of tissue transplantation autoimmune reactions; the antigens found on heart muscle (associated with the disease autoimmune myocarditis); the antigens associated with immune complex mediated kidney disease; the double-stranded and single-stranded DNA antigens (associated with lupus nephritis); desmogleins and desmoplakins (associated with pemphigus and pemphigoid); insulin and glutamic acid decarboxylase for type 1 diabetes, myelin-associated proteins for multiple sclerosis, and heat-sock protein 60 for rheumatoid arthritis.

In other embodiments, the self antigen is an atopic disease antigen, e.g., peptides derived from IgE, such as the histamine releasing decapeptide of IgE (the Stanworth decapeptide).

Immunogens suitable for use in the vaccines and methods of the invention may be obtained from any source. For example, infectious agents for use in formulating the vaccines of the present invention can be obtained from commercial sources, including, but not limited to, American Type Culture Collection (ATCC). In some embodiments, the infectious agents are passed in cell culture and/or animals prior to being combined with a bisphosphonate and a pharmaceutically acceptable carrier. In other embodiments, suitable immunogens not purified (or cellular lysates), partially purified (e.g., cell lysates have been removed), or purified. In other embodiments, suitable immunogens are prepared recombinantly.

In one embodiment, a suitable immunogen is present in a commercially available vaccine (e.g., a commercially available vaccine comprising alum). In one embodiment, the commercially available vaccine for use in the compositions and methods of the invention has been approved by a regulatory agency such as, for example, the United States Food and Drug Administration, the European Medicines Agency (EMA), the Japanese Ministry of Health and Welfare (MHW), the Therapeutic Goods Administration of Australia, the State Food and Drug Administration (SFDA) (China), and the Health Protection Branch of Canada.

The commercially suitable vaccines suitable for use in the compositions and methods of the invention include, for example, vaccines suitable for human and veterinary administration.

Examples of commercially available vaccines for use in the vaccines and methods of the invention include, without limitation, those listed below.

Commercially Available Vaccines

| Product Name | Trade Name | Sponsor |
| --- | --- | --- |
| Adenovirus Type 4 and Type 7 Vaccine, Live Oral | No Trade Name | Barr Labs, Inc. |
| Anthrax Vaccine Adsorbed | Biothrax | Emergent BioDefense Operations Lansing Inc. |
| BCG Live | BCG Vaccine | Organon Teknika Corp LLC |
| BCG Live | Mycobax | Sanofi Pasteur, Ltd |
| BCG Live | TICE BCG | Organon Teknika Corp LLC |
| Diphtheria & Tetanus Toxoids Adsorbed | No Trade Name | Sanofi Pasteur, Inc |
| Diphtheria & Tetanus Toxoids Adsorbed | No Trade Name | Sanofi Pasteur, Ltd |
| Diphtheria & Tetanus Toxoids & Acellular Pertussis Vaccine Adsorbed | Tripedia | Sanofi Pasteur, Inc |
| Diphtheria & Tetanus Toxoids & Acellular Pertussis Vaccine Adsorbed | Infanrix | GlaxoSmithKline Biologicals |
| Diphtheria & Tetanus Toxoids & Acellular Pertussis Vaccine Adsorbed | DAPTACEL | Sanofi Pasteur, Ltd |
| Diphtheria & Tetanus Toxoids & Acellular Pertussis Vaccine Adsorbed, Hepatitis B (recombinant) and Inactivated Poliovirus Vaccine Combined | Pediarix | GlaxoSmithKline Biologicals |
| Diphtheria and Tetanus Toxoids and Acellular Pertussis Adsorbed and Inactivated Poliovirus Vaccine10 | KINRIX | GlaxoSmithKline Biologicals |
| Diphtheria and Tetanus Toxoids and Acellular Pertussis Adsorbed, Inactivated Poliovirus and Haemophilus b Conjugate (Tetanus Toxoid Conjugate) Vaccine | Pentacel | Sanofi Pasteur Limited |
| Haemophilus b Conjugate Vaccine (Meningococcal Protein Conjugate) | PedvaxHIB | Merck & Co, Inc |
| Haemophilus b Conjugate Vaccine (Tetanus Toxoid Conjugate) | ActHIB | Sanofi Pasteur, SA |
| Haemophilus b Conjugate Vaccine (Tetanus Toxoid Conjugate) | Hiberix | GlaxoSmithKline Biologicals, S.A. |
| Haemophilus b Conjugate Vaccine (Meningococcal Protein Conjugate) & Hepatitis B Vaccine (Recombinant) | Comvax | Merck & Co, Inc |
| Hepatitis A Vaccine, Inactivated | Havrix | GlaxoSmithKline Biologicals |
| Hepatitis A Vaccine, Inactivated | VAQTA | Merck & Co, Inc |
| Hepatitis A Inactivated and Hepatitis B (Recombinant) Vaccine | Twinrix | GlaxoSmithKline Biologicals |
| Hepatitis B Vaccine (Recombinant) | Recombivax HB | Merck & Co, Inc |
| Hepatitis B Vaccine (Recombinant) | Engerix-B | GlaxoSmithKline Biologicals |
| Human Papillomavirus Quadrivalent (Types 6, 11, 16, 18) Vaccine, Recombinant | Gardasil | Merck and Co, Inc. |
| Human Papillomavirus Bivalent (Types 16, 18) Vaccine, Recombinant | Cervarix | GlaxoSmithKline Biologicals |
| Influenza A (H1N1) 2009 Monovalent Vaccine | No Trade Name | CSL Limited |
| Influenza A (H1N1) 2009 Monovalent Vaccine | No Trade Name | MedImmune LLC |
| Influenza A (H1N1) 2009 Monovalent Vaccine | No Trade Name | ID Biomedical Corporation of Quebec |
| Influenza A (H1N1) 2009 Monovalent Vaccine | No Trade Name | Novartis Vaccines and Diagnostics Limited |
| Influenza A (H1N1) 2009 Monovalent Vaccine | No Trade Name | Sanofi Pasteur, Inc. |
| Influenza Virus Vaccine | Afluria | CSL Limited |
| Influenza Virus Vaccine, H5N1 (for National Stockpile) | No Trade Name | Sanofi Pasteur, Inc. |
| Influenza Virus Vaccine, Trivalent, Types A and B | FluLaval | ID Biomedical Corp of Quebec |
| Influenza Vaccine, Live, Intranasal | FluMist | MedImmune, LLC |
| Influenza Virus Vaccine, Trivalent, Types A and B | Fluarix | GlaxoSmithKline Biologicals |
| Influenza Virus Vaccine, Trivalent, Types A and B | Fluvirin | Novartis Vaccines and Diagnostics Ltd |
| Influenza Virus Vaccine, Trivalent, Types A and B | Agriflu | Novartis Vaccines and Diagnostics S.r.l. |
| Influenza Virus Vaccine, | Fluzone and | Sanofi Pasteur, Inc |

| Product Name | Trade Name | Sponsor |
|---|---|---|
| Trivalent, Types A and B | Fluzone High-Dose | |
| Japanese Encephalitis Virus Vaccine, Inactivated, Adsorbed | Ixiaro | Intercell Biomedical |
| Japanese Encephalitis Virus Vaccine Inactivated | JE-Vax | Research Foundation for Microbial Diseases of Osaka University |
| Measles Virus Vaccine, Live | Attenuvax | Merck & Co, Inc |
| Measles and Mumps Virus Vaccine, Live | M-M-Vax | Merck & Co, Inc (not available) |
| Measles, Mumps, and Rubella Virus Vaccine, Live | M-M-R II | Merck & Co, Inc |
| Measles, Mumps, Rubella and Varicella Virus Vaccine Live | ProQuad | Merck & Co, Inc |
| Meningococcal (Groups A, C, Y, and W-135) Oligosaccharide Diphtheria CRM197 Conjugate Vaccine | Menveo | Novartis Vaccines and Diagnostics, Inc. |
| Meningococcal Polysaccharide (Serogroups A, C, Y and W-135) Diphtheria Toxoid Conjugate Vaccine | Menactra | Sanofi Pasteur, Inc |
| Meningococcal Polysaccharide Vaccine, Groups A, C, Y and W-135 Combined | Menomune-A/C/Y/W-135 | Sanofi Pasteur, Inc |
| Mumps Virus Vaccine Live | Mumpsvax | Merck & Co, Inc |
| Plague Vaccine | No trade name | Greer Laboratories Inc. (not available) |
| Pneumococcal Vaccine, Polyvalent | Pneumovax 23 | Merck & Co, Inc |
| Pneumococcal 7-valent Conjugate Vaccine (Diphtheria CRM197 Protein) | Prevnar | Wyeth Pharmaceuticals Inc |
| Pneumococcal 13-valent Conjugate Vaccine (Diphtheria CRM197 Protein) | Prevnar 13 | Wyeth Pharmaceuticals Inc |
| | Poliovax | Sanofi Pasteur, Ltd (not available) |
| | IPOL | Sanofi Pasteur, SA |
| Poliovirus Vaccine Inactivated (Human Diploid Cell) | Imovax | Sanofi Pasteur, SA |
| Poliovirus Vaccine Inactivated (Monkey Kidney Cell) | RabAvert | Novartis Vaccines and Diagnostics |
| Rabies Vaccine | No Trade Name | BioPort Corp(not available) |
| Rabies Vaccine | ROTARIX | GlaxoSmithKline Biologicals |
| Rabies Vaccine Adsorbed | RotaTeq | Merck & Co., Inc. |
| Rotavirus Vaccine, Live, Oral | Meruvax II | Merck & Co, Inc |
| Rotavirus Vaccine, Live, Oral, Pentavalent | ACAM2000 | Sanofi Pasteur Biologics Co. |
| Rubella Virus Vaccine Live | No Trade Name | MassBiologics |
| Smallpox (Vaccinia) Vaccine, Live | DECAVAC | Sanofi Pasteur, Inc |
| Tetanus & Diphtheria Toxoids Adsorbed for Adult Use | TENIVAC | Sanofi Pasteur, Ltd (not available) |
| Tetanus & Diphtheria Toxoids Adsorbed for Adult Use | No Trade Name | Sanofi Pasteur, Inc |
| Tetanus & Diphtheria Toxoids Adsorbed for Adult Use | No Trade Name | Sanofi Pasteur, Inc |
| Tetanus Toxoid | Adacel | Sanofi Pasteur, Ltd |
| Tetanus Toxoid Adsorbed | Boostrix | GlaxoSmithKline Biologicals |
| Tetanus Toxoid, Reduced Diphtheria Toxoid and Acellular Pertussis Vaccine, Adsorbed | Vivotif | Berna Biotech, Ltd |
| Tetanus Toxoid, Reduced Diphtheria Toxoid and Acellular Pertussis Vaccine, Adsorbed | TYPHIM Vi | Sanofi Pasteur, SA |
| Typhoid Vaccine Live Oral Ty21a | Varivax | Merck & Co, Inc |
| Typhoid Vi Polysaccharide Vaccine | YF-Vax | Sanofi Pasteur, Inc |
| Varicella Virus Vaccine Live | Zostavax | Merck & Co., Inc. |

Additional commercially available vaccines suitable for use in the vaccines and methods of the invention may be found at, for example, www.fda.gov/BiologicsBloodVaccines/default.htm.

Non-limiting examples of commercially available veterinary vaccines for use in the vaccines and methods of the invention include those listed below.

Commercially Available Veterinary Vaccines

| Target pathogen | Target animal | Brand name(s) | Distributor | Characteristic(s) |
|---|---|---|---|---|
| PCV2 | Pigs | Porcilis-PCV2 | Intervet | Inactivated baculovirus expressed PCV2 ORF2 protein; adjuvanted |
| PCV2 | Pigs | Suvaxyn PCV2 | Fort Dodge | Inactivated PCV1-2 chimera; adjuvanted |
| Pseudorabies virus | Pigs | Suvaxyn Aujeszky | Fort Dodge | gE- and thymidine kinase-deleted marker vaccine |
| Classical swine fever virus | Pigs | Porcilis Pesti | Intervet | Baculovirus recombinant E2 protein without emulsion |

-continued

| Target pathogen | Target animal | Brand name(s) | Distributor | Characteristic(s) |
|---|---|---|---|---|
| Classical swine fever virus | Pigs | Bayovac CSF E2 | Bayer Leverkusen | Baculovirus recombinant E2 protein without emulsion |
| BHV-1 | Cattle | Bovilis IBR Marker | Intervet | Live or inactivated gE-deleted marker vaccine |
| Equine influenza virus | Horses | PROTEQ-FLU (European Union), Recombitek (United States) | Merial | Canarypox virus-vectored vaccine |
| WNV | Horses | PreveNile | Intervet | Live flavivirus chimera vaccine |
| WNV | Horses | West Nile-Innovator DNA | Fort Dodge | DNA vaccine |
| WNV | Horses | RECOMBITEKEquine WNV | Merial | Canarypox virus-vectored vaccine |
| MDV (HTV) and IBDV | Poultry | Vaxxitek HVT + IBD | Merial | Live recombinant chimera virus expressing VP2 gene of IBD on HTV virus |
| Newcastle disease virus | Poultry | NA | Dow AgroSciences | HN recombinant produced in plant cell lines (registered but not on market) |
| Newcastle disease virus | Poultry | Vectormune FP-ND | Biomune | Fowlpox virus vectored |
| Avian influenza virus (H5N1) and NDV | Poultry | | Intervet | Chimera virus on NDV backbone; field trials in 2007 |
| Avian influenza virus | Poultry | Poulvac FluFend I AI H5N3 RG | Fort Dodge | Chimera H5N3 virus, inactivated in oil-based adjuvant |
| Avian influenza virus | Poultry | Trovac AI H5 | Merial | Fowlpox virus-vectored H5 |
| Rabies virus | Wildlife, canines | Raboral | Merial | Vaccinia virus recombinant |
| Rabies virus | Cats | Purevax Feline Rabies | Merial | Canarypox virus-vectored vaccine |
| Rabies virus | Cats | PUREVAX Feline Rabies | Merial | Canarypox virus-vectored vaccine |
| Feline leukemia virus | Cats | EURIFEL FeLV | Merial | Canarypox virus-vectored vaccine |
| Canine parvovirusl | Dogs | RECOMBITEK Canine Parvo | Merial | Modified live virus |
| Canine coronavirus | Dogs | RECOMBITEK Corona MLV | Merial | Modified live virus |
| Canine distemper virus | Dogs | RECOMBITEK rDistemper | Merial | Canarypox virus-vectored vaccine (HA and F antigens) |
| Canine distemper virus | Fur animals | PUREVAXFerret Distemper | Merial | Canarypox virus-vectored vaccine |
| IHN virus | Salmon | Apex-IHN | Novartis (Aqua Health) | DNA vaccine |

Additional commercially available veterinary vaccines suitable for use in the vaccines and methods of the invention may be found in, for example, "Current Veterinary Biologics Product Catalogue", United States Department of Agriculture quarterly publication (see, e.g., www.aphis.usda.gov/animal_health/vet_biologics/vb_licensed_products.shtml).

The vaccines of the present invention may also include a pharmaceutically acceptable carrier. As used herein, a "pharmaceutically acceptable carrier" refers to any substance or vehicle suitable for the intended route of administration of the bisphosphonate and, where applicable, the at least one immunogen. A pharmaceutically acceptable carrier includes any and all excipients, solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired and that are physiologically compatible (see, e.g., Remington's The Science and Practice of Pharmacy, 21st Edition, A. R. Gennaro, Lippincott, Williams & Wilkins, Baltimore, Md., 2006, the entire contents of which are incorporated herein by reference).

Suitable pharmaceutically acceptable excipients used in the vaccines of the invention include, but are not limited to, inert diluents, dispersing and/or granulating agents, surface active agents and/or emulsifiers, disintegrating agents, binding agents, preservatives, buffering agents, lubricating agents, and/or oils.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite and Veegum), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate, polyoxyethylene sorbitan, polyoxyethylene sorbitan monooleate, sorbitan monopalmitate, sorbitan monostearate, sorbitan tristearate, glyceryl monooleate, sorbitan monooleate), polyoxyethylene esters (e.g., polyoxyethylene monostearate, polyoxyethylene hydrogenated castor oil, polyethoxylated castor oil, polyoxymethylene stearate, and Solutol), sucrose fatty acid esters, polyethylene glycol fatty acid esters (e.g. Cremophor®), polyoxyethylene ethers, (e.g., polyoxyethylene lauryl ether), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an antioxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. Nos. 5,912,014, 6,086,918 and 6,673,574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft- and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft- and hard-filled gelatin capsules using such excipients as lactose or milk sugar as well as high molecular weight polethylene glycols and the like.

The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Injectable formulations, for example, sterile injectable aqueous or oleaginous suspensions may be formulated according to the known art using suitable dispersing or wetting agents and suspending agents. A sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Suitable devices for use in delivering intradermal vaccines described herein include short needle devices such as those described in U.S. Pat. Nos. 4,886,499; 5,190,521;

5,328,483; 5,527,288; 4,270,537; 5,015,235; 5,141,496; and 5,417,662. Intradermal vaccines may be administered by devices which limit the effective penetration length of a needle into the skin, such as those described in PCT publication WO99/34850 and functional equivalents thereof. Jet injection devices which deliver liquid vaccines to the dermis via a liquid jet injector and/or via a needle which pierces the stratum coraeum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for nasal administration may, for example, comprise from about as little as 0.1% (w/w) and as much as 100% (w/w) of the active ingredient, and may comprise one or more of the additional ingredients described herein. A vaccine of the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for administration to buccal mucosa may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 µm to about 200 µm, and may further comprise one or more of the additional ingredients described herein.

In one embodiment, the vaccines of the invention comprising a bisphosphonate may further comprise an additional adjuvant. Such adjuvants are known in the art and include, without limitation, inorganic adjuvants, e.g., alum (e.g., aluminum potassium sulphate and aluminum hydroxide), organic adjuvants (e.g., Squalene AS03 and AS04 (GlaxoSmithKline)), oil-based adjuvants (e.g., Freund's Complete Adjuvant, MF59 (Novartis)), bacterial-derived adjuvants, e.g., TLR-dependent adjuvants (e.g., adjuvants that act directly on dendritic cells (DCs) and/or other antigen-presenting cells (APC)), agents that induce the up-regulation of cytokines, MHC class II, and costimulatory molecules, and agents that promote DC migration to the T cell area of the lymph node, e.g., TLR agonists, e.g., TLR-2, TLR-3, TLR-4, TLR-7, TLR-8, and TLR-9 agonists, including nonmethylated CpG oligonucleotide (CpG), and monophosphoryl lipid A (MPL)), virisomes and virus-like particles, QS21 from *Quillaja saponaria* (Ghochikyan A, et al. (2006) *Vaccine* 24 (13): 2275), MF59, agents that activate inflammasomes, attenuated or killed intact microbes and microbial lysates, or fragments thereof, nanoparticles, agents that induce or mimic CD40L, topical exposure of skin to low-frequency ultrasound with SDS, injected ex vivo modified APC, such as antigen-pulsed DC and B cells, genetically engineered cell lines, and fusions of APC with tumor cells, liposomes, e.g., liposomes comprising cationic cholesterol derivatives or neutral phopholipids, and ISCOMs (immune stimulating complexes). In one embodiment, the adjuvant is alum. In another embodiment of the invention, a vaccine as described herein only comprises bisphosphonate as an adjuvant, i.e., does not comprise an additional adjuvant.

The vaccines described herein may be prepared by any method known in the art. In general, such preparatory methods include the step of bringing the bisphosphonate, and one or more pharmaceutically acceptable carriers into association. In some embodiments, the prepatory method will also include bringing the at least one immunogen into association with the bisphosphonate and one or more pharmaceutically acceptable carriers. Then, if necessary and/or desirable, the product is shaped and/or packaged into a desired single- or multi-dose unit. Vaccine preparation is generally described in New Trends and Developments in Vaccines, edited by Voller et al., University Park Press, Baltimore, Md., U.S.A. 1978 and is incorporated in its entirety herein by reference.

The amount of a bisphosphonate in the vaccines of the present invention may be in the range of about 1-500,000 µg per dose, about 1-50,000 µg per dose, about 1-5000, about 1-1000 µg per dose, about 1-500 µg per dose, and about 1-100 µg per dose, or about 1-25 µg per dose.

The amount of immunogen in the vaccines of the invention may be about 0.01-100,000 µg of immunogen, about 0.01-10,000 µg of immunogen, about 0.01-1000 µg of immunogen, about 0.01-500 µg, about 0.01-100 µg, or about 0.01 to 50 µg, about 1-1000 µg of immunogen, about 1-500 µg, about 1-100 µg, or about 1 to 50 µg. It should be understood that a range between any two figures listed above is specifically contemplated to be encompassed within the metes and bounds of the present invention. Some variation in dosage will necessarily occur depending on the condition of the specific immunogen and the subject being immunized.

The vaccines of the present invention may be administered by any suitable route. In a preferred embodiment, a vaccine is administered intramuscularly, subcutaneously, intradermally, intranasally, orally, transcutaneously, or mucosally. In another embodiment, a vaccine of the invention is not administered orally. An intramuscular administration may be given, for example, by injection into skeletal muscles such as the gluteal, deltoid, rectus femoris, or vastus lateralis muscles.

As described in detail Below in Section III, in certain embodiments of the invention, a bisphosphonate is provided as a component of a particle delivery system and is suitable for administration to a human subject. In other embodiments, a bisphosphonate is not provided as a component of a particle delivery system, i.e., free bisphosphonate and is suitable for administration to a non-human subject.

Following an initial administration of a vaccine, subjects may receive one or several booster vaccines adequately spaced. Such a vaccine may be administered as in either a priming or boosting vaccination regime.

The vaccines of the present invention are administered at a dose that is sufficient to elicit a detectable immune response in a subject based on the mode of administration and without significant adverse side effects, e.g., serious allergic reaction, seizure, high fever, coma, or lowered consciousness, permanent brain damage, Guillain-Barré Syndrome, deafness, pneumonia, and/or major organ system failure. Such an amount will vary depending upon which specific immunogen is employed and how it is presented. An optimal amount for a particular vaccine can be ascertained by standard studies involving observation of appropriate immune responses in non-human animal models and/or vaccinated subjects.

III. Bisphosphonates

Bisphosphonate refers generally to a class of compounds which include two phosphonate ($PO_3$) groups. Bisphosphonates are analogs of pyrophosphates that contain two phosphonate groups attached to (typically one) central carbon that replaces the oxygen in pyrophosphate. Because they form a three-dimensional structure capable of chelating divalent cations such as $Ca^{2+}$, bisphosphonates have a strong affinity for bone and can target bone surfaces, which are undergoing remodeling. Accordingly, they are used extensively in conditions characterized by osteoclast-mediated bone resorption, including osteoporosis, Paget's disease, tumor-associated osteolysis and hypercalcemia.

Although the molecular mechanism by which nitrogen-containing and non-nitrogen-containing bisphosphonates affect osteoclasts seem to be different, it is generally agreed that they function as bone resorption inhibitors, at least partially, by inhibiting the function of osteoclasts. (Rodan, Annu Rev Pharmacol Toxicol. 38:375 388 (1998); Rogers et al., Bone, 24:73S 79S (1999); Russell et al., Osteoporos Int. 9:S66 80 (1999)). It is believed that bisphosphonates target osteoclasts because of their high affinity to bone mineral, however, there is evidence for both a direct blocking effect on osteoclasts as well as an apoptosis-inducing effect.

Clodronate (also referred to as dichloromethylene diphosphonate), which has been used for treating osteolytic bone diseases and osteoporosis, is potent anti-macrophage agent both in vivo and in vitro when incorporated into a liposome (van Rooijen et al., Cell Tissue Res. 238:355 358 (1984); Claassen et al., J Immunol Methods, 134:153 161 (1990)). Clodoronate liposomes (CLL) are micron sized multilameral liposomes which encapsulate the drug clodronate in their empty spaces. They are formed by phoshatidylcholine and cholesterol to increase the stability in serum. The liposomal drug is taken up by macrophages and rapidly causes apoptosis (van Rooijen et al., J Immunol Methods, 193:93 99 (1996); Schmidt-Weber et al., J Leukoc Biol., 60:230 244 (1996); Naito et al., J Leukoc Biol. 60:337 344 (1996)). It is believed that the in vivo effects of clodronate are influenced by its route of administration. Injection into tissues leads to the depletion of macrophages from the tissue itself and from draining lymph nodes. Intravenous injection of liposomally encapsulated clodronate leads to near complete depletion of splenic (and hepatic) macrophages and marginal zone dendritic cells within 24 hours (van Rooijen et al., J Immunol Methods, 174:83 93 (1994)). Unlike other methods of macrophage depletion, however, this treatment does not lead to the secretion of proinflammatory cytokines by the dying macrophages (van Rooijen et al., J Leukoc Biol., 62:702 709 (1997)). Moreover, liposomal clodronate appears to have a very selective effect on macrophages and phagocytic dendritic cells. Neutrophils and lymphocytes have not been found to be directly affected by the drug (van Rooijen et al., 1994, supra; van Rooijen et al., J Leukoc Biol. 45:97 104 (1989); Alves-Rosa et al., Blood. 96:2834 2840 (2000)).

Once CLL are injected, they are immediately recognized by macrophages that eat them and form vesicles known as phagosomes. Lysosomes fuse with phagosomes resulting in a phagolysosome, which destroys the liposome membrane and results in the release of clodronate in the cytosol. Here it is mistakenly metabolized as a toxic ATP analog that blocks the ATP translocase of mitochondria. Mitochondria release molecular signals that initiate cell death by apoptosis. (Frith, J et al., Journal of Bone and Mineral Research 1997). CLL treatment is used to selectively deplete macrophages in vivo. See FIG. 1.

One component of the vaccines and methods of the present invention is a bisphosphonate. According to the present invention, a bisphosphonate is a pyrophosphate analog in which a carbon atom replaces the central atom of oxygen (i.e., having a P—C—P backbone). This carbon substitution makes these compounds resistant to hydrolysis, and allows two additional chains of variable structure. One of these side chains usually contains a hydroxyl moiety, which allows high affinity for calcium crystals and bone mineral (noting the prevalent use to treat bone disease). The differences at the other side chain produce marked differences in the anti-resorptive potency of different bisphosphonates. Newer bisphosphonates, such as ibandronate and zoledronic acid, show 10,000 100,000-fold greater potency than do the older agents such as etidronate (Berenson et al., "The Role Of Bisphosphonates In Multiple Myeloma", for the American Society of Clinical Oncology Bisphosphonates Expert Panel (2002)). Bisphosphonates are well-known in the art, and are reviewed or described, for example, in: Body, Eur. J. Cancer 34:263 9 (1998); Fleisch, Endocr. Rev. 19:80 100 (1998); Vasikaran, Ann Clin Biochem 38(Pt 6):608 623 (2001); Niemi et al., Int. J. Pharmaceutics 174:111 115 (1998); Niemi et al., Eur. J. Phamaceut. Sci. 11:173 180 (2000); van Gelder et al., Bone 16:511 520 (1995); Diez-Perez, Maturitas 43:19 26 (2002); each of which is incorporated by reference in its entirety.

In some embodiments, bisphosphonates suitable for use in the vaccines and methods of the present invention include compounds of formula (I):

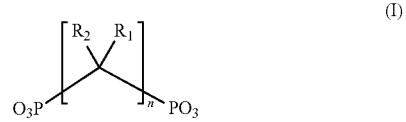

or pharmaceutically acceptable salts thereof;
wherein n is an integer from 1-3;
each occurrence of $R_1$ is, individually, selected from hydrogen, halogen, hydroxy, amino and thio;
each occurrence of $R_2$ is, individually, selected from hydrogen, halogen, hydroxy, thio, amino, $SR_3$, $NR_4R_5$ and $C_{1-6}$ alkyl substituted with 0 or 1 substituents selected from amino, thio, $NR_6R_7$, aryl and heteroaryl;
$R_3$ is selected from hydrogen, $C_{1-6}$ alkyl, $C_{5-7}$ aryl and $C_{5-7}$ haloaryl; and
each $R_4$, $R_5$, $R_6$ and $R_7$ are each individually selected from hydrogen, $C_{1-6}$ alkyl, $C_{5-7}$ cycloalkyl and $C_{5-7}$ aryl.

In some embodiments, n is 1.

In some embodiments, each occurrence of $R_1$ is, individually, selected from hydrogen, halogen and hydroxy. In some embodiments, each occurrence of $R_1$ is, individually, selected from hydrogen, chloro, fluoro, iodo and hydroxy. In some embodiments, at least one occurrence of $R_1$ is hydrogen. In some embodiments, at least one occurrence of $R_1$ is chloro. In some embodiments, at least one occurrence of $R_1$ is hydroxy.

In some embodiments, each occurrence of $R_2$ is, individually, selected from halogen, $SR_3$, $NR_4R_5$ and $C_{1-6}$ alkyl substituted with 0 or 1 substituents selected from $NR_6R_7$, aryl and heteroaryl. In some embodiments, $R_3$ is selected from $C_{5-7}$ aryl and $C_{5-7}$ haloaryl. In some embodiments, each $R_4$, $R_5$, $R_6$ and $R_7$ are each individually selected from hydrogen, $C_{1-6}$ alkyl and $C_{5-7}$ cycloalkyl. In some embodiments, at least one occurrence of $R_2$ is halogen. In some embodiments, at least one occurrence of $R_2$ is $C_{1-6}$ alkyl. In some embodiments, at least one occurrence of $R_2$ is $C_{1-6}$ alkyl substituted with $NR_6R_7$, wherein $R_6$ and $R_7$ are each individually selected from hydrogen or $C_{1-6}$ alkyl. In some embodiments, at least one occurrence of $R_2$ is $C_{1-6}$ alkyl substituted with pyridine or imidazole. In some embodiments, at least one occurrence of $R_2$ is selected from $SR_3$, wherein $R_3$ is selected from $C_{5-7}$ haloaryl. In some embodiments, at least one occurrence of $R_2$ is chloro. In some embodiments, at least one occurrence of $R_2$ is methyl.

In some embodiments, bisphosphonates suitable for use in the vaccines and methods of the present invention include compounds of formula (I-A):

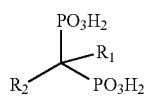

(IA)

or pharmaceutically acceptable salts thereof;
wherein $R_1$ is selected from hydrogen, halogen, hydroxy, amine and thio; and
$R_2$ is selected from hydrogen, halogen, hydroxy, thio, amino, $SR_3$, $NR_4R_5$ and $C_{1-6}$ alkyl substituted with 0 or 1 $NR_6R_7$, thio, $C_{5-7}$ aryl or $C_{5-7}$ heteroaryl;
$R_3$ is selected from hydrogen, $C_{1-6}$ alkyl, $C_{5-7}$ aryl and $C_{5-7}$ haloaryl; and
each $R_4$, $R_5$, $R_6$ and $R_7$ are each individually selected from hydrogen, $C_{1-6}$ alkyl, $C_{5-7}$ cycloalkyl and $C_{5-7}$ aryl.

In some embodiments $R_1$ is selected from hydrogen, halogen and hydroxy. In some embodiments, $R_1$ is selected from hydrogen, chloro, fluoro, iodo and hydroxy. In some embodiments, $R_1$ is hydrogen. In some embodiments, $R_1$ is chloro. In some embodiments, $R_1$ is hydroxy.

In some embodiments $R_2$ is selected from halogen, $SR_3$, $NR_4R_5$ and $C_{1-6}$ alkyl substituted with 0 or 1 substituents selected from $NR_6R_7$, $C_{5-7}$ aryl and $C_{5-7}$ heteroaryl. In some embodiments, $R_3$ is selected from $C_{5-7}$ aryl and $C_{5-7}$ haloaryl. In some embodiments, each $R_4$, $R_5$, $R_6$ and $R_7$ are each individually selected from hydrogen, $C_{1-6}$ alkyl and $C_{5-7}$ cycloalkyl. In some embodiments, $R_2$ is halogen. In some embodiments, $R_2$ is $C_{1-6}$ alkyl. In some embodiments, $R_2$ is $C_{1-6}$ alkyl substituted with $NR_6R_7$, wherein $R_6$ and $R_7$ are each individually selected from hydrogen or $C_{1-6}$ alkyl. In some embodiments, $R_2$ is $C_{1-6}$ alkyl substituted with pyridine or imidazole. In some embodiments, $R_2$ is selected from $SR_3$, wherein $R_3$ is selected from $C_{5-7}$ haloaryl. In some embodiments, $R_2$ is chloro. In some embodiments, $R_2$ is methyl.

Worldwide, seven bisphosphonates (clodronate (dichloromethylene diphosphonate), alendronate, etidronate, tiludronate, pamidronate, ibandronate, zoledronate are generally available for various conditions. Prior to 2001, pamidronate intravenous (IV) was approved in the United States for treatment of metastatic bone disease. In February 2002, the U.S. Food and Drug Administration (FDA) approved the use of zoledronic acid for the treatment of patients with multiple myeloma and other metastatic bone disease. Roche Pharmaceuticals, the makers of clodronate, which is available in both IV and oral forms, will soon be seeking FDA approval. In Canada, both pamidronate and clodronate are approved for use in patients with metastatic bone disease. See Berenson et al., 2002, ibid.

In some embodiments, the bisphosphonate for use in the present invention is selected from:

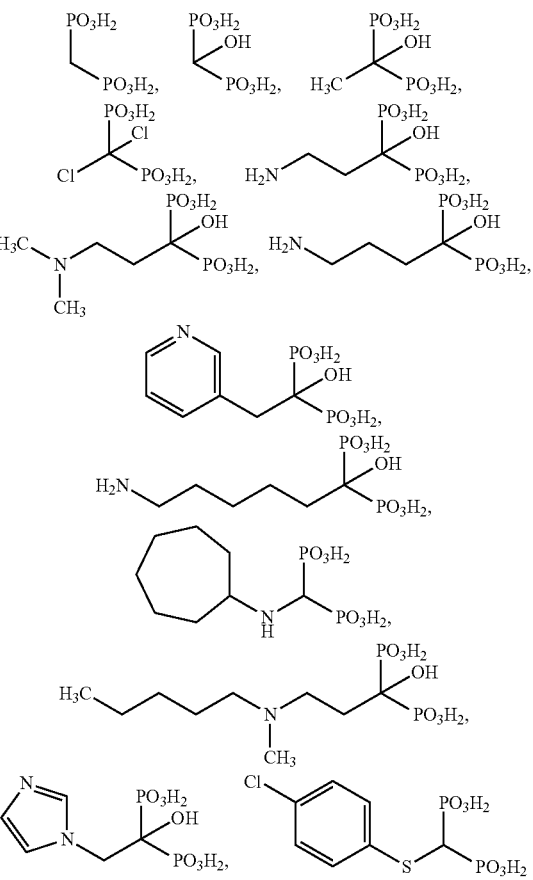

and pharmaceutically acceptable salts thereof.

In some embodiments, the bisphosphonate is selected from medronate, oxidronate, etidronate, clodronate, tiludronate, pamidronate, neridronate, olpadronate, alendronate, ibandronate, risedronate, incadronate, zoledronate, Minodronate (YM529), or biologically active derivatives thereof. The bisphosphonates described in U.S. Pat. Nos. 6,534,488 or 6,509,324, or commercially available bisphosphonates such as those described above, including YH 592 or EB-1053, may be used in the vaccines and methods of the invention. In one embodiment, the bisphosphonate is clodronate or a biologically active derivative or analogue thereof.

According to the present invention, a biologically active derivative or analogue of a bisphosphonate is any compound that is able to mimic the biological activity of a given bisphosphonate, often because the derivative has a basic structure that mimics the basic structure of the given bisphosphonate and/or has the salient biological properties of the given bisphosphonate compound. Biological activity can be measured using any suitable assay known in the art, including by evaluating any chemical or biological activity of the compound, such as those described in Body, 1998, supra; Fleisch, 1998, supra; Vasikaran, 2001, supra; Niemi et al., 1998, supra; Niemi et al., 2000, supra; van Gelder et al., 1995, supra; Diez-Perez, 2002, supra.

Such derivatives can be designed, selected and/or otherwise identified using a variety of methods known in the art. Various methods of drug design, useful to design therapeutic compounds are disclosed in Maulik et al., 1997, Molecular Biotechnology: Therapeutic Applications and Strategies, Wiley-Liss, Inc., which is incorporated herein by reference in its entirety. A bisphosphonate derivative can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In general, the biological activity or biological action of a compound refers to any function(s) exhibited or performed by the compound as measured or observed in vivo (i.e., in the natural physiological environment in which the compound acts) or in vitro (i.e., under laboratory conditions). Modifications of a compound, such as by creation of a derivative of such a compound, may result in compounds having the same biological activity as the lead compound, or in compounds having decreased or increased biological activity as compared to the lead compound. As discussed above, bisphosphonate is a pyrophosphate analog in which a carbon atom replaces the central atom of oxygen (i.e., having a P—C—P backbone), and the various compounds within the type (which can include derivatives) are typically distinguished by two additional chains of variable structure. Indeed, bisphosphonates are considered to be derivatives of pyrophosphate and therefore, a derivative of a given pyrophosphate is also considered to be derivatives of pyrophosphate. As such, derivatives of bisphosphonates can meet the minimum definition of a bisphosphonate above (a pyrophosphate analog in which a carbon atom replaces the central atom of oxygen (i.e., having a P—C—P backbone)).

As used herein, "alkyl" groups include saturated hydrocarbons having one or more carbon atoms, including straight-chain alkyl groups (e.g., methyl, ethyl, propyl, butyl, pentyl, hexyl, methylene, ethylene, propylene, butylene, pentylene, hexylene, etc.), cyclic alkyl groups (or "cycloalkyl" or "alicyclic" or "carbocyclic" groups) (e.g., cyclopropyl, cyclopentyl, cyclohexyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The term "$C_{1-6}$" as in "$C_{1-6}$ alkyl" means alkyl groups containing 1 to 6 carbon atoms.

The terms "halo" and "halogen," as used herein, refer to an atom selected from fluorine, chlorine, bromine and iodine.

As used herein, the term "thio" refers to an —SH group. The term "amino," as used herein, refers to an —$NH_2$ group.

As used herein, the term "aryl" and "heteroaryl", as used herein, refer to stable mono- or polycyclic, heterocyclic, polycyclic, and polyheterocyclic unsaturated moieties having about 3-14 carbon atoms, each of which may be substituted or unsubstituted. In some embodiments, aryl refers to a mono- or bicyclic carbocyclic ring system having one or two aromatic rings. Exemplary aryls include, but are not limited to, phenyl, naphthyl, tetrahydronaphthyl, indanyl, indenyl and the like. In some embodiments, heteroaryl refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms. Exemplary heteroaryls include, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. The term "$C_{5-6}$ aryl" means aryl groups containing 5 to 7 carbon atoms. The term "$C_{5-7}$ heteroaryl" means heteroaryl groups containing 5 to 7 ring atoms (including carbons and heteroatoms).

In certain embodiments of the invention, a bisphosphonate is provided as a component of a particle delivery system. In other embodiments, a bisphosphonate is not provided as a component of a particle delivery system, i.e., it is used as a free bisphosphonate.

As used herein, a "particle" refers to any entity having a diameter of less than 10 microns (μm). In some embodiments, the particle is a nanoparticle, i.e., a particle having a longest dimension (e.g., diameter) of 1000 nm or less. In some embodiments, particles have a diameter of 300 nm or less. Particles may be polymeric (e.g., branched, crosslinked or dendritic carriers) or non-polymeric (e.g., a metal particle, quantum dot, ceramic, inorganic material, bone). Polymers may be biocompatible naturally occurring polymers, synthetic polymers or synthetic copolymers.

As used herein, the term "particle delivery system" refers to a composition in which the bisphosphonate is encapsulated, embedded, and/or adsorbed within a particle, dispersed in the particle matrix, adsorbed on or linked to the particle surface, or in combination of any of these forms.

A particle delivery system for use in the vaccines and methods of the invention includes, but is not limited to, surfactant-based emulsions, e.g., micelles, lipid-based particles, e.g., liposomes (e.g., multilamellar vesicles (MLVs), small unilamellar vesicles (SUVs) or extruded lipids (Templeton et al., 1997, Nature Biotech., 15:647 652)), microparticles, microspheres, microcapsules, nanocapsules, nanoparticles, e.g., polymeric nanoparticles, metallic nanoparticles, nanoparticles that are developed using a combination of nanomaterials such as lipid-polymer nanoparticles, picoparticles, dendrimers, buckyballs, nanowires, virus-like particles, peptide or protein-based particles (such as albumin nanoparticles)

Particle delivery systems are well known in the art and are described in, for example, PCT Publication No. WO 00/000215, U.S. Pat. No. 5,543,158, U.S. Patent Application No. 20060002852, U.S. Patent Application No. 20090028910, U.S. Pat. No. 6,984,400 and M. Donbrow in: Microencapsulation and Nanoparticles in Medicine and Pharmacy, CRC Press, Boca Raton, Fla., 347, the entire contents of each of which are incorporated herein by reference).

IV. Methods of the Invention

The present invention also provides various methods for use of vaccines containing a bisphosphonate, e.g., a bisphosphonate and at least one immunogen, to stimulate an immune response. These methods may serve to enhance the immunogenicity of the at least one immunogen, to stimulate an antibody response to the at least one immunogen, and/or to directly stimulate B cells to produce an antibody to the at least one immunogen. The methods may be used for both prophylactic and therapeutic purposes (e.g., for the prevention and treatment of infection and/or for the prevention and treatment of cancer).

In one aspect the present invention provides methods for stimulating an immune response in a subject. The methods include administering to the subject a bisphosphonate in an amount effective to stimulate an immune response in the subject, thereby stimulating an immune response. In one embodiment, the methods further include administering at least one immunogen to the subject. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

Another aspect of the invention provides methods for stimulating an immune response to at least one immunogen in a subject. The methods include administering to the subject a bisphosphonate in an amount effective to stimulate an immune response to the at least one immunogen in the subject. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

In another aspect, the present invention provides methods for enhancing the immunogenicity of at least one immunogen in a subject. The methods include administering to the subject the at least one immunogen and a bisphosphonate in an amount effective to enhance the immunogenicity of the at least one immunogen, thereby enhancing the immunogenicity of the at least one immunogen in the subject. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

In another aspect, the present invention provides methods of stimulating an antibody response, e.g., a neutralizing antibody response, to at least one immunogen in a subject. The methods include administering to the subject the at least one immunogen and a bisphosphonate in an amount effective to stimulate an antibody response, e.g., a neutralizing antibody response, to the at least one immunogen, thereby stimulating an antibody response to the at least one immunogen in the subject. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

In yet another aspect, the present invention provides methods of stimulating an immune response to a vaccine in a subject. The methods include administering a vaccine, e.g., a commercially available vaccine, to a subject and administering to the subject a bisphosphonate in an amount effective to stimulate an immune response to the vaccine in the subject. The vaccine may be a commercially available vaccine, such as those described supra. In one embodiment, the vaccine is a commercially available vaccine selected from the group consisting of an Adenovirus Type 4 and Type 7 Vaccine, Live, Oral, a Anthrax Vaccine Adsorbed, a BCG Live, a Diphtheria & Tetanus Toxoids, a Diphtheria & Tetanus Toxoids & Acellular Pertussis Vaccine Adsorbed, a Diphtheria & Tetanus Toxoids & Acellular Pertussis Vaccine Adsorbed, a Hepatitis B (recombinant) and Inactivated Poliovirus Vaccine Combined, a Diphtheria and Tetanus Toxoids and Acellular Pertussis Adsorbed and Inactivated Poliovirus Vaccine-10, a Diphtheria and Tetanus Toxoids and Acellular Pertussis Adsorbed, an Inactivated Poliovirus and *Haemophilus* b Conjugate (Tetanus Toxoid Conjugate) Vaccine, a *Haemophilus* b Conjugate Vaccine (Meningococcal Protein Conjugate), a *Haemophilus* b Conjugate Vaccine (Tetanus Toxoid Conjugate), *Haemophilus* b Conjugate Vaccine (Meningococcal Protein Conjugate) & Hepatitis B Vaccine (Recombinant), a Hepatitis A Vaccine, Inactivated, a Hepatitis A Inactivated and Hepatitis B (Recombinant) Vaccine, a Hepatitis B Vaccine (Recombinant), a Human Papillomavirus Quadrivalent (Types 6, 11, 16, 18) Vaccine, a Recombinant, Human Papillomavirus Bivalent (Types 16, 18) Vaccine, a Recombinant, Influenza A (H1N1) 2009 Monovalent Vaccine, an Influenza Virus Vaccine, Influenza Virus Vaccine, H5N1 (for National Stockpile), an Influenza Virus Vaccine, a Trivalent, Types A and B, Influenza Virus Vaccine, a Trivalent, Types A and B, an Influenza Virus Vaccine, Trivalent, Types A and B, a Japanese Encephalitis Virus Vaccine, Inactivated, Adsorbed, a Japanese Encephalitis Virus Vaccine Inactivated, a Measles Virus Vaccine, Live, a Measles and Mumps Virus Vaccine, Live, a Measles, Mumps, and Rubella Virus Vaccine, Live, a Measles, Mumps, Rubella and Varicella Virus Vaccine Live, a Meningococcal (Groups A, C, Y, and W-135) Oligosaccharide Diphtheria CRM197 Conjugate Vaccine, a Meningococcal Polysaccharide (Serogroups A, C, Y and W-135) Diphtheria Toxoid Conjugate Vaccine, a Meningococcal Polysaccharide Vaccine, Groups A, C, Y and W-135 Combined, a Mumps Virus Vaccine Live, a Plague Vaccine, a Pneumococcal Vaccine, Polyvalent, a Pneumococcal 7-valent Conjugate Vaccine, a Diphtheria CRM197 Protein, a Pneumococcal 13-valent Conjugate Vaccine, a Diphtheria CRM197 Protein, a Poliovirus Vaccine Inactivated (Human Diploid Cell), a Poliovirus Vaccine Inactivated (Monkey Kidney Cell), a Rabies Vaccine, a Rabies Vaccine Adsorbed, a Rotavirus Vaccine, Live, Oral, a Rotavirus Vaccine, Live, Oral, Pentavalent, a Rubella Virus Vaccine Live, a Smallpox (Vaccinia) Vaccine, Live, a Tetanus & Diphtheria Toxoids Adsorbed for Adult Use, a Tetanus Toxoid, a Tetanus Toxoid Adsorbed, a Tetanus Toxoid, Reduced Diphtheria Toxoid and Acellular Pertussis Vaccine, Adsorbed, a Typhoid Vaccine Live Oral Ty21a, a Typhoid Vi Polysaccharide Vaccine, and a Varicella Virus Vaccine Live. A commercially available vaccine and a bisphosphonate can be administered either as separate formulations (e.g., the commercially available vaccine can be administered before, at the same time, or after the bisphosphonate is administered to the subject) or as a single formulation (e.g., the commercially available vaccine can be administered simultaneously with the bisphosphonate). In embodiments in which the commercially available vaccine and the bisphosphonate are administered simultaneously, the commercially available vaccine and the bisphosphonate may be in separate formulations or they may be formulated together, e.g., the commercially available vaccine is re-formulated to include a bisphosphonate. In some embodiment, the bisphosphonate is free bisphosphonate and is not provided in a particle delivery system.

In a further aspect, the present invention provides methods for directly stimulating B cells to produce an antibody to at least one immunogen. The methods include contacting a population of naïve B cells with an immunogen and a bisphosphonate, thereby directly stimulating the B cells to produce the antibody to the at least one immunogen. The at least one immunogen can be a component of a commercially available vaccine, such as a commercially available vaccine comprising at least one additional adjuvant (e.g., alum). In one embodiment, the at least one additional adjuvant is alum. In one embodiment, the methods further include contacting the population of naïve B cells with a commercially available vaccine.

In some embodiments, the contacting is performed in vitro. In alternative embodiments, the contacting is performed in vivo. The antibody produced according to the methods of the invention may be of any isotype, e.g., IgG, IgM, IgA, IgD and IgE. In one embodiment, the antibodies produced according to the methods of the invention comprise IgG antibodies.

The present invention also provides methods of treating a subject susceptible to or suffering from an infectious disease, cancer, or autoimmune disease.

In one aspect, the present invention provides methods for treating an infection. The methods include administering to the subject having an infection or susceptible to an infection, a bisphosphonate, thereby treating the infection. Other methods include administering to the subject having an infection or susceptible to an infection a bisphosphonate and at least one immunogen associated with the infection, thereby treating the infection. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

Infections that may be treated prophylactically or therapeutically using the methods of the invention include, for example, those diseases and disorders that are the result of an infectious agent or an infectious agent product (e.g., virus, bacteria, fungi, parasites, protozoans) described supra.

In another aspect, the present invention provides methods for treating a cancer. The methods include administering to the subject having a cancer or susceptible to a cancer a bisphosphonate, thereby treating the cancer. Other methods include administering to the subject having a cancer or susceptible to a cancer a bisphosphonate and at least one immunogen associated with the cancer, thereby treating the cancer. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

Cancers that may be treated or prevented using the methods of the invention include, for example, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In yet another aspect, the present invention provides methods for treating an autoimmune disease. The methods include administering to the subject having an autoimmune disease or susceptible to an autoimmune disease a bisphosphonate, thereby treating the autoimmune disease. Other methods include administering to the subject having an autoimmune disease or susceptible to an autoimmune disease a bisphosphonate and at least one immunogen associated with the autoimmune disease, thereby treating the autoimmune disease. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

Autoimmune diseases that may be treated and/or prevented using the methods of the invention include, for example, Acute Disseminated Encephalomyelitis (ADEM), Acute necrotizing hemorrhagic leukoencephalitis, Addison's disease, Agammaglobulinemia, Allergic asthma, Allergic rhinitis, Alopecia areata, Amyloidosi, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune myocarditis, Autoimmune pancreatitis, Autoimmune retinopathy, Autoimmune thrombocytopenic purpura (ATP), Autoimmune thyroid disease, Axonal & neuronal neuropathies, Balo disease, Behcet's disease, Castleman disease, Celiac sprue, Chagas disease, Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Graves' disease, Guillain-Barre syndrome, Hashimoto's encephalitis, Hashimoto's thyroiditis, Hemolytic anemia, Henoch-Schonlein purpura, Hypogammaglobulinemia, Idiopathic thrombocytopenic purpura (ITP), IgA nephropathy, IgG4-related sclerosing disease, Inclusion body myositis, Insulin-dependent diabetes (type1), Interstitial cystitis, Juvenile arthritis, Juvenile diabetes, Kawasaki syndrome, Linear IgA disease (LAD), Lupus (SLE), Lyme disease, chronic, Meniere's disease, Mixed connective tissue disease (MCTD), Multiple sclerosis, Myasthenia gravis, Myositis, Neutropenia, Optic neuritis, Pernicious anemia, POEMS syndrome, Polyarteritis nodosa, Type I, II, & III autoimmune polyglandular syndromes, Polymyalgia rheumatica, Polymyositis, Progesterone dermatitis, Primary biliary cirrhosis, Primary sclerosing cholangitis, Psoriasis, Psoriatic arthritis, Idiopathic pulmonary fibrosis, Pyoderma gangrenosum, Reiter's syndrome, Rheumatoid arthritis, Sarcoidosis, Scleroderma, Sperm & testicular autoimmunity, Takayasu's arteritis, Temporal arteritis/Giant cell arteritis, Thrombocytopenic purpura (TTP), Tolosa-Hunt syndrome, Ulcerative colitis, Uveitis, Vasculitis, Vesiculobullous dermatosis, and Wegener's granulomatosis.

The present invention also includes methods for the prophylaxis or therapy of allergy. The methods include administering to the subject having an allergy or susceptible to an allergy a bisphosphonate, thereby treating the allergy. Other methods include administering to the subject having an allergy or susceptible to an allergy a bisphosphonate and at least one immunogen associated with the allergy, thereby treating the allergy. The at least one immunogen can be a component of a commercially available vaccine, such as a commercially available vaccine comprising at least one additional adjuvant (e.g., alum). In one embodiment, the methods further include administering a vaccine, e.g., a commercially available vaccine to the subject.

Non-limiting examples of suitable immunogens for use in such methods may comprise allergen specific (for example Derp1) and allergen non-specific immunogens (for example peptides derived from human IgE, including but not restricted to the stanworth decapeptide (EP 0 477 231 B 1)).

In the methods of the invention, the bisphosphonate and where applicable, the at least one immunogen, may optionally be combined with a pharmaceutical carrier. Suitable pharmaceutical carriers are described supra.

Suitable immunogens for use in the methods of the invention include, infectious agent, an infectious agent-derived product, a cancer antigen, a degenerative disease antigen, an atopic disease antigen, an autoimmune disease antigen, an alloantigen, a xenoantigen, a metabolic disease enzyme or enzymatic product, a recombinantly produced protein or peptide, a chimeric fusion protein, and/or a small molecule, and are described supra.

Suitable commercially available vaccines include those for human and veterinary administration and are described supra.

In various aspects and embodiments of the invention, "stimulating an immune response" includes stimulating either cell-mediated immune responses (responses mediated by antigen-specific T cells and non-specific cells of the immune system) and/or humoral immune responses (responses mediated by antibodies present in the plasma lymph, and tissue fluids). The term "immune response" encompasses both the initial responses to an immunogen as well as memory responses that are a result of acquired immunity. In one embodiment, administration of a vaccine according to a methods of the invention is sufficient stimulate a detectable humoral (antibody) response to an immunogen. In another embodiment, administration of a vaccine according to a method of the invention is sufficient to stimulate a cellular (T cell) response to an immunogen. In another embodiment, administration of a vaccine according to a method of the invention is sufficient to enhance an antibody and a T cell response to an immunogen.

"Stimulating" an immune response refers to an increase in the level of immune response following the administration of a vaccine according to one of the methods of the present invention, relative to the level of immune response when a vaccine of the present invention has not been administered. For example, "stimulating" an immune response may be shown, for example, by the achievement of an increase in an immune response in an individual subject who has been treated according to a method of the invention relative to the level of immune response in the subject before the subject was treated according to the method of the invention. "Stimulating" an immune response may also be shown by the achievement of an increase in an immune response in a group of subjects who have been treated according to a method of the invention, compared with a control group of subjects who have not been treated according to the method of the invention.

Stimulating an immune response can be detected in any number of ways, including a increased expression of one or more of IFN-γ, IFN-α, IL-2, IL-12, TNF-α, IL-6, IL-4, IL-5, IP-10, ISG-54K, MCP-1, or a change in gene expression profile characteristic of immune stimulation as well as responses such as B cell proliferation and dendritic cell (DC) migration, DC maturation, and DC differentiation. Analysis (both qualitative and quantitative) of the immune response can be by any method known in the art, including, but not limited to, measuring serum antibody levels, measuring antigen-specific antibody production (including measuring specific antibody+subclasses), activation of specific populations of lymphocytes such as CD4+ T cells, NK cells or CTLs, production of cytokines such as IFN-γ, IFN-α, IL-2, IL-4, IL-5, IL-10 or IL-12 and/or release of histamine. Measurement of numbers of specific types of lymphocytes such as CD4+ T cells can be achieved, for example, with fluorescence-activated cell sorting (FACS). Cytotoxicity and CTL assays can be performed for instance as described in Raz et al. (1994) Proc. Natl. Acad. Sci. USA 91:95 19-9523 and Cho et al. (2000). Cytokine concentrations can be measured, for example, by ELISA. These and other assays to evaluate the immune response are well known in the art. See, for example, Selected Methods in Cellular Immunology (1980) Mishell and Shiigi, eds., W.H. Freeman and Co.

In some embodiments, stimulating an immune response in animal models may be shown by infecting a group of animals that have been immunized according to a method of the invention (e.g., 3 or more weeks after vaccination) and a group of animals that has not been immunized with a dose of a microorganism that is typically lethal. The magnitude and duration of survival of both groups is monitored. Enhanced survival in the immunized group indicates that the method is effective in stimulating an immune response.

Various in vitro and in vivo assays can be used to determine whether a vaccine has stimulated a T cell response (i.e., to determine whether a T cell or a plurality of T cells has become "activated"). In one embodiment, stimulation of an immune response in T cells can be determined by measuring antigen-induced production of cytokines by T cells, e.g., IFNγ, IL-4, IL-2, IL-10, IL-17 and/or TNFα by T cells. Antigen-produced production of cytokines by T cells can be measured by intracellular cytokine staining followed by flow cytometry. In some embodiments, antigen-induced production of cytokines by T cells can be measured by surface capture staining followed by flow cytometry. In other embodiments, antigen-induced production of cytokines by T cells can be measured by determining cytokine concentration in supernatants of activated T cell cultures using, for example, an ELISA assay, e.g., ELISPOT.

In some embodiments, enhancement of an immune response in T cells can be determined by measuring antigen-induced proliferation of T cells by, e.g., $H^3$-thymidine uptake in dividing T cells, flow cytometry, carboxyfluorescein succinimidyl ester (CFSE) dilution assay. In other embodiments, an immune response in T cells is said to be enhanced if cellular markers of T cell activation (e.g., CD11a CD27, CD25, CD40L, CD44, CD45RO, L-selectin (CD62L), CD45RA, CCR7 and/or CD69 are expressed at higher levels relative to unstimulated cells. In some embodiments, enhancement of an immune response in T cells is measured by assaying cytotoxicity by effector CD8+ T cells against antigen-pulsed target cells. For example, a $^{51}$chromium ($^{51}$Cr) release assay can be performed. Tetramer staining and detection of IFN-γ secretion in response to specific immunogen stimulation may also be used to determine whether a method of the invention has enhanced and/or stimulated an immune response in T cells (Current Protocols in Immunology (John Wiley & Sons, Hoboken, N.Y., 2007; incorporated herein by reference). In some embodiments, the activated T cells are selected from the group consisting of CD4+, CD8+ and gamma-delta T cells. In other embodiments, enhancement of an immune response is determined by determining the activation of NKT and NK cells by, e.g., expression of cell surface molecules such as NK1,1, CD16 and CD56, and granzyme production.

In some embodiments of the methods described herein, the subject exhibits a higher titer of immunogen-specific antibodies relative to a subject not administered the bisphosphonate and, optionally, the at least one immunogen. Antibody titers can be measured using methods known in the art, such as, for example, enzyme-linked immunosorbent assay (ELISA), solid-phase radioimmunoassay (RIA), enzyme-labeled immunohistochemistry (see e.g., Mizutani Y. et al., Enzyme-labeled antigen method: histochemical detection of antigen-specific antibody-producing cells in tissue sections of rats immunized with horseradish peroxidase, ovalbumin, or keyhole limpet hemocyanin. Journal of Histochemistry and Cytochemistry, 57 (2): 101-111 (2009)), and multi-plexed microsphere arrays (see e.g., van der Heyde, H. C. et al. Analysis of Antigen-Specific Antibodies and Their Isotypes in Experimental Malaria, *Cytometry Part A* 71A:242-250 (2007)). Exemplary methods of assay of antibody titers are provided in the Examples.

Methods to determine whether B cells have been directly stimulated are known in the art and include, for example, measuring antibody titers, e.g., ability of antibodies to bind and neutralize antigens at particular dilutions, measuring antibody affinity, measuring affinity maturation of antigen-specific antibodiesdetermining whether memory B cells and/or long-lived plasma cells are present by measurting germinal center reactions, e.g., immunohistochemically, by identifying antibody isotypes (e.g., IgG, IgA, IgE, IgM), by measuring antibody function using, e.g., an antibody neutralization assay, e.g., in an appropriate non-human animal model of infection or disease.

In some embodiments of the invention, the methods described herein are independent of macrophage depletion. Methods to determine if macrophages have been depleted are known to one of ordinary skill in the ar and include, for example, confocal microscopy and flow cytometry.

In some embodiments, the vaccines and methods of the invention are evaluated using one of several suitable model systems. For example, immune responses can be evaluated using well-known in vitro models. Well-known animal models may also be used to evaluate in vivo immune responses and immunity to challenge with an immunogen. Any suitable animal model may be utilized, including, but not limited to, animal models of autoimmune diease (see, e.g., Burkhardt and Kalde (1997) *Rheumatol Intern* 17:91, Peters (2002) Immunol Cell Biol 80:113), cancer (see, e.g., Patel and Goldstein (2004) Current Opinion in Oncolol 16:463-467), infectious disease, e.g., those described in, for example, Brown et al., (1958) J. Bact., 75:499; Stevens et al., (1987) Antimicrob. Agents Chemother., 31:312 [1987]; Stevens et al., J. Infect Dis., 155:220; Alttemeier et al., (1950) Surgery, 28:621; Willis, Topley and Wilson's Principles of Bacteriology, Virology and Immunity. Wilson, G., A. Miles, and M. T. Parker, eds. pages 442-475 1983; Butterton et al., (1996) Infect. Immun., 64:4373; Levine et al., (1983) Microbiol. Rev., 47:510; Freter, J. (1956) Exp. Med., 104:411; Formal et al., (1963) J. Bact., 85:119; Naughton et al., 91996) J. Appl. Bact., 81:65; Jacoby et al., (1994) Exp. Gerontol, 29:89; Massion et al., (1993) Am. J. Respir. Cell Mol. Biol. 9:36.

The dosage of the bisphosphonate to be administered according to the methods of the invention may be in the range of about 1-500,000 µg per dose, about 1-50,000 µg per dose, about 1-5000, about 1-1000 µg per dose, about 1-500 µg per dose, and about 1-100 µg per dose, or about 1-25 µg per dose, as described supra. In methods involving administration of at least one immunogen, the amount of immunogen may be about 1 about 0.01-100,000 µg of immunogen, about 0.01-10,000 µg of immunogen, about 0.01-1000 µg of immunogen, about 0.01-500 µg, about 0.01-100 µg, or about 0.01 to 50 µg, about 1-1000 µg of immunogen, about 1-500 µg, about 1-100 µg, or about 1 to 50 µg. It should be understood that a range between any two figures listed above is specifically contemplated to be encompassed within the metes and bounds of the present invention. Some variation in dosage will necessarily occur depending on the condition of the specific immunogen and the subject being immunized.

The dosage of the commercially available vaccines for use in the vaccines and methods of the invention are known in the art. In one embodiment, the dosage of a commercially available vaccine used is an amount effective to stimulate an immune response based on the prescribing information of the commercially available vaccine. In another embodiment, the dosage of the commercially available vaccine is the amount effective to stimulate an immune response in combination with a bisphosphonate and is lower than the dosage prescribed.

The dosage may be optimized in the methods of the invention so as to stimulate an immune response (e.g., to stimulate the immune response, to stimulate the immune response to at least one immunogen, to enhance the immunogenicity of at least one immunogen, to directly stimulate B cells to produce an antibody to at least one immunogen, to increase T cell activation, to increase migration of dendritic cells to a local lymph node) within desirable limits. For example, it may be optimal to select a dosage that enhances an immune response so as to treat or prevent the occurrence of infection or disease but not so strongly as to have adverse effects. For methods of treatment of infection, disease, or cancer, the dosage may be optimized to a level that serves to most effectively retard or inhibit the infection, disease, or cancer.

In some embodiments of the methods of the invention, the specific dosage(s) of bisphosphonate, and also of any immunogen(s) included in the method, that is to be administered to an individual subject may be tailored to the individual. The dosage selected may depend on the species of the subject, the subject's weight, age, diet and general condition, the components to be administered together with the bisphosphonate and/or immunogen(s), the route of administration, the timing of administration, the number of doses to be administered, and the like.

The methods of the invention may employ any suitable route of administration, as described supra. In specific embodiments, the bisphosphonate, either alone or together with other components provided by the method (e.g., pharmaceutically acceptable carrier, immunogen(s), additional adjuvant(s), commercially available vaccine(s)), is administered to the subject intramuscularly, subcutaneously, intradermally, intranasally, orally, transcutaneously, or mucosally. In other embodiments, a vaccine of the invention is not administered orally.

In some embodiments of the methods described herein, the bisphosphonate, either alone or together with other components provided by the method (e.g., pharmaceutically acceptable carrier, immunogen(s), additional adjuvant(s), commercially available vaccine(s)), is administered more than once. For example, the administration may be repeated twice, three times, four times, five times, six times, or seven or more times. The administration may be repeated at intervals of two weeks, one month, two months, three months, four months, five months, six months, twelve months, eighteen months, two years, three years, four years, five years, six years, seven years, eight years, nine years, or ten or more years.

In some embodiments of the methods described herein, the bisphosphonate is administered simultaneously with the at least one immunogen provided by the method. In other embodiments, the bisphosphonate is administered prior to administration of the at least one immunogen. In another embodiment, the bisphosphonate is administered after administration of the immunogen.

In other embodiments of the methods of the invention, the administration to the subject of the commercially available vaccine and the bisphosphonate is repeated. In one embodiment, the commercially available vaccine and the bisphosphonate are administered simultaneously. In another embodiment, the commercially available vaccine is administered prior to the bisphosphonate. In yet another embodiment, the commercially available vaccine is administered after the bisphosphonate.

In certain embodiments, the at least one immunogen or the commercially available vaccine and the bisphosphonate are administered in a single formulation. A commercially available vaccine and a bisphosphonate can be administered either as separate formulations (e.g., the commercially available vaccine can be administered before, at the same time, or after the bisphosphonate is administered to the subject) or as a single formulation (e.g., the commercially available vaccine can be administered simultaneously with the bisphosphonate). In embodiments in which the commercially available vaccine and the bisphosphonate are administered simultaneously, the commercially available vaccine and the bisphosphonate may be in separate formulations or they may be formulated together, e.g., the commercially available vaccine is re-formulated to include a bisphosphonate. In some embodiment, the bisphosphonate is free bisphosphonate and is not provided in a particle delivery system.

In some embodiments of the methods of the present invention, the migration of dendritic cells (DCs) to a local lymph node (LN) is increased. In one embodiment, the DCs are selected from the group consisting of a dendritic cell, a plasmacytoid dendritic cell, a myeloid dendritic cell, an immature myeloid dendritic cell, and a Langerhans cell. These types of DCs are defined on the bases of structural, functional, and lineage characteristics, as described in Masci, A. M. et al. An improved ontological representation of dendritic cells as a paradigm for all cell types. *BMC Bioinformatics* 10:70 (2009). In some embodiments, the DCs are myeloid dendritic cells. In preferred embodiments, the DCs are plasmacytoid DCs.

Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells. Plasmacytoid dendritic cells differentiate from precursors called "DC2" while myeloid dendritic cells (e.g., monocytes) differentiate from precursors termed "DC1." Plasmacytoid dendritic cells and monocytes are also a type of DC precursor, as they further differentiate into mature dendritic cells.

The migration of dendritic cells to local lymph nodes can be assessed using methods known in the art. The advantages and limitations of various methods for assessing dendritic cell migration are reviewed in Randolph, G. J. et al. Dendritic-cell trafficking to lymph nodes through lymphatic vessels. *Nature Reviews Immunology* 5: 617-628 (2005). These methods include direct lymph node cannulation; ex vivo skin explants; fluorescein isothiocyanate (FITC) painting of skin; interstitial injection of tumor-necrosis factor or lipopolysaccharide, or topical application of agents to skin; particle-transport assay; tagged protein uptake in lung, skin or other tissues; adoptive transfer of DCs; gene-gun induction of DC migration. To quantify increases in numbers of dendritic cells in lymph nodes, dendritic cells can be isolated from lymph nodes using methods described, for example, in Gabrilovich, D. Isolation of dendritic cells from mouse lymph nodes. In *Dendritic Cell Protocols, Methods in Molecular Medicine*, 64: 3-7 (2001). These methods include enrichment of the dendritic cell fraction from the lymph nodes of interest by density gradient centrifugation. Gradients for this purpose include metrizamide, Nycodenz, and Percoll. Further enrichment can be achieved using monoclonal antibodies and flow cytometric cell sorting, magnetic beads separation, panning, or cytotoxic elimination with complement. Exemplary methods for isolating and quantifying dendritic cells from lymph nodes are provided in Example 1 and particularly in Example 1H.

In some embodiments of the methods described herein, the method is independent of Toll-like receptor signaling. As used herein, the term "Toll" is the *Drosophila* gene essential for ontogenesis and anti-microbial resistance. Vertebrate orthologues of Toll have been identified and cloned in vertebrates and are referred to as "Toll-like receptors" ("TLRs"). "TLRs" are transmembrane proteins characterized structurally by a cytoplasmic Toll/interleukin-1 receptor (TIR) domain and by extracellular leucine-rich repeats. TLRs detect and are activated by invading pathogens and binding conserved, microbially derived molecules and that induce signaling cascades for proinflammatory gene expression.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Materials and Methods

The following Materials and Methods were used in the examples below.

Mice.

C57BL/6 mice, 6-12 weeks old, were purchased from Taconic Farms, Charles River, or the Jackson Laboratory. CD11c-DTR-GFP (Probst, H. C. et al. (2005) *Clin. Exp. Immunol.* 141, 398-404) mice were provided by M. Boes; tg7 mice (Maloy, K. J. et al. (1999) *J. Immunol.* 162, 2867-2874), expressing an MHC class II (1-Ab)-restricted TCR specific for a peptide derived from the glycoprotein of VSV, were provided by R. Zinkernagel; MyD88$^{-/-}$TRIP$^{-/-}$ mice having defective TLR signaling (Adachi, O. et al. (1998) *Immunity* 9:143-150) (MyD88−/−TRIF+/−) were provided by R. Mora. Mice were housed in specific pathogen-free conditions in accordance with National Institutes of Health guidelines. All experimental animal procedures were approved by the Institutional Animal Committees of Harvard Medical School and Immune Disease Institute.

Immunization and Infection.

Mice were immunized with the following antigens: 4-hydroxy-3-nitrophenyl-chicken gamma globulin (NP-CGG, 50 μg/dose, Biosearch Technologies), Ovalbulmin (OVA, 100 μg/dose, Sigma), UV-inactivated VSV (Dunt, T. et al. (2007) *Nature* 450, 110-114) ($10^6$ plaque forming units (pfu) equivalent dose). Mice were infected with $10^4$ pfu of VSV serotypes Indiana (VSV-IND) or New Jersey (VSV-NJ). Antigens or viruses were dissolved in 40 μl of PBS and injected into the footpad. All infectious work was performed in designated BL-2 workspaces, in accordance with institutional guidelines, and approved by the Harvard Committee on Microbiological Safety. Mice were retro-orbitally bled at the indicated time points for antigen-specific antibodies measurement.

Bisphosphonate Treatment.

Bisphosphonates (Clodronate (Cl2MDP), Alendronate, Pamidronate and Etidronate, all from Sigma) were dissolved in PBS and injected in the footpad of mice (2 mg/dose) 5 days, 3 days and 1 day before immunization or infection. In indicated experiments, mice were injected in the footpad with 40 μl of clodronate-loaded liposomes (CLL, provided by N. VanRooijen (Van Rooijen, N. & Sanders, A. (1994) *J. Immunol.* Methods 174, 83-93)) 7 or 60 days before antigen administration. Empty liposomes served as controls. The amount of clodronate encapsulated in the liposomes has been determined to be 7 mg/ml of liposome suspension.

Hepatitis B Vaccination.

Engerix-B (GlaxoSmithKline) was diluted 1:1 with a 100 mg/ml solution of Cl2MDP or with PBS. At day 0 and at week 2, mice were subcutaneously injected in both footpads with 40 μl of the mix, that contains 400 ng of Hepatitis B surface antigen adsorbed to 10 ng aluminum hydroxide, with or without 2 mg of Cl2MDP.

VSV Neutralization Assay.

Serum from immunized or infected mice was prediluted 40-fold (or 400-fold) in MEM containing 2% FCS. Serial two-fold dilutions were mixed with equal volumes of VSV (500 pfu/ml) and incubated for 90 minutes at 37° C. in 5% $CO_2$. Serum-virus mixture (100 μl) was transferred to Vero cell monolayers in 96-well plates and incubated for 1 hour at 37° C. The monolayers were overlaid with 100 μl of DMEM containing 1% methylcellulose and incubated for 24 hours at 37° C. Subsequently, the overlay was discarded and the monolayer was fixed and stained with 0.5% crystal violet. The highest dilution of serum that decreased the number of plaques by 50% was taken as the titer.

Detection of Antigen-specific Antibodies.

Circulating antigen-specific antibodies were titrated by endpoint ELISA. Serial 1:3 dilutions of sera were plated onto ELISA plates (Nunc) coated with each given antigen (50 μg/ml). Bound antibodies were detected with alkaline phosphatase-conjugated goat anti-mouse IgG (1:5000, Southern Biotechnology Associated), followed by TMB substrate (Biolegend). Antibody titers are expressed as reciprocal dilutions giving an OD405>mean blank $OD_{405}$ plus 3 SD. Blanks consistently displayed $OD_{405}$<0.1 and <10% variability.

Detection of Hepatitis B Surface (Hbs) Antigen Specific Antibodies.

Serum from immunized mice was pre-diluted 1:5 in PBS 1% bovine serum albumin. Circulating Hbs antigen-specific antibodies were determined with an HbsAb detection kit (Diagnostic Bioprobes), in accordance to the manufacturer's instructions.

Quantification of HbsAb-producing Cells.

The frequency of HbsAb-producing cells in the draining lymph node was determined one week after the second immunization with Engerix-B or Engerix-B and Cl2MDP. Single-cell suspensions were incubated overnight at $5\times10^5$ cells per well, in RPMI medium 1640 (Gibco/Life Sciences) 5% FCS (HyClone), into MultiScreenHTS ELISPOT plates (Millipore) coated with 100 ng/well of recombinant HbSAg antigen adw (PROSPEC). Spots were revealed with an HRP-conjugated goat-anti-mouse IgG antiserum (Santa Cruz Biotechnology) followed by the AEC substrate (Sigma/Aldrich) and enumerated by using computer-assisted video image analysis Axioplan 2 (Zeiss).

Confocal Microscopy.

Popliteal lymph nodes (LN) were harvested and fixed with phosphate-buffered L-lysine with 1% paraformaldehyde/periodate (PLP) over-night at 4 C. The LNs were then cryoprotected by an ascending series of 10%, 20% and 30% sucrose in PBS. Samples were snap-frozen in TBS tissue-freezing liquid (Triangle Biomedical Sciences) and stored at −80° C. Sections of 40 μm thickness were mounted on Superfrost Plus slides (Fisherbrand) and stained with fluorescent antibodies in a humidified chamber after Fc receptor blockade with 1 mg/ml antibody 2.4G2 (BD Pharmigen). Samples were mounted in Fluor Save reagent solution (EMD-Calmbiochem) and stored at 4° C. until analysis. Images were collected with a Bio-Rad confocal microscopy system using an Olympus BX50WI microscope and 10x/0.4 numerical aperture objective lenses. Images were analyzed with Volocity software. The anti-CD169 antibody Ser4 (provided by P. Crocker) was purified from hybridoma supernatants by standard methods (Cooper H. M. & Paterson Y. (2001) *Curr Protoc Mol Biol*. 11:11.14) and biotinylated with a biotinylation kit from Pierce, in accordance with the manufacturer's instructions.

Tissue Digestion and Flow Cytometry.

Single-cell suspensions of LNs and footpads were generated by careful mincing of tissues and subsequent digestion at 37° C. for 40 minutes in DMEM medium in the presence of 250 mg/ml liberase plus 50 mg/ml DNase-I. After 20 min of digestion (1 hour for footpads), samples were vigorously passed through an 18-gauge needle to ensure complete organ dissociation. All flow cytometric analyses were performed in FACS buffer containing PBS with 2 mM EDTA and 2% FBS on a FACS CANTO and analyzed with FlowJo software. Antibodies used included allophycocyanin (APC)-conjugated anti-CD45 (clone 30-F11, BD Pharmingen) phycoerythrin (PE)-Cy7-conjugated anti-CD11b (clone M1/70, eBioscinece), biotinylated anti-Vb2 (clone B20.6, BD Pharmingen), PE-Cy7-conjugated streptavidin (BD Pharmingen), APC-conjugated anti-CD4 (clone $L_3T4$, BD Pharmingen), PE-Cy7-conjugated anti-B220 (clone RA3-6B2, Biolegend), and PE-conjugated anti-CD138 (claone 281-2, BD Pharmigen).

In vivo Depletion of LN Macrophages.

To deplete popliteal LN macrophages mice received every other day starting 5 days prior to immunization i.fp. injections of 2 mg of carrageenan (Sigma) in 40 µl of PBS. Alternatively, 5 days prior to immunization they were injected with a single dose of 1 mg of dextran sulfate (Sigma) i.fp. in 40 µl of PBS. At day 0, depletion of LN macrophages was confirmed by confocal microscopy and flow cytometry. In other experiments, CD11c-DTR-GFP mice received diptheria toxin (DT, 4 ng, Sigma) into the footpad 6 days before the infection. The DT treatment eliminates CD 169+ CD11c$^{low}$ LN macrophages in the popliteal draining LN, while leaving paracortical CD11c$^+$ dendritic cells unchanged (Iannacone, M. et al. (2010) *Nature* 465, 1079-1083).

Dendritic Cell Migration.

DCs were purified by positive immunomagnetic cell sorting (about 98% CD11c$^+$) from spleens of donor βActin-GFP mice (Okabe M. et al. (1997) FEBS Lett 407(3):313-9) that had been implanted with a mouse melanoma cell line secreting the ligand for the receptor tyrosine kinase Flt3 (Bjorck, P. et al. (2001) *Blood* 98, 3520-3526). $5 \times 10^5$ DCs in 20 µl DMEM containing 10 ng LPS (Sigma) were injected into the footpads of recipient mice. Eighteen hours after the transfer, popliteal LNs were harvested and the number of GFP$^+$ DCs migrated to the LN was assessed by flow cytometry and confocal microscopy.

Proliferative Responses of VSV-specific Transgenic CD4+ T Cells.

T cells were purified by positive immunomagnetic cell sorting from the spleen and LNs of tg7 mice and labeled with 5 mM CFSE (carboxyfluorescein diacetate succinimidyl ester), as described (Iannacone, M. et al. (2010) *Nature* 465, 1079-1083). $10^6$ CFSE-labelled tg7 T cells were then transferred intravenously into recipient mice (that were treated or not with CLLs 6 days earlier) 1 day before footpad infection with $10^4$ pfu of VSV-ind. 4 days later, single-cell suspensions from the draining popliteal LNs were analysed by flow cytometry, and the number of total TG7 cells or the number of TG7 cells that underwent at least one division was quantified.

In vitro B Cell Activation.

Naive B cells were negatively selected by magnetic isolation with CD43 beads (Miltenyi), plated at $0.5 \times 10^6$ cells/ml and stimulated or not for 10 days with anti-CD40 (1 mg/ml) plus IL-4 (10 ng/ml) in 200 ul of medium in 96-well plates. Serial 1:10 dilution of Cl2MDP, CLL or empty liposomes were added to the wells, starting from 280 µg of Cl2MDP or 40 µl of CLL or empty liposomes. 280 µg is the amount of Cl2MDP that is encapsuled in 40 µl of CLL.

Example 1

Use of Bisphosphonates as Novel Adjuvants for Adaptive Immune Responses

Bisphosphonates are analogs of pyrophosphate that contain two phosphonate groups attached to a central carbon that replaces the oxygen in pyrophosphate. Because they form a three-dimensional structure capable of chelating divalent cations such as $Ca^{2+}$, the bisphosphonates have a strong affinity for bone, targeting especially bone surfaces undergoing remodeling. Accordingly, they are clinically approved and used extensively in conditions characterized by osteoclast-mediated bone resorption, including osteoporosis, Paget's disease, tumor-associated osteolysis and hypercalcemia. Bisphosphonates target osteoclasts by binding to bone mineral. Osteoclasts release bound bisphosphonate by acidification of the small sealed resorption space and endocytose bisphosphonate along with dissolved salts and matrix fragments. High intracellular exposure to bisphosphonates occurs, allowing expression of cytotoxic activity.

If bisphosphonates are administered in liposomes, they are captured by macrophages, which phagocytose these structures. Clodoronate liposomes (CLL) are micron sized multilameral liposomes that encapsulate the drug clodronate (i.e., dichloromethylene diphosphonate ($CL_2MDP$)) in their empty spaces. They are formed by phoshatidylcholine and cholesterol to increase the stability in serum. Once CLL are injected, they are immediately recognized by macrophages that eat them and form vesicles known as phagosomes. Lysosomes fuse with phagosomes resulting in a phagolysosome, which destroys the liposomal membrane and results in the release of clodronate in the cytosol, where it is mistakenly metabolized as a toxic ATP analog that blocks the ATP translocase of mitochondria. Mitochondria release molecular signals that initiate cell death by apoptosis. CLL treatment is used to selectively deplete macrophages in vivo. FIG. 1 illustrates the mechanism of macrophage depletion by CLL.

It has previously been reported that there were increased antigen-specific antibody titers in immunized animals that had received clodronate-encapsulated liposomes (CLL) prior to immunization. However this phenomenon was been attributed to the local depletion of lymph node macrophages induced by CLL. Unexpectedly, and as described in detail below, it was found that macrophage depletion is not involved in this novel adjuvant activity, because other compounds that cause local depletion of lymph node macrophages (e.g. silica, carrageenan, dextran sulfate) failed to induce an increase in adaptive immune responses following immunization. Thus, bisphosphonates have an intrinsic adjuvant activity.

Indeed, it was found that bisphosphonates increase dendritic cell migration from the site of injection to the local draining lymph nodes, increasing the antigen availability for presentation to T and B cells. Moreover, bisphosphonates directly activated B cells, because direct exposure of B cells to bisphosphonates in vitro triggered the release of immunogloblulins.

Finally, it was found that the adjuvant activity of bisphosphonates occurs independently of the adaptor protein Myd88, which is required for the signaling pathway of most of the known Toll-like receptors.

The use of bisphosphonates as adjuvants, either alone or in combination with existing adjuvants, is particularly attractive, especially in consideration of the fact that they are already clinically approved and that they work through a molecular pathway that is not shared by the known adjuvants.

Figure 2:
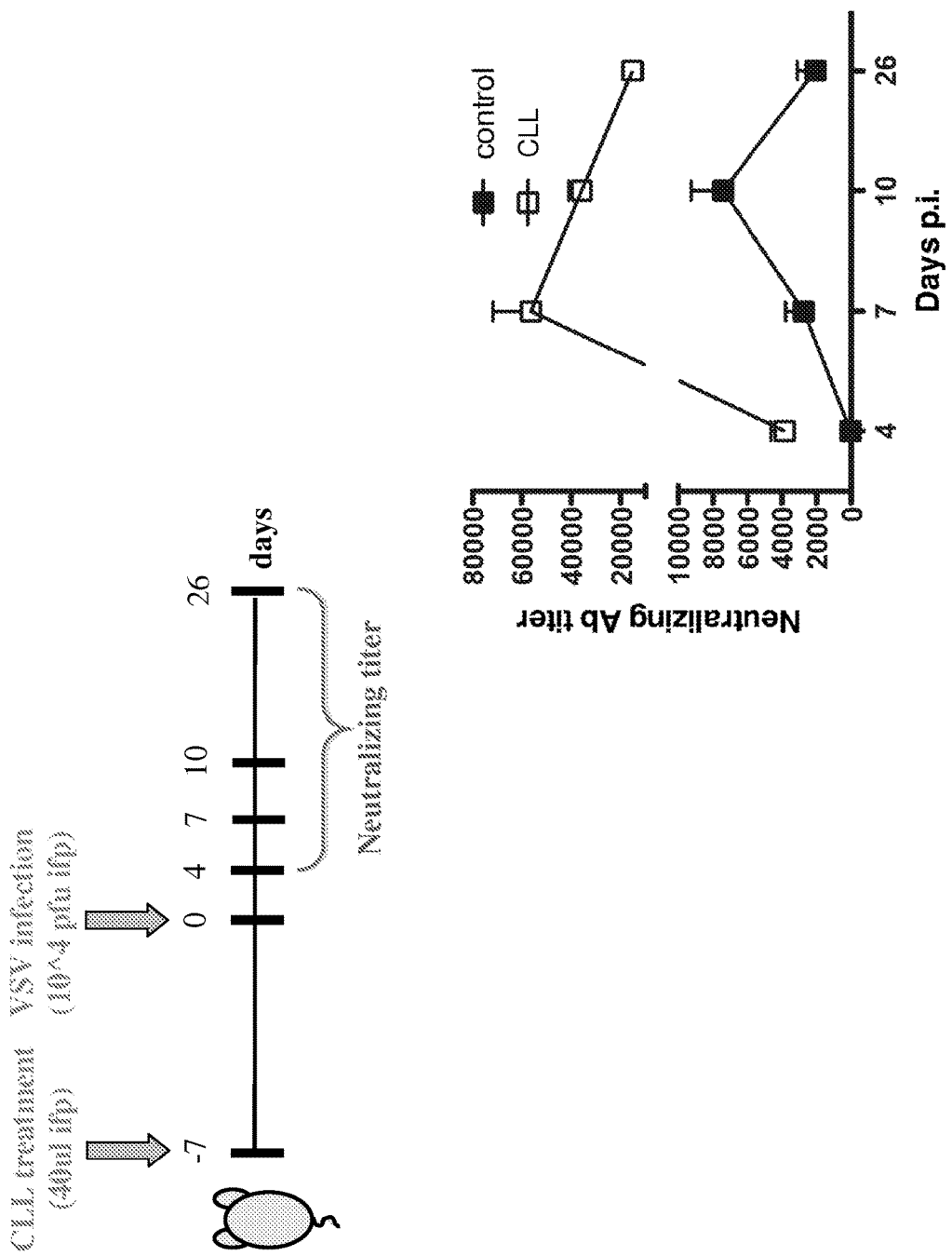
FIG. 2 depicts the timing of administration of clodronate liposomes (CLL) and vesicular stomatitis virus (VSV) to mice and the times following administration at which neutralizing antibody titres were determined. The graph shows that mice administered CLL (open squares) prior to infection with live VSV exhibited significantly higher VSV antigen-specific neutralizing antibody titers than did control mice (solid squares) that were treated with empty liposomes prior to administration of live VSV.

A. Clodronate Liposome-(CLL-)Treated Mice Exhibit Higher Antigen-specific Antibody Titres to Live Virus Seven days before infection by footpad injection with $10^4$ pfu of VSV serotypes Indiana, mice were injected in the footpad either with empty liposomes (control) or with 40 µl of a suspension of clodronate-loaded liposomes (CLL). Serum samples were collected from mice at days 4, 7, 10 and 26 post infection (p.i.) to titrate VSV-specific neutralizing antibodies. As depicted in FIG. 2, mice adminstered CLL prior to infection with live VSV exhibited significantly higher VSV antigen-specific neutralizing antibody titers than did mice that were treated with empty control liposomes prior to administration of live VSV.

Figure 3:
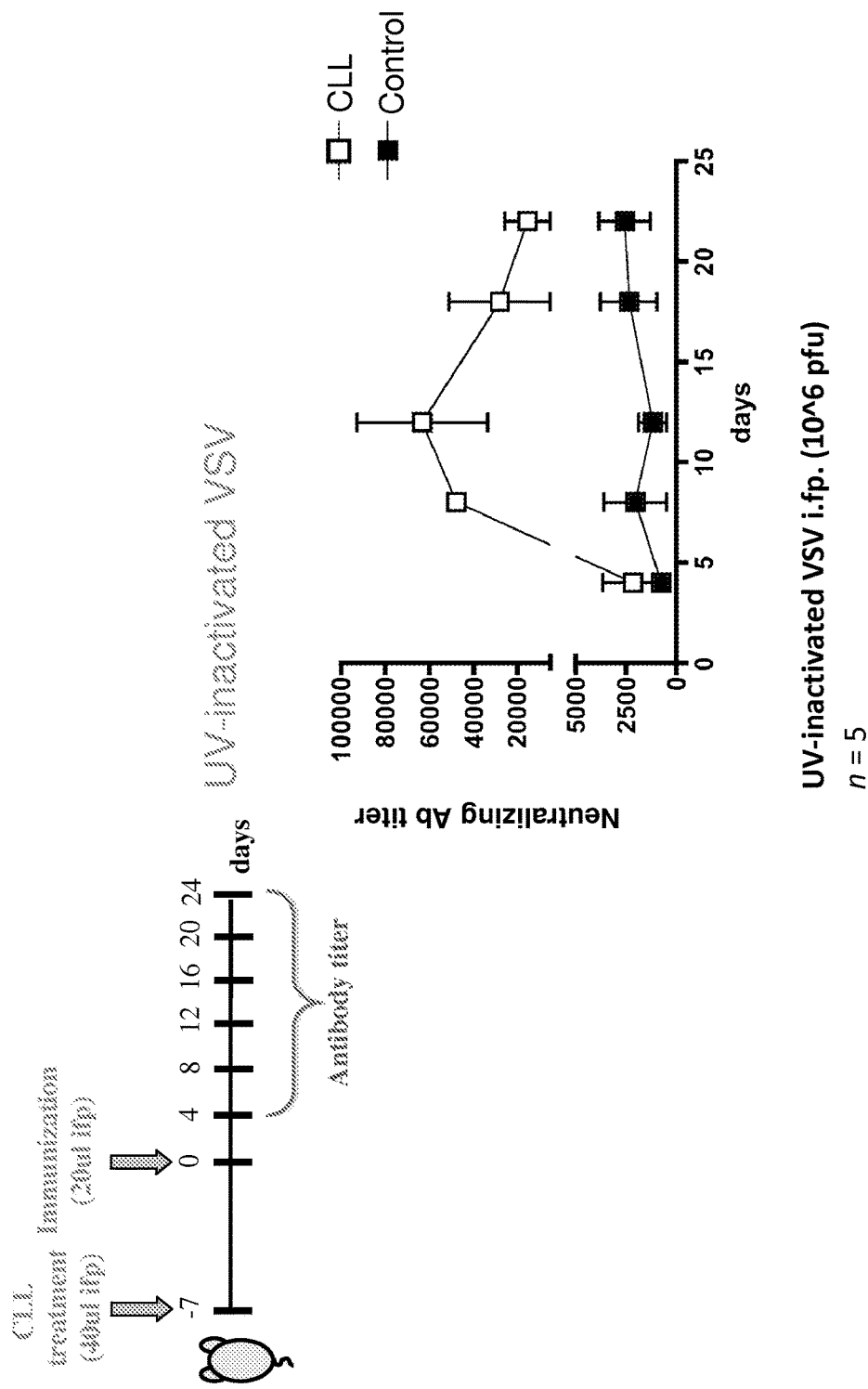
FIG. 3 depicts the timing of administration of clodronate liposomes (CLL) and inactivated vesicular stomatitis virus (VSV) to mice and the times following administration that neutralizing antibody titres were determined. The graph shows that mice administered CLL (open squares) prior to infection with inactivated VSV exhibited significantly higher VSV antigen-specific neutralizing antibody titers than did control mice (solid squares) that were treated with empty liposomes prior to administration of live VSV.

B. Clodronate Liposome-(CLL-)Treated Mice Exhibit Higher Antigen-specific Antibody Titres to Inactivated Virus Seven days before infection by footpad injection with $10^6$ pfu of VSV serotypes Indiana that had been inactivated by ultraviolet irradiation for 15 minutes, mice were injected in the footpad either with empty liposomes (control) or with 40 µl of a suspension of clodronate-loaded liposomes (CLL). Serum samples were collected from mice every 4 days, from 4 days post-infection (p.i.) until 24 days p.i., to titrate VSV-specific neutralizing antibodies. FIG. 3 shows that mice administered CLL prior to infection with inactivated virus also exhibited increased VSV antigen-specific neutralizing antibody titers than did mice that were treated with empty control liposomes prior to administration of inactivated VSV.

C. Clodronate Liposome- (CLL-)Treated Mice Exhibit Higher Antigen-specific Antibody Titres to 4-Hydroxy-3-Nitrophenyl-Chicken Gamma Globulin (NP-CGG) and Ovalbulmin Mice were injected in the footpad with 40 µl of a suspension of clodronate-loaded liposomes (CLL) 7 days before immunization (i.e., at day −7). At day 0, mice were injected intrafootpad with 4-hydroxy-3-nitrophenyl-chicken gamma globulin (NP-CGG, 50 µg/dose) or Ovalbulmin (OVA, 100 µg/dose). NP-CGG immunized mice received also a boost after two weeks with the same dose of antigen. Serum samples were collected at the timepoints indicated in the graphs in FIGS. 4A and 4B and antigen-specific antibody titres were determined by ELISA.

Figure 4:
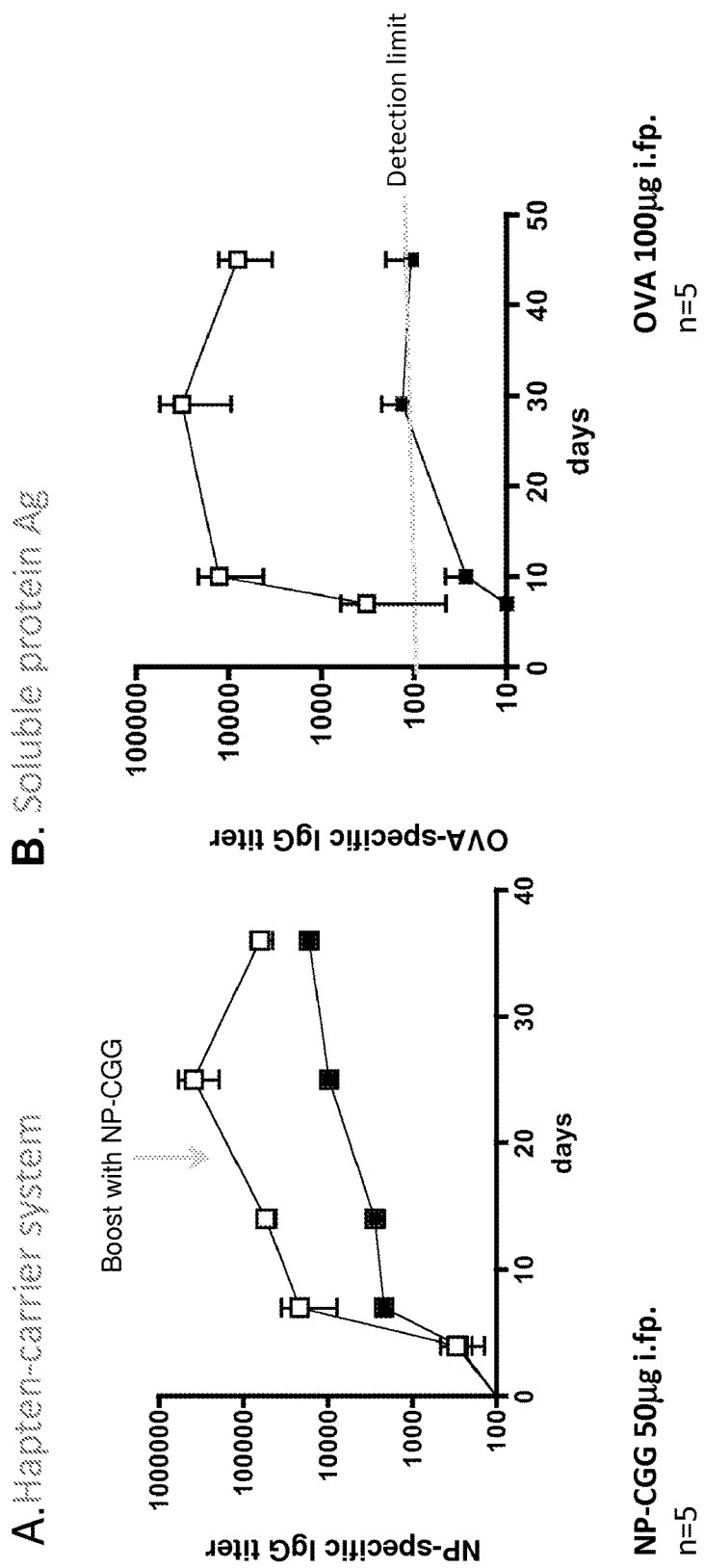
FIGS. 4A and 4B are graphs depicting that mice administered CLL (open squares) prior to a hapten-carrier (A) or a soluble protein antigen (Ag) (B) exhibited significantly higher antigen-specific antibody titers as compared with control mice (solid squares) not treated with CLL prior to administration of antigen.

As shown in FIGS. 4A and 4B, administration of CLL prior to administration of antigens, such as NP-CGG, 50 µg/dose (A) and Ovalbulmin (B) also results in increased antigen-specific antibody titers as compared with mice not treated with CLL prior to administration of antigen.

D. Free Clodronate (Cl2MDP) Treatment Induces an Antigen-specific Antibody Response Five days before immunization, mice were injected in the footpad with 40 µl of a suspension of clodronate-loaded liposomes (CLL), empty liposomes, or free clodronate (Cl2MDP, 2 mg/dose). The same amount of Cl2MDP was also administered at 3 days and 1 day prior to the immunization with antigen. There was also an untreated control group that received no treatment prior to immunization. At day 0, mice were injected intrafootpad with $10^6$ pfu of VSV serotype Indiana that had been inactivated with 15 minutes of ultraviolet radiation.

Figure 5:
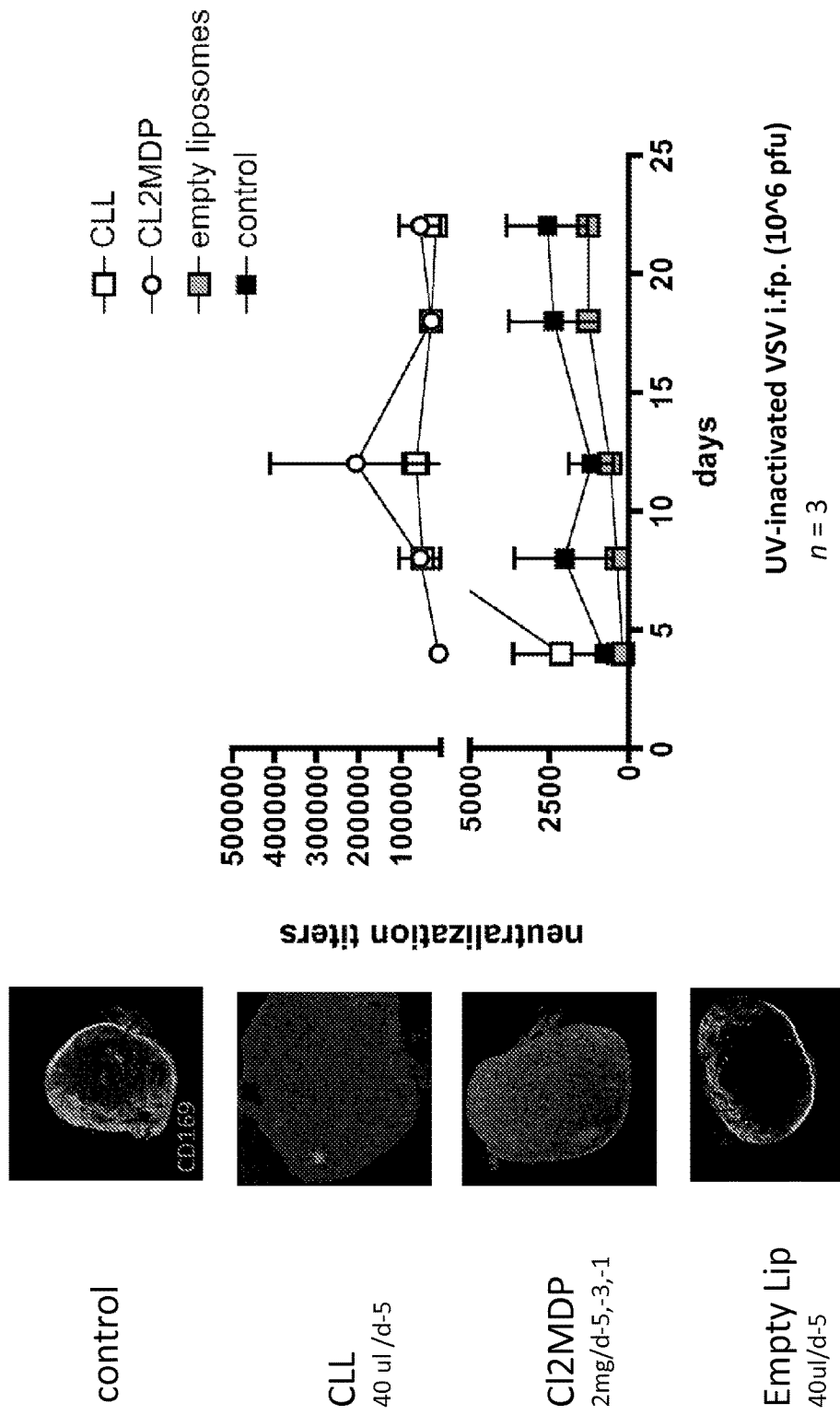
FIG. 5 depicts that empty liposomes were unable to increase VSV antigen-specific antibody titers while free clodronate ($Cl_2MDP$) treatment increased VSV antigen-specific antibody titers to a similar extent as clodronate liposomes. The confocal micrographs on the left show depletion of CD 169+ lymph node macrophages upon CLL or free clodronate treatment.

Serum samples were collected every 4 days, from 4 days post-infection (p.i.) to 24 days p.i., to titrate VSV-specific neutralizing antibodies. Macrophage depletion was assessed by confocal immunofluorescence histology (FIG. 5, left); both CLL and Cl2MDP, but not empty liposomes, deplete CD169+ lymph node macrophages. As depicted in FIG. 5, empty liposomes were unable to increase VSV antigen-specific antibody titers while free clodronate (Cl2MDP) treatment increased VSV antigen-specific antibody titers to a similar extent as did clodronate liposomes.

Figure 6:
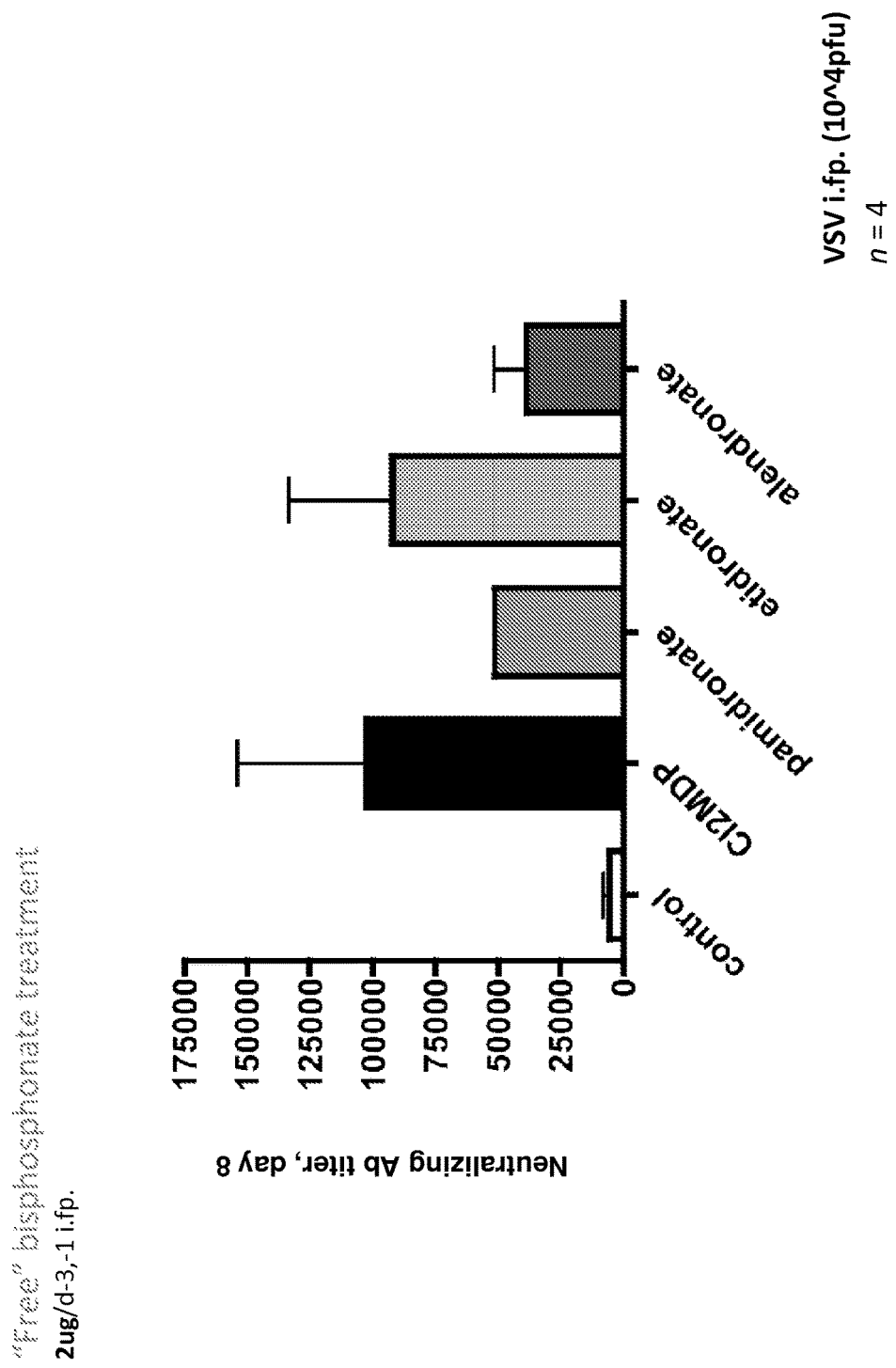
FIG. 6 is a graph depicting that both first generation bisphosphonates (clodronate or Cl2MDP and etidronate) and second-generation aminobisphosphonates (alendronate and pamidronate) administered to mice prior to infection with live VSV increased antigen-specific antibody titers in mice.

E. Treatment with First-Generation Bisphosphonates and with Second-Generation Aminobisphosphonates Increases Antigen-Specific Antibody Responses At days −3 and −1 prior to infection, mice were injected in the footpad with 2 mg of fre clodronate, free pamidronate, free etidronate or free alendronate suspended in 40 µl of PBS. Clodronate and etidronate are first-generation bisphosphonates. Alendronate and pamidronate are second-generation aminobisphosphonates. At day 0, mice were infected intrafootpad with $10^4$ pfu of VSV serotypes Indiana. Serum samples were collected at day 8 to titrate VSV-specific neutralizing antibodies. As shown in FIG. 6, all of the bisphosphonates tested increased VSV antigen-specific neutralizing antibody titers as compared with control mice receiving empty liposomes.

F. Inflammation is not Involved in the Increased Antigen-Specific Antibody Response to Clodronate Mice were injected in the footpad with 40 µl of CLL. After 60 days mice were infected intrafootpad with $10^4$ pfu of VSV serotypes Indiana. Serum samples were collected at indicated time points to titrate VSV-specific neutralizing antibodies. The absence of myeloid infiltration in the footpad and lymph node macrophage depletion at the day of infection was assessed by flow cytometry and confocal microscopy, respectively.

Figure 7:
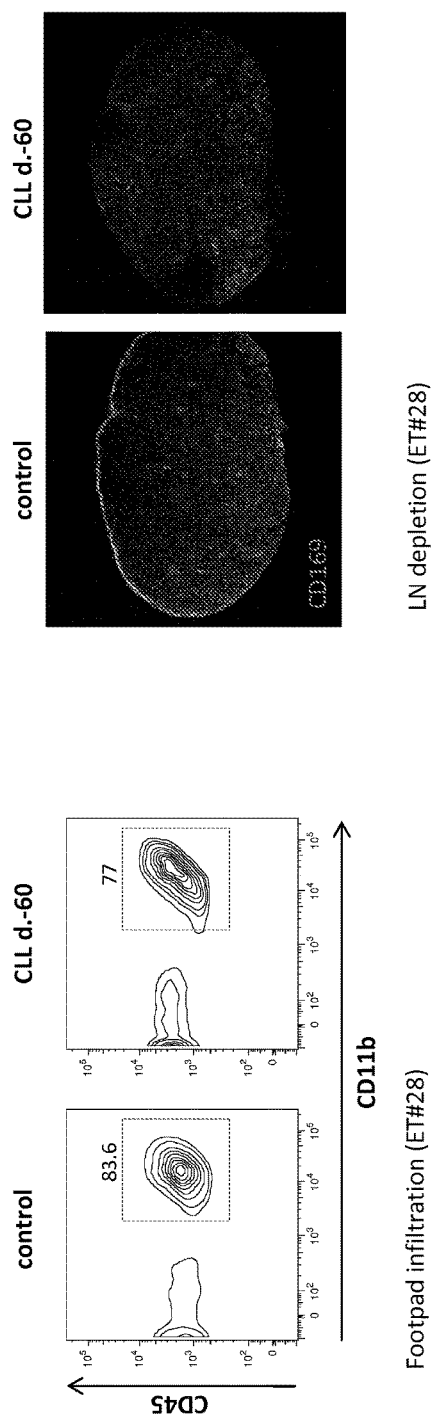
FIG. 7 demonstrates that inflammation is not involved in the increased antigen-specific antibody response to clodronate. Administration of clodronate two months prior to administration of immunogen increased antigen-specific antibody titers although local inflammation had resolved, as assessed by normalization of footpad swelling (not shown) as well as normalization of the inflammatory infiltrate (CD11b+ cells) isolated from the footpad. Confocal micrographs show that CD169+ lymph node macrophages remain depleted.
Figure 7:
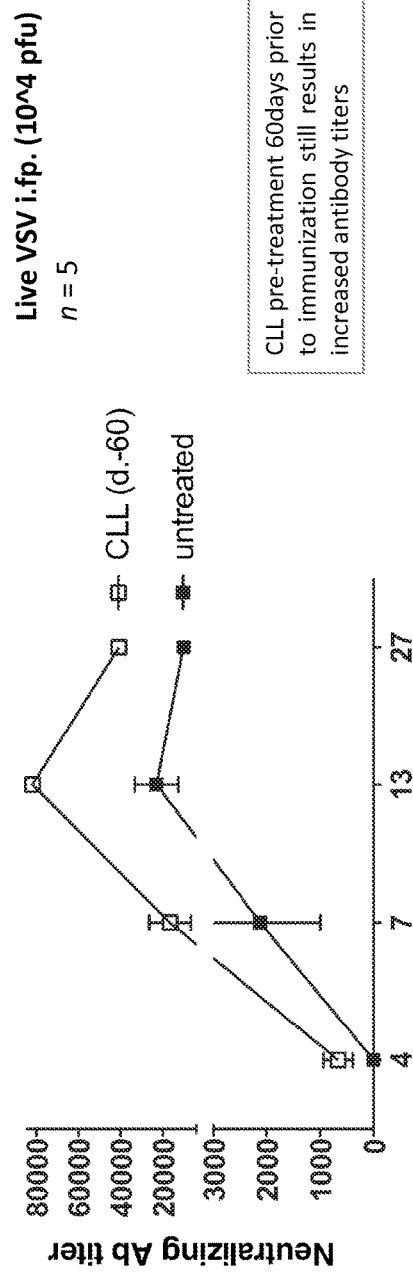

As shown in FIG. 7, 60 days after CLL treatment the footpad inflammation has completely resolved, as verified by the normalitation of footpad swelling (not shown) as well as the normalization of the CD11b+ footpad inflammatory infiltrate (upper left panel). Note that CD 169+ lymph node macrophages are still depleted (upper right panel). Bisphosphonates administered 2 months before infection still enhance the antigen-specific antibody response (FIG. 7, lower panel, even if at that point the inflammation in the footpad is completely resolved. Thus, the footpad inflammation induced by bisphosphonates treatment is not responsible for the adjuvant activity.

Figure 8:
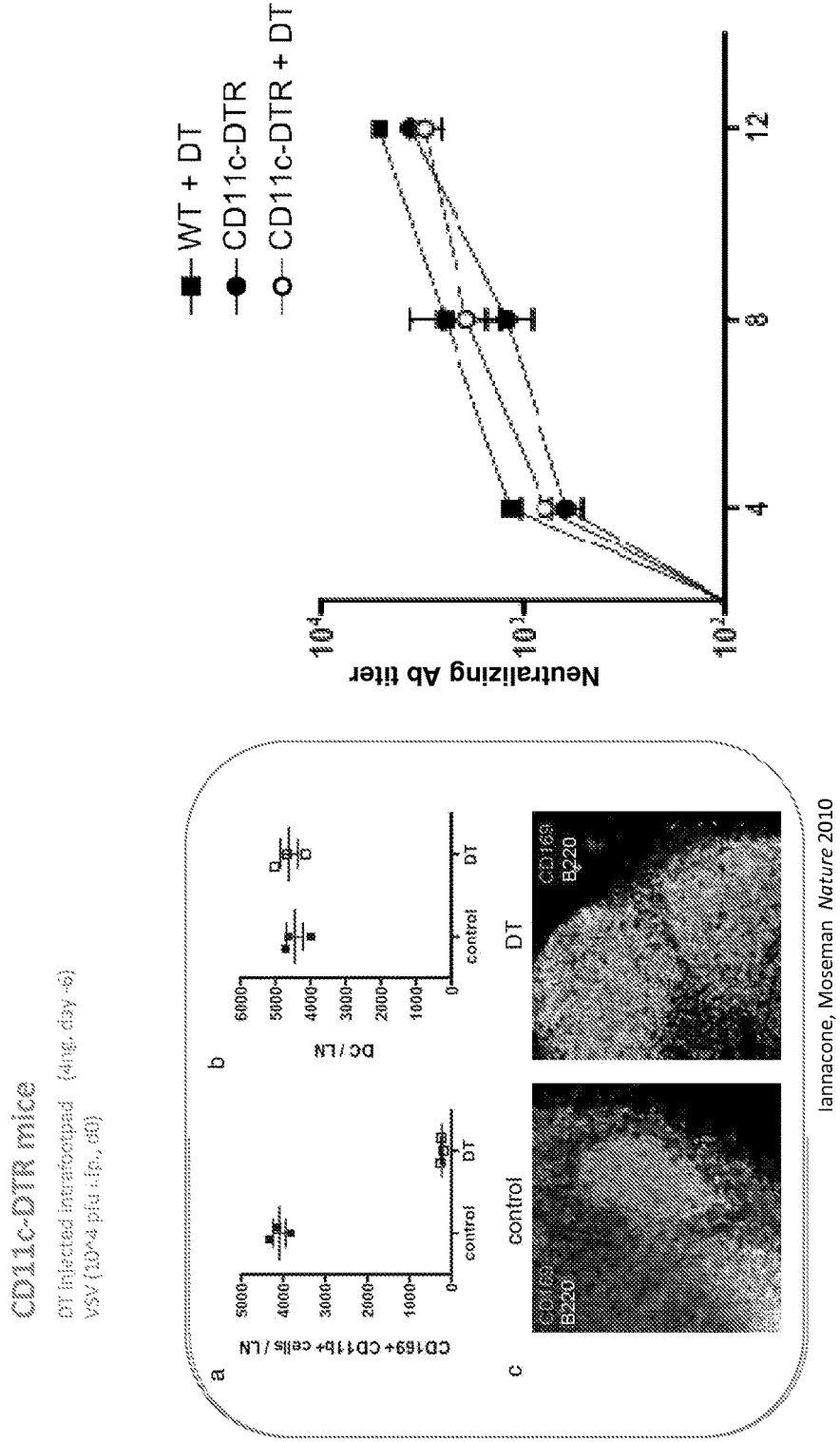
FIG. 8 depicts that macrophage depletion does not cause the increased antigen-specific antibody response observed in CLL treated mice. Treatment of mice with diphtheria toxin (DT), which eliminates CD $169^+$ CD11c$^{low}$ LN macrophages in the popliteal draining LN (as verified by flow cytometry in FIG. 8A and confocal analysis in FIG. 8C), while leaving paracortical CD11c$^+$ dendritic cells unchanged (as verified by flow cytometry in FIG. 8B and confocal analysis in FIG. 8D), prior to infection with VSV failed to induce a neutralizing antigen-specific antibody response (see graph at right).

G. Macrophage Depletion does not Cause the Increased Antigen-Specific Antibody Response Diphtheria toxin (DT, 4 ng, Sigma) was injected into the footpad of CD11c-DTR-GFP and wild-type mice 6 days before infection with VSV. The DT treatment eliminates $CD169^+ CD11c^{low}$ LN macrophages in the popliteal draining LN, while leaving paracortical $CD11c^+$ dendritic cells unchanged. At day 0, mice were infected intrafootpad with $10^4$ pfu of VSV serotype Indiana. On the day of infection, popliteal LN macrophage depletion was verified by flow cytometry (see FIG. 8A) and confocal analysis (see FIG. 8C), and the lack of effect of DT treatment on paracortical $CD11c^+$ dendritic cells was verified by flow cytometry (see FIG. 8B) and confocal analysis (see FIG. 8D). Serum samples were collected at indicated time points to titrate VSV-specific neutralizing antibodies. As shown in the right graph in FIG. 8, DT treatment which depletes macrophages, fails to induce a neutralizing antigen-specific antibody response.

Figure 9:
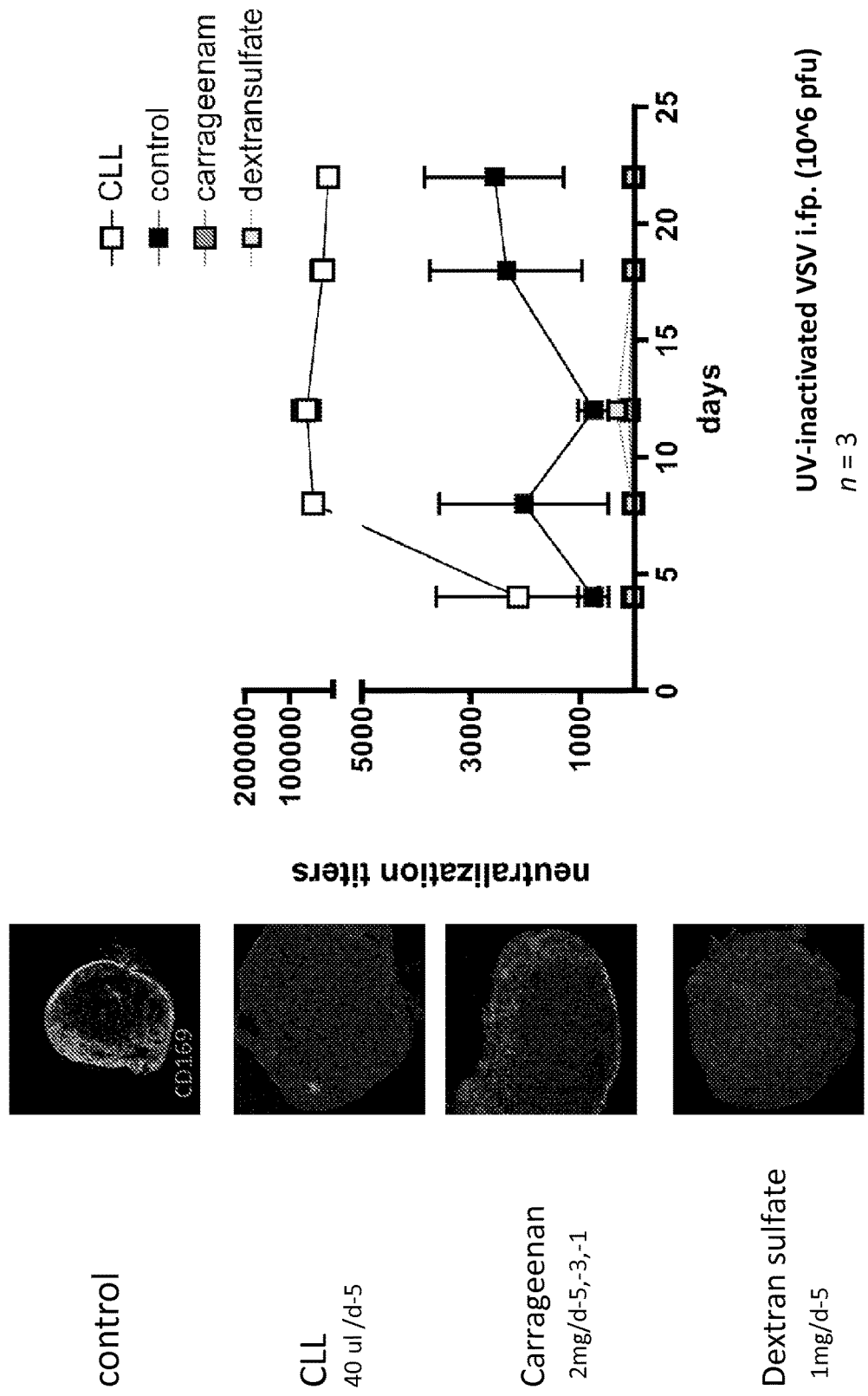
FIG. 9 also depicts that macrophage depletion does not cause the increased antigen-specific antibody response observed in CLL treated mice. Administration of carrageenan and dextran sulfate to mice resulted in local depletion of CD 169+ lymph node macrophages (confocal micrographs) but did not increase antigen-specific antibody titers (see graph at the right).

Additional methods of depleting macrophages were also used to determine if the adjuvant effect observed with bisphosphonates is responsible for the increased antigen-specific antibody response. Mice received intrafootpad injections of 2 mg of carrageenan (Sigma) every other day starting 5 days prior to immunization. Alternatively, 5 days prior to immunization mice were injected with a single dose of 40 µl of CLL or 1 mg of dextran sulfate (Sigma) intrafootpad. At day 0, mice were injected intrafootpad with $10^4$ pfu of VSV serotypes Indiana and depletion of popliteal LN macrophages was confirmed by confocal microscopy (see FIG. 9 photomicrographs) and flow cytometry. Serum samples were collected at indicated time points to titrate VSV-specific neutralizing antibodies. As shown in the graph at the right side of FIG. 9, neither carrageenan treatment or dextran sulfate treatment resulted in an increased antigen-specific antibody response following infection with VSV. These results demonstrate that macrophage depletion does not cause an increased antigen-specific antibody response.

H. Treatment with Liposome-Encapsulated Bisphosphonate Increases Dedritic Cell (DC) Accumulation in the Lymph Nodes (LN)

Figure 10:
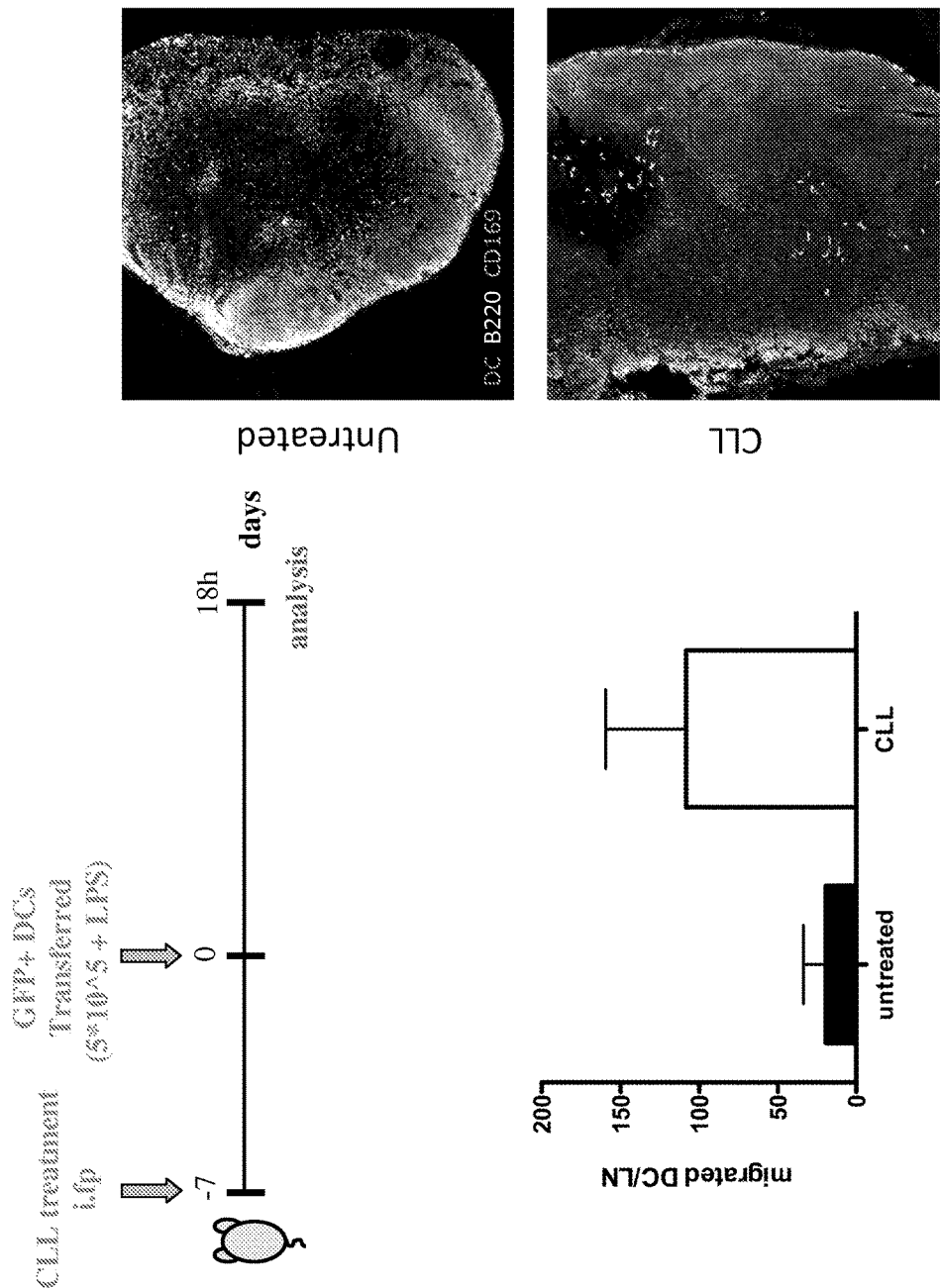
FIG. 10 depicts that CLL treatment increases dendritic cell (DC) migration from the site of injection to the local draining lymph nodes (LN), thereby increasing antigen availability for presentation to T and B cells. The timeline on the upper right shows the timing of the CLL injection, the injection with DCs, and the analysis of DC numbers in LNs. As shown in the graph and in the confocal micrographs to the right, treatment with CLL prior to footpad injection with DCs significantly increased DC migration from the site of injection to the local draining lymph nodes (LN).

Mice were injected in the footpad with 40 µl of a standard suspension of clodronate-loaded liposomes (CLL) 7 days before infection. At day 0, DCs were purified by positive immunomagnetic cell sorting from spleens of donor βActin- GFP mice, and 5×10⁵ DCs were injected into the footpads of recipient mice. Eighteen hours after the transfer, popliteal LNs were harvested and the number of GFP⁺ DCs that had migrated to the LN was assessed by flow cytometry and confocal microscopy. As shown in the graph in FIG. 10, CLL treatment significantly increased DC migration from the site of injection to the local draining lymph nodes (LN), thereby increasing the antigen availability for presentation to T and B cells. Confocal micrographs show increased DC migration in the lymph node of CLL-treated mice.

Figure 11:
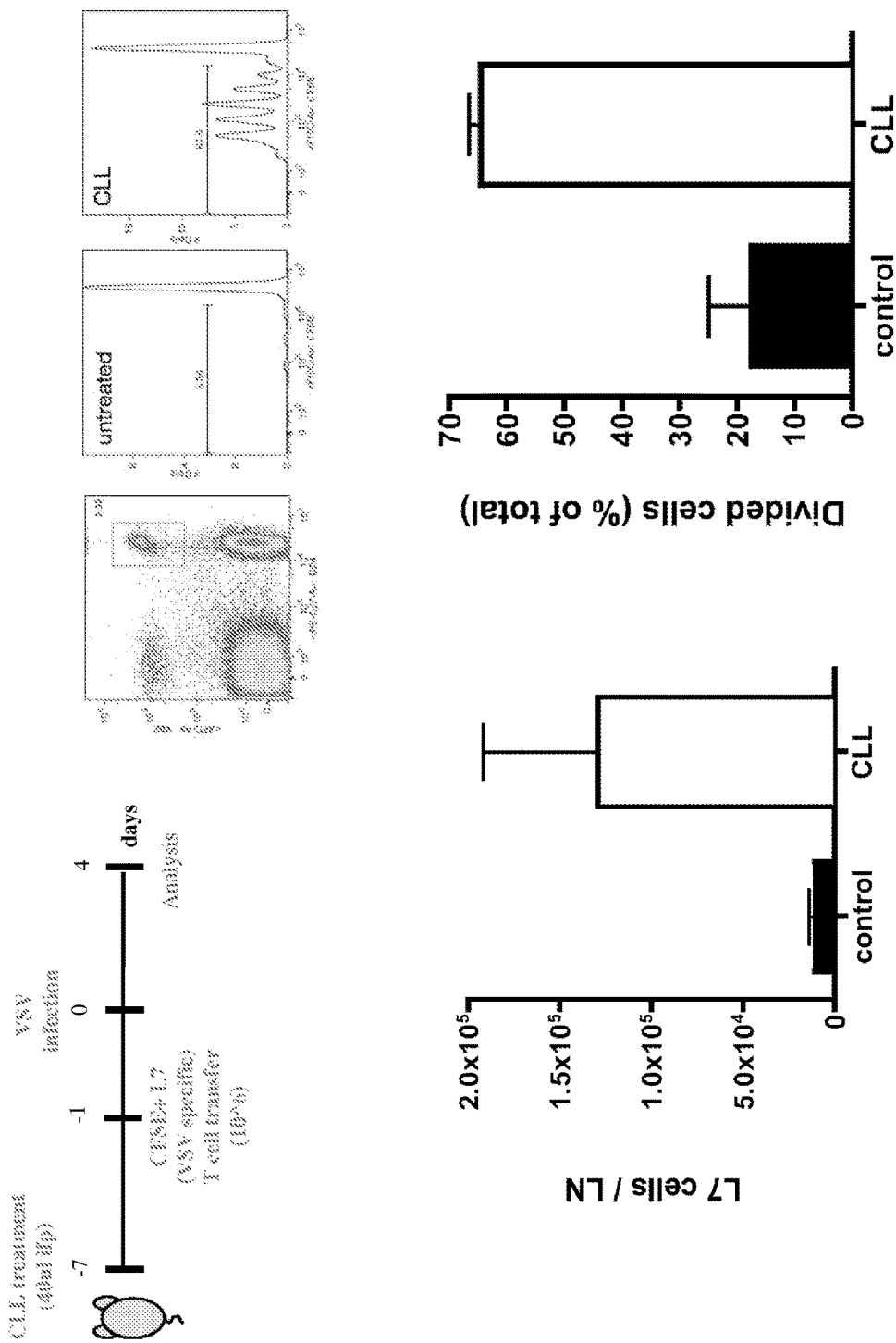
FIG. 11 depicts that CLL treatment increases CD4+ T cell activation. The timeline on the upper left shows the timing of CLL injection, injection of VSV-specific T cells, VSV infection, and analysis of numbers of VSV-specific T cells and numbers of divided VSV-specific T cells in lymph nodes (LNs). As shown in the bar graphs, compared with control mice, mice that were treated with CLL before injection with CFSE-labelled antigen-specific T cells and injection with VSV showed significantly increased numbers of antigen-specific T-cells (lower left graph) and a greater percentage of antigen-specific T cells that had undergone at least one cell division (lower right graph). Facs plot on the upper right depicts the gating strategy for VSV-specific T cells and a representative plot of T cell proliferation profile.

I. Treatment with Liposome-Encapsulated Bisphosphonate Increases T Cell Activation Mice were injected in the footpad with 40 μl of a suspension of clodronate-loaded liposomes (CLL) 7 days before infection. T cells were purified by positive immunomagnetic cell sorting from the spleen and lymph nodes (LNs) of L7 (tg7) mice, which express an MHC class II (I-Ab)-restricted TCR specific for a peptide derived from the glycoprotein of VSV. These T cells were labeled with 5 mM CFSE (carboxyfluorescein diacetate succinimidyl ester). Then, 10⁶ CFSE-labelled L7 T cells were transferred intravenously into recipient mice 1 day before footpad infection with 10⁴ pfu of VSV. Four days post-infection, single-cell suspensions from the draining popliteal LNs were analyzed by flow cytometry, and the number of total L7 cells or the number of L7 cells that underwent at least one division was quantified, using the gating strategy for L7 T cells (CD4+ Vb2+) shown in the right upper panel of FIG. 11. As shown in the bar graphs in FIG. 11, CLL treatment increased the number of antigen-specific T cells in the LNs (left graph) and also increased the percentage of antigen-specific T cells that underwent at least one cell division (right graph). These results indicate that treatment with CLL increases T cell activation.

Figure 12:
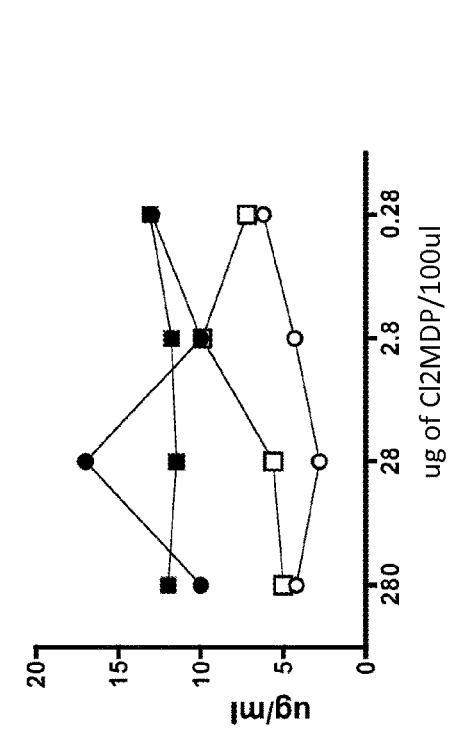
FIGS. 12A-12C depict that contacting B cells in vitro with CLL in the absence of additional stimulation is sufficient to induce antibody secretion and increase the number of antibody forming (B220$^{int}$ CD138$^+$) cells. Naive B cells were negatively selected by magnetic isolation with CD43 beads, plated at 0.5×10$^6$ cells/ml and stimulated or not for 10 days with anti-CD40 (1 mg/ml) plus IL-4 (10 ng/ml) in 200 ul of medium in 96-well plates. Serial 1:10 dilutions of Cl2MDP, CLL or empty liposomes were added to the wells, starting from 280 μg of Cl2MDP or 40 μl of CLL or empty liposomes. 280 μg is the amount of Cl2MDP that is encapsulated in 40 μl of CLL. The amount of IgM produced in each well was determined by endpoint ELISA. Figure (A) shows that CLL increased IgM secretion in unstimulated B cells. Figure (B) is a positive control showing that B cells produce antibodies in response to IL-4 and CD40 ligation. In this case, clodronate or CLL did not have any effect on antibody titers. Figure (C) shows that the number of B cells is increases when treated with CLL in response to IL-4 and CD40 ligation.
Figure 12:
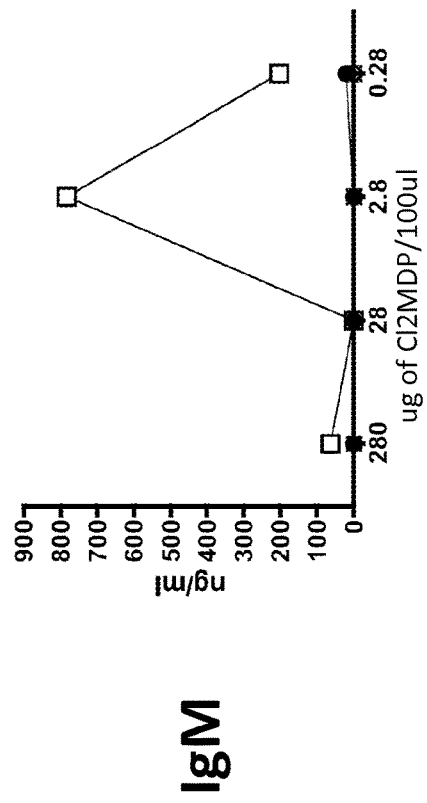
Figure 12:
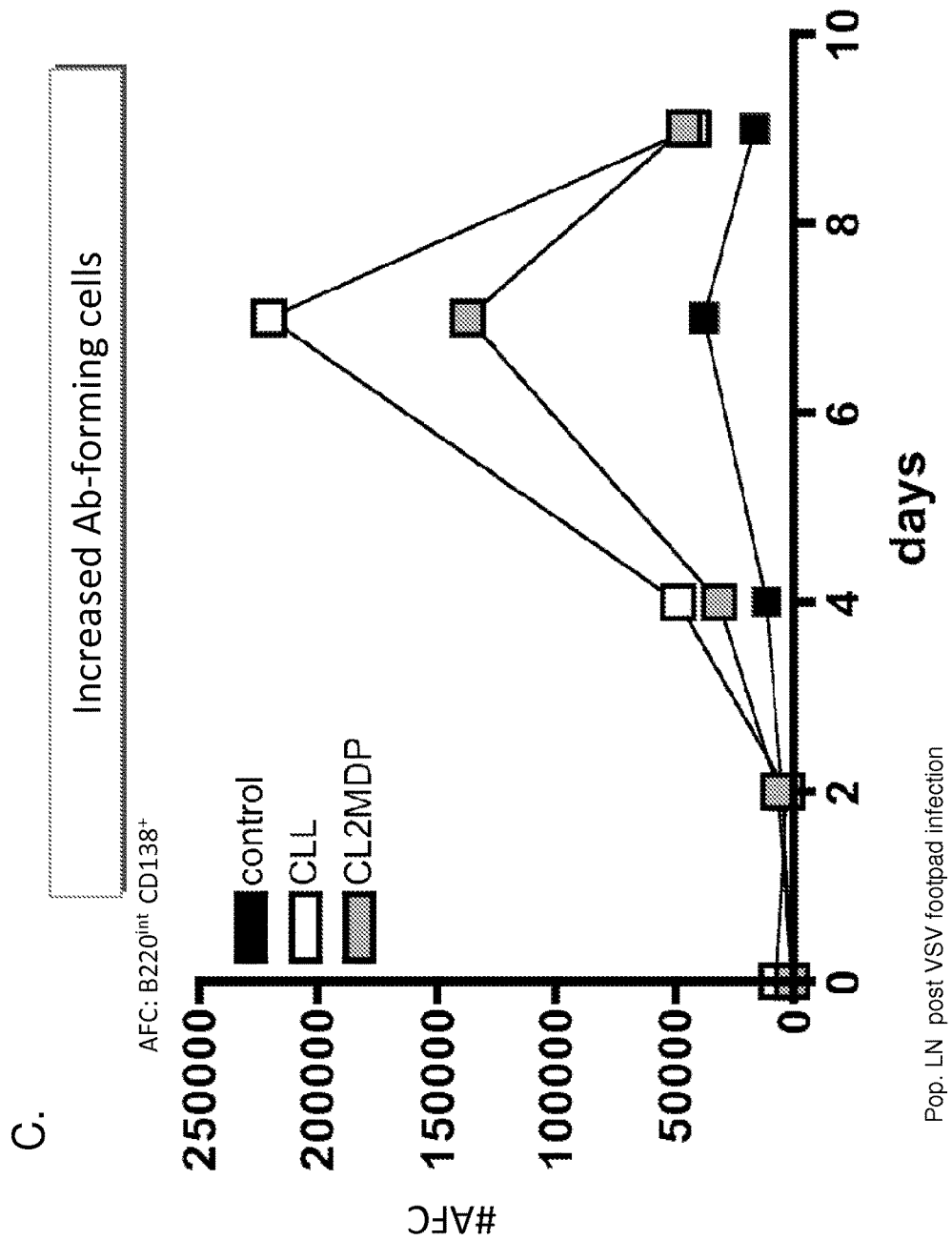

J. Treatment with Liposome-Encapsulated or Free Bisphosphonate Induces Antibody Secretion In Vitro Naive B cells were negatively selected by magnetic isolation with CD43 beads, plated at 0.5×10⁶ cells/ml and stimulated or not for 10 days with anti-CD40 (1 mg/ml) plus IL-4 (10 ng/ml) in 200 μl of medium in 96-well plates. Serial 1:10 dilutions of Cl2MDP, CLL or empty liposomes were added to the wells, starting from 280 μg of Cl2MDP or 40 μl of CLL or empty liposomes. 280 μg is the amount of Cl2MDP that is encapsulated in 40 μl of CLL. The amount of IgM produced in each well was determined by endpoint ELISA. As shown in FIG. 12A, contacting B cells in vitro with CLL in the absence of additional stimulation was sufficient to induce IgM secretion. FIG. 12B is a positive control showing that B cells produce antibodies in response to IL-4 and CD40 ligation. In this case, clodronate or CLL did not have any effect on antibody titers. FIG. 12C shows that the number of B cells is increased when B cells are contacted with CLL.

Figure 13:
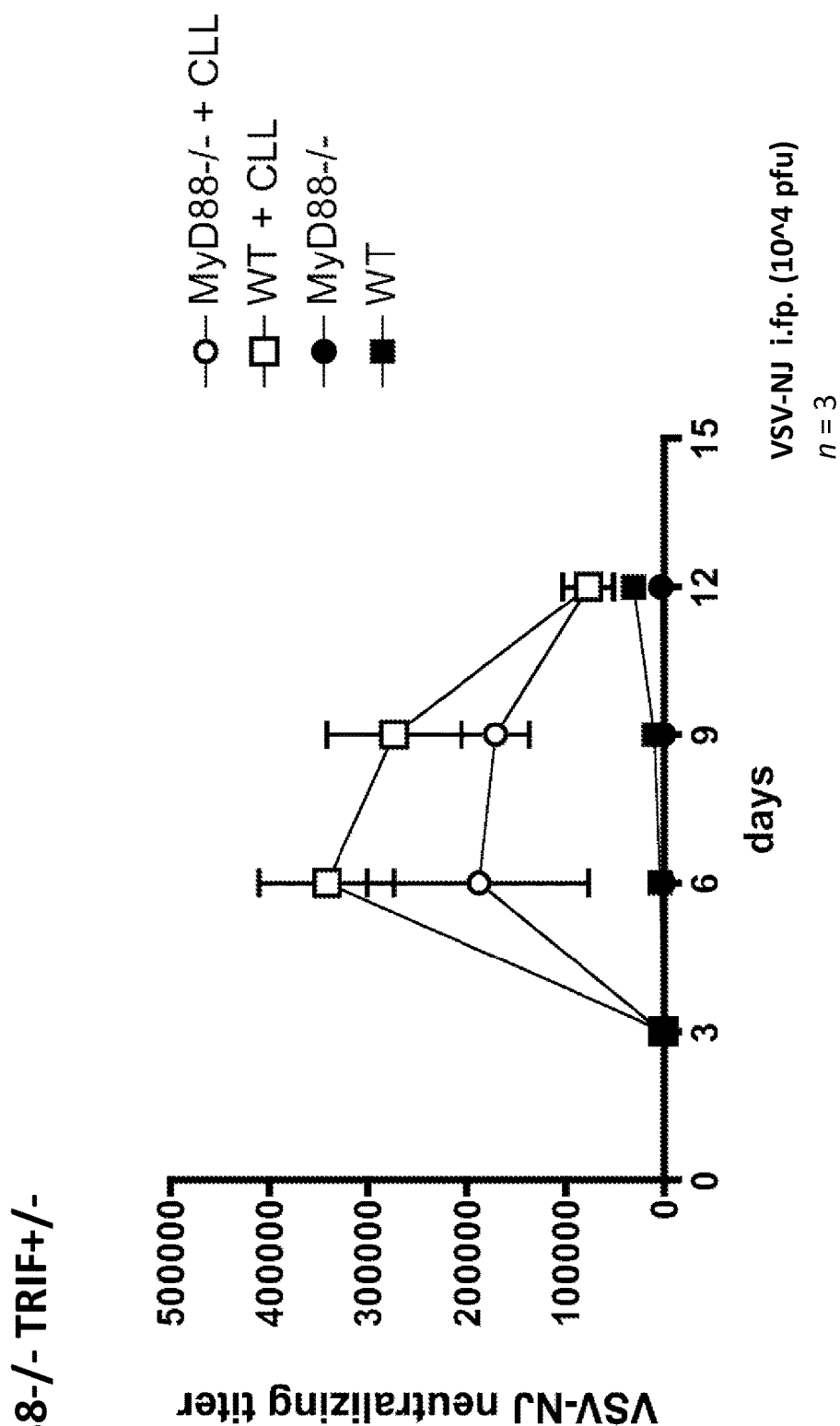
FIG. 13 depicts that TLR signaling is not involved in the adjuvant activity of bisphosphonates. Myd88 deficient or wild type mice were injected in the footpad with 40 μl of a suspension of clodronate-loaded liposomes (CLL) seven days before infection. At day 0, mice were infected with 10$^4$ pfu of VSV serotype New Jersey injected into the footpad in 40 μl of PBS. Serum samples were collected at indicated time points to titrate VSV-specific neutralizing antibodies CLL treatment increased the level of VSV antigen-specific neutralizing antibody titers in wild-type and Myd88 deficient mice to a similar extent.

K. The Bisphosphonate-Induced Antigen-Specific Antibody Response is Independent of TLR Signalling Myd 88 is required for the signalling pathway of most known Toll-like receptors. Myd88 deficient (MyD88⁻/⁻ Trif⁺/⁻) or wild type (WT) mice were injected in the footpad with 40 μl of a suspension of clodronate-loaded liposomes (CLL) 7 days before infection. At day 0, mice were infected with 10⁴ pfu of VSV serotypes New Jersey injected into the footpad in 40 μl of PBS. Serum samples were collected at indicated time points to titrate VSV-specific neutralizing antibodies. In both MyD88⁻/⁻ and WT mice, CLL treatment significantly increased the level of VSV antigen-specific neutralizing antibody titers. As shown in FIG. 13, the levels of VSV antigen-specific neutralizing antibody titers did not differ significantly between CLL-treated MyD88⁻/⁻ and CLL-treated WT mice. These results indicate that TLR signaling is not involved in the adjuvant activity of bisphosphonates.

L. When Combined with Energix-B, Bisphosphonates Increase the Onset of Production of Hepatitis B Surface Antigen Specific Neutralizing Antibodies, Increase the Titres of Hepatitis B Surface Antigen Specific Neutralizing Antibodies, and Increase the Number of Hepatitis B Surface Antigen Specific Producing Cells Twenty μl of Energix-B (400 ng Hepatitis B surface antigen absorbed onto 10 ng aluminum hydroxide; see prescribing information for Energix-B), with and without clodronate, were administered to mice intrafootpad at day 0 and at week 2. Circulating Hepatitis B surface antigen-specific antibody titres were determined using a commercially available kit (see Materials and Methods) at numerous time points following administration. The number of Hepatitis B surface antigen-specific antibody producing cells in draining popliteal lymph nodes were assessed by ELISPOT at week three.

Figure 14:
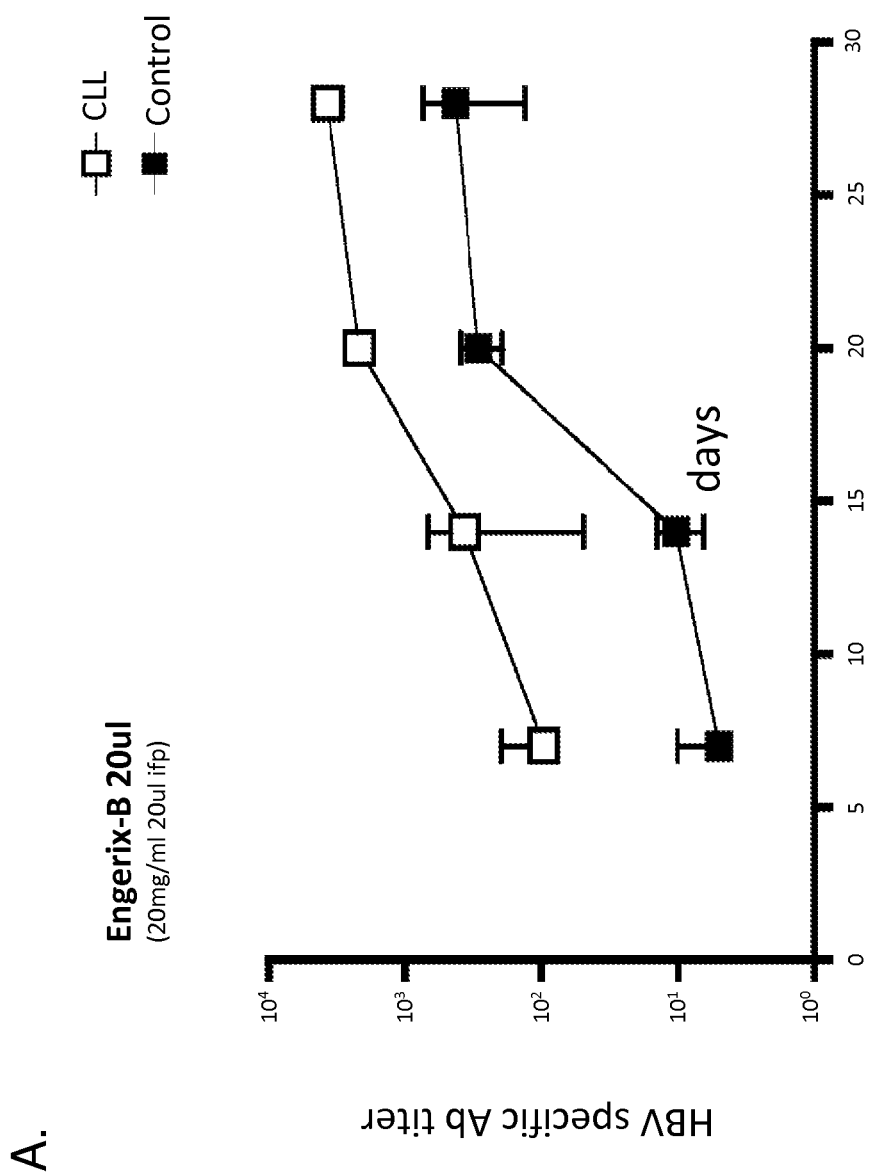
FIGS. 14A-14C are graphs depicting that when a bisphosphonate is combined with Energix-B®, the onset of production of Hepatitis-B surface antigen-specific antibodies is accelerated (14A), the Hepatitis-B surface antigen-specific antibody titres are increased, and the number of Hepatitis-B surface antigen-specific producing cells are increased as compared to when Energix-B is administered alone.
Figure 14:
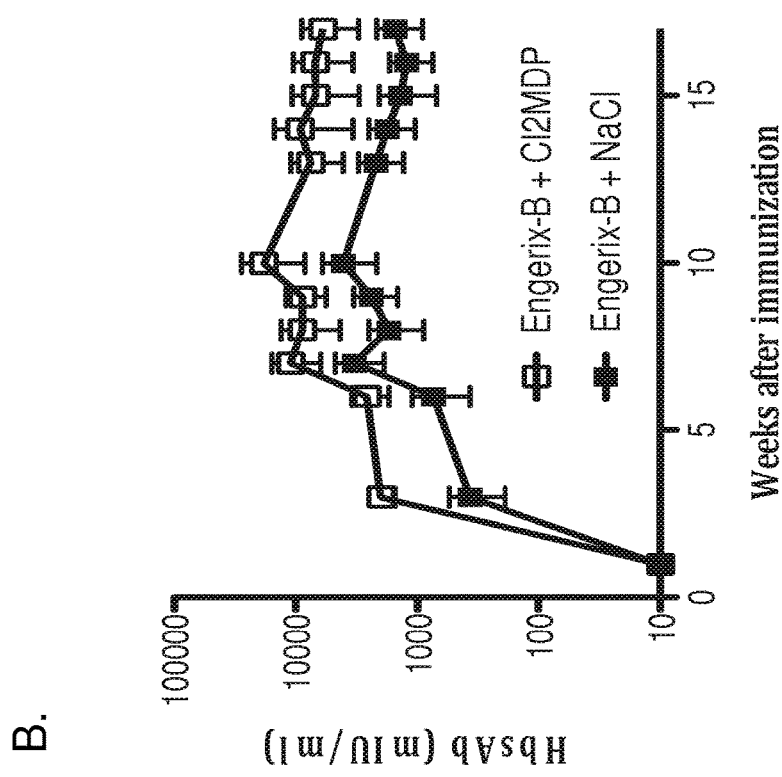
Figure 14:
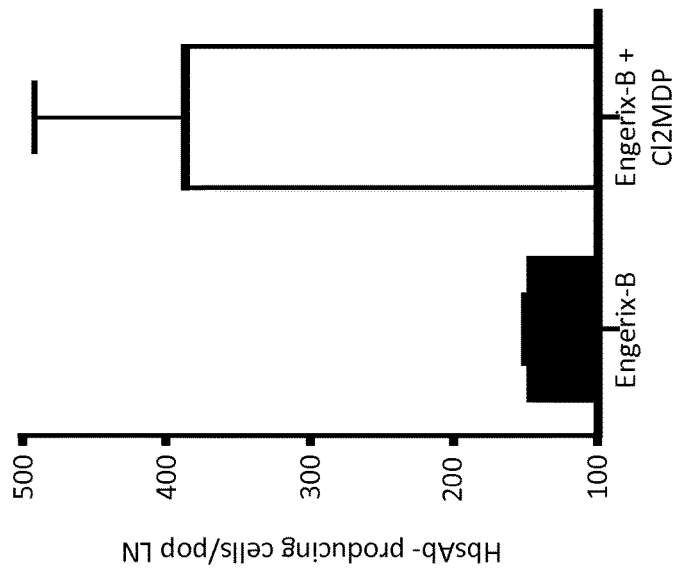

As depicted in FIGS. 14A-14C, not only do mice vaccinated with the Energix-B vaccine and with a bisphosphonate have a faster onset of Hepatitis B surface antigen-specific antibody titers (FIG. 14A), but also have higher Hepatitis B surface antigen-specific antibody titers at day 5 (FIG. 14A) which are maintained for weeks after administration of the Energix-B vaccine and the bisphosphonate as compared to mice administered Energix-B vaccine and not administered a bisphosphonate (FIGS. 14A and 14B). Furthermore, the number of Hepatitis B surface antigen-specific antibody producing cells is significantly increased in animals administered the commercially available vaccine and a bisphosphonate as compared to aminals in which the commercially available vaccine was administered alone.

EQUIVALENTS

Those skilled in the art will recognize, or be able to ascertain using no more that routine experimentation, many equivalents to the specific embodiments of the invention described herein. Such equivalents are intended to be encompassed by the following claims.

We claim:

1. A method for stimulating an immune response to at least one viral immunogen in a human subject, comprising
   administering to the subject a single dose of about 0.001 mg to about 5.0 mg of a bisphosphonate to stimulate an immune response to the at least one viral immunogen in the subject,
   wherein the bisphosphonate is free bisphosphonate and is not provided as a component of a particle delivery system, and
   wherein the at least one viral immunogen and the bisphosphonate contact a population of naïve B cells in the subject and directly stimulate B cells to produce a neutralizing antibody specific to the at least one viral immunogen,
   thereby stimulating an immune response to the at least one viral immunogen in the subject.

2. A method for stimulating an immune response to a viral immunogen present in a vaccine in a human subject, comprising
   administering to the subject a vaccine comprising a viral immunogen;
   administering to the subject a single dose of about 0.001 mg to about 5.0 mg of a bisphosphonate, wherein the bisphosphonate is free bisphosphonate and is not provided as a component of a particle delivery system, and wherein the viral immunogen and the bisphosphonate contact a population of naïve B cells in the subject and directly stimulate B cells to produce a neutralizing antibody specific to the viral immunogen, thereby stimulating an immune response to the viral immunogen present in the vaccine in the subject.

3. A method for enhancing the immunogenicity of at least one viral immunogen in a human subject, comprising administering to the subject the at least one viral immunogen and a single dose of about 0.001 mg to about 5.0 mg of a bisphosphonate, wherein the bisphosphonate is free bisphosphonate and is not provided as a component of a particle delivery system, and wherein the viral immunogen and the bisphosphonate contact a population of naïve B cells in the subject and directly stimulate B cells to produce a neutralizing antibody specific to the viral immunogen, thereby enhancing the immunogenicity of the at least one viral immunogen in the subject.

4. A method for directly stimulating B cells to produce a neutralizing antibody specific to at least one viral immunogen, comprising contacting a population of naïve B cells with a viral immunogen and a single dose of about 0.001 mg to about 5.0 mg of a bisphosphonate;

wherein the bisphosphonate is free bisphosphonate and is not provided as a component of a particle delivery system, thereby directly stimulating the B cells to produce the antibody to at least one viral immunogen.

5. The method of any one of claims 1-4, wherein the immunogen is a component of a commercially available vaccine.

6. The method of any one of claims 1-4, wherein said immunogen is a pathogen.

7. The method of any one of claims 1-4, wherein said immunogen comprises a pathogen product.

8. The method of any one of claims 1-4, wherein the at least one immunogen and the bisphosphonate are combined with a pharmaceutically acceptable carrier.

9. The method of claim 8, wherein the at least one immonogen and the bisphosphonate combined with a pharmaceutically acceptable carrier are further combined with at least one additional adjuvant.

10. The method of claim 1, further comprising administering to the subject a commercially available vaccine.

11. The method of any one of claims 1-4, wherein said method is independent of Toll-like receptor signaling.

12. The method of any one of claims 1-4, wherein the bisphosphonate is selected from the group consisting of Etidronate, Clodronate, Pamidronate, Alendronate, Neridronate, Incadronate, Olpadronate, Ibandronate, risedronate, and Zoledronate.

13. The method of claim 4, wherein the contacting is performed in vitro.

14. The method of claim 4, wherein the contacting is performed in vivo.

15. The method of any one of claims 1-4, wherein the immunogen comprises an inactivated viral pathogen.

16. The method of any one of claims 1-4, wherein the viral immunogen is selected from the group consisting of a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

17. The method of any one of claims 1-3, further comprising determining the titre of neutralizing antibodies specific to the at least one viral immunogen in a sample obtained from the subject.

18. The method of claim 4, further comprising determining the titre of neutralizing antibodies specific to the at least one viral immunogen produced by the naïve B cells.

19. The method of any one of claims 1-4, wherein the neutralizing antibody specific to the viral immunogen is an IgG antibody.

20. The method of claim 2, wherein administration of the vaccine and the bisphosphonate increases the titre of neutralizing antibody specific to the at least one viral immunogen as compared to the tire of the neutralizing antibody specific to the at least one vital immunogen when the bisphosphonate is not administered.

\* \* \* \* \*